United States Patent
Nakai et al.

(10) Patent No.: US 9,677,088 B2
(45) Date of Patent: Jun. 13, 2017

(54) ADENO ASSOCIATED VIRUS PLASMIDS AND VECTORS

(71) Applicants: Oregon Health & Science University, Portland, OR (US); University of Pittsburgh of the Commonwealth System of Higher Education, Pittsburgh, PA (US)

(72) Inventors: Hiroyuki Nakai, West Linn, OR (US); Kei Adachi, Portland, OR (US)

(73) Assignees: Oregon Health & Science University, Portland, OR (US); University of Pittsburgh of the Commonwealth System of Higher Education, Pittsburgh, PA (US)

(*) Notice: Subject to any disclaimer, the term of this patent is extended or adjusted under 35 U.S.C. 154(b) by 61 days.

(21) Appl. No.: 14/399,428

(22) PCT Filed: May 9, 2013

(86) PCT No.: PCT/US2013/040415
§ 371 (c)(1),
(2) Date: Nov. 6, 2014

(87) PCT Pub. No.: WO2013/170078
PCT Pub. Date: Nov. 14, 2013

(65) Prior Publication Data
US 2015/0126588 A1    May 7, 2015

Related U.S. Application Data

(60) Provisional application No. 61/644,814, filed on May 9, 2012, provisional application No. 61/664,537, filed on Jun. 26, 2012.

(51) Int. Cl.
*A61K 48/00* (2006.01)
*C12N 15/86* (2006.01)
(Continued)

(52) U.S. Cl.
CPC ........... *C12N 15/86* (2013.01); *C07K 14/005* (2013.01); *C12N 7/00* (2013.01); *A61K 48/00* (2013.01);
(Continued)

(58) Field of Classification Search
CPC .......... C12N 15/86; C12N 2750/14122; C12N 2750/14141; C12N 7/00; C12N 2710/10043; C07K 14/05; A61K 48/00
See application file for complete search history.

(56) References Cited

U.S. PATENT DOCUMENTS 7,588,772 B2    9/2009  Kay et al.
7,892,809 B2    2/2011  Bowles et al.
(Continued)

FOREIGN PATENT DOCUMENTS

WO    2012/109570    8/2012
WO    2012/112832    8/2012
(Continued)

OTHER PUBLICATIONS

Blast alignment of sequences performed on May 24, 2016 on http://blast.ncbi.nlm.nih.gov/Blast.cgi?PROGRAM=blastp&PAGE_TYPE=BlastSearch&LINK_LOC=blasthome: Appendix A: Alignment of Chatterjee SEQ ID No. 1 (AAV9) as compared to instant SEQ ID No. 1.*

(Continued)

*Primary Examiner* — Reza Ghafoorian
(74) *Attorney, Agent, or Firm* — Stoel Rives LLP; Zhi-Xiang (Alex) Oh

(57) ABSTRACT

Disclosed herein are adeno associated viral plasmids and viral vectors. Also disclosed are methods of using adeno associated viral vectors.

15 Claims, 20 Drawing Sheets

(51) Int. Cl.
    *C07K 14/005* (2006.01)
    *C12N 7/00* (2006.01)
(52) U.S. Cl.
    CPC .............. *C12N 2710/10043* (2013.01); *C12N 2750/14122* (2013.01); *C12N 2750/14141* (2013.01)

(56) References Cited

U.S. PATENT DOCUMENTS

| 7,906,111 | B2 | 3/2011 | Wilson et al. | |
|---|---|---|---|---|
| 2010/0104561 | A1* | 4/2010 | Zhong ................ | A61K 48/0091 514/1.1 |
| 2011/0294218 | A1 | 12/2011 | Chatterjee et al. | |

FOREIGN PATENT DOCUMENTS

| WO | 2013-159036 | 10/2013 |
|---|---|---|
| WO | 2013-170078 | 11/2013 |

OTHER PUBLICATIONS

International Search Report issued in PCT/US2013/040415 on Sep. 25, 2013.
Kei et al., "A New Recombinant Adeno-Associated Virus (AAV)-Based Random PPetide Display Library System: Infection-Defective AAV1.9-3. As a Novel Detargeted Platform for Vector Evolution", Gene Therapy and Regulation, Oct. 2010, vol. 5, No. 1, pp. 31-55.
NCBI, GenBank Accession No. AAS99264 Jun. 24, 2004.
NCBI, GenBank Accession No. YP_680426.1 Nov. 19, 2010.
Written Opinion issued in PCT/US2013/040415 on Sep. 25, 2013.
Adachi et al. "Creation of a Novel AAV2 vector showing AAV9-like Transduction Properties by displaying a Galactose binding motif on the capsid." Final Program Addendum. American Society of Gene & Cell Therapy, 15th Annual Meeting, May 16-19, 2012, Philadelphia, USA. May 3, 2012. pp. 34-35. Retrieved from: http://www.asgct.org/UserFiles/file/Addendum-Complete.pdf [Retrieved on Nov. 4, 2015].
Adachi et al. "Drawing a high-resolution functional map of adeno-associated virus capsid by massively parallel sequencing." Nature Communications. Jan. 1, 2014. p. 3075. Retrieved from: http://www.nature.com/ncomms/2014/140117/ncomms4075/pdf/ncomms4075.pdf [retrieved on Nov. 6, 2015] DOI: 10.1038/ncomms4075.
Bell et al. "Identification of the Galatose Binding Domain of the Adeno-Associated Virus Serotype 9 Capsid." Journal of Virology. Apr. 18, 2012. pp. 7326-7333. vol. 86, No. 13. DOI:10.1128/JVI.00448-12.
Partial European Search Report dated Dec. 4, 2015 as received in EP 13788512.5.
Pulicherla et al. "Engineering Liver-detargeted AAV9 Vectors for Cardiac and Musculoskeletal Gene Transfer." Molecular Therapy. Nature Publishing Group. Jun. 1, 2011. pp. 1070-1078. vol. 19, No. 6. Retrieved from http://www.nature.com/mt/journal/v19/n6/pdf/mt20112a.pdf [retrieved on Mar. 1, 2011]. DOI: 10.1038/MT.2011.22.
Qiao et al. "Single Tyrosine Mutation in AAV8 and AAV9 Capsids is Insufficient to Enhance Gene Delivery to Skeletal Muscle and Heart." Human Gene Therapy Methods. Feb. 1, 2012. pp. 29-37. vol. 23, No. 1. DOI: 10.1089/hgtb.2011.229.

* cited by examiner

```
                    484              500         514
      AAV9:  · ·SVAGPSNMAVQG· ·EFAW· ·RNSL· ·
                    483              499         513
  AAV2R585E:  · ·SQAGASDIRDQS· ·EYSW· ·RDSL· ·
AAV2R585E.9-1:  · ·SQAGASDIRDQS· ·EFAW· ·RNSL· ·
AAV2R585E.9-2:  · ·SVAGPSNMAVQG· ·EFAW· ·RNSL· ·
AAV2R585E.9-3:  · ·SVAGPSNMAVQG· ·EYSW· ·RDSL· ·
AAV2R585E.9-4:  · ·SQAGPSNMRDQS· ·EYSW· ·RDSL· ·
AAV2R585E.9-5:  · ·SQAGPSNMAVQS· ·EYSW· ·RDSL· ·
```
Figure 14A
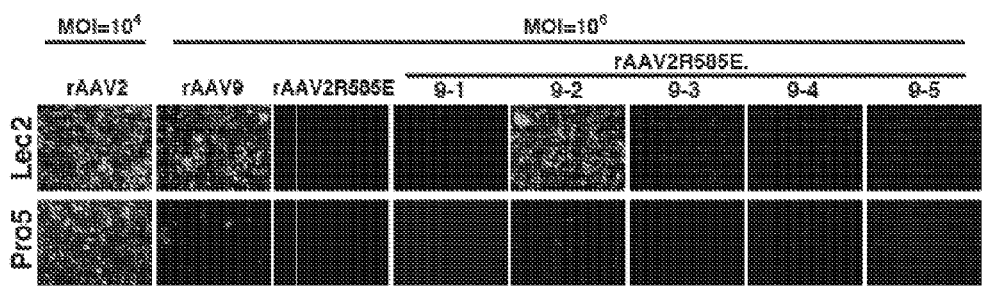
Figure 14B
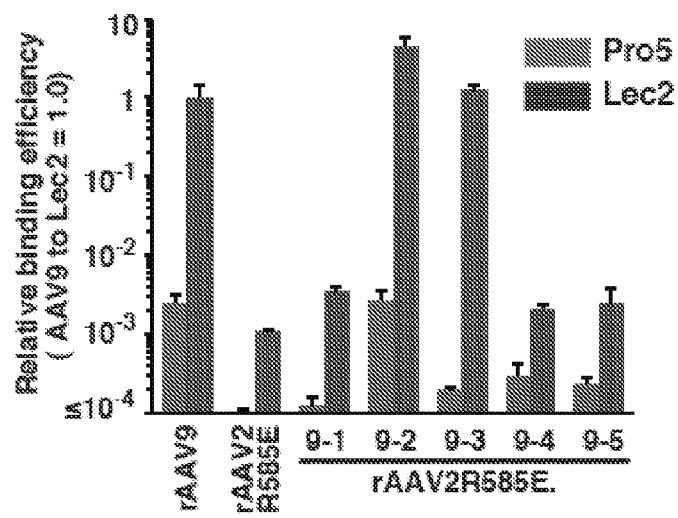
Figure 14C

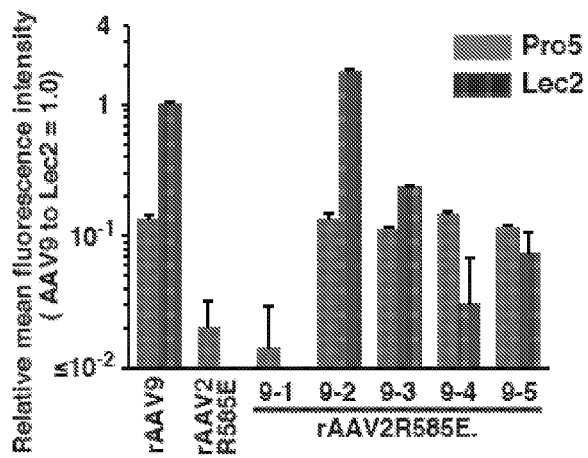

Figure 14D

··SVAGPSNMAVQG···· EFAW ··RNSL··

Binding                Transduction
(galactose)

Figure 14E

| | | Lec2 transduction efficienc (AAV2R585E = 1.0) |
|---|---|---|
| AAV2R585E 459-00009: | ··SVAGASDIRDQS···EYSW··RDSL·· | 0.7 |
| AAV2R585E 461-00009: | ··SVAGASDIRDQS···EYSW··RDSL·· | 0.9 |
| AAV2R585E 463-00009: | ··SVAGPSDIRDQS···EYSW··RDSL·· | 1.7 |
| AAV2R585E 465-00009: | ··SQAGPSNMRDQS···EYSW··RDSL·· | 5.8 |
| AAV2R585E 467-00009: | ··SQAGPSNMAVQS···EYSW··RDSL·· | 5.9 |
| AAV2R585E 469-00009: | ··SQAGASNMAVQG···EYSW··RDSL·· | 5.9 |
| AAV2R585E 471-00009: | ··SQAGASDIAVQG···EYSW··RDSL·· | 0.7 |
| AAV2R585E 473-00009: | ··SQAGASDIAVQG···EYSW··RDSL·· | n.a. |

Figure 15

| Vector (CMV-LacZ) | Mouse (N=3), 1x10e12vg | | | |
| --- | --- | --- | --- | --- |
| | Liver | | Heart | |
| | Barcode | Quanti. | Barcode | Quanti. |
| AAV9 | 1.0 ± 0.5 | 1.0 ± 0.1 | 1.0 ± 0.9 | 1.0 ± 0.6 |
| Q590A | 0.04 ± 0.01 | 0.01 ± 0.001 | 0.7 ± 0.3 | 0.5 ± 0.2 |
| P504A/G505A | 0.02 ± 0.01 | 0.001 ± 0.0001 | 0.8 ± 0.7 | 0.9 ± 0.3 |

Figure 23

```
                                484           500  504       514              590
            AAV9: · · SVAGPSNMAVQG · · EFAWPGAS · · RNSL · · · · SAQAQAQ
                                463           499  503       513          585  589
        AAV2R585E: · · SQAGASDIRDQS · · EYSWTGAT · · RDSL · · · · EGNRQAA

AAV2R585E.9-2: · · SVAGPSNMAVQG · · EFAWTGAT · · RNSL · · · · EGNRQAA

AAV2R585E.9-2
      -T503A/G504A : · · SVAGPSNMAVQG · · EFAWAAAT · · RNSL · · · · EGNRQAA

AAV2R585E.9-2
         -Q589A    : · · SVAGPSNMAVQG · · EFAWTGAT · · RNSL · · · · EGNRAAA

AAV2R585E.9-2
 -T503A/G504A/Q589A : · · SVAGPSNMAVQG · · EFAWAAAT · · RNSL · · · · EGNRAAA
```

Figure 24

ADENO ASSOCIATED VIRUS PLASMIDS AND VECTORS

RELATED APPLICATION DATA

This application is a national stage entry under 35 U.S.C. §371 of International Application No. PCT/US2013/040415, titled ADENO ASSOCIATED VIRUS PLASMIDS AND VECTORS, filed May 9, 2013, which claims priority to U.S. Provisional Application No. 61/644,814, filed May 9, 2012, and U.S. Provisional Application No. 61/664,537, filed Jun. 26, 2012, all of which are hereby incorporated by reference in their entireties.

ACKNOWLEDGEMENT OF GOVERNMENT SUPPORT

This application was made with US Government support under grant number R01DK078388, awarded by the National Institutes of Health. The US Government has certain rights in this application.

TECHNICAL FIELD

Generally, the disclosure relates to adeno associated viruses used in gene delivery. More specifically, the disclosure relates to adeno associated viruses used in gene delivery to particular target tissues.

BACKGROUND

Recombinant adeno-associated viruses (rAAV) are promising vectors for in vivo gene delivery. A number of naturally occurring serotypes and subtypes have been isolated from human and non-human primate tissues (Gao G et al., J Virol 78, 6381-6388 (2004) and Gao G et al., Proc Natl Acad Sci USA 99, 11854-11859 (2002), both of which are incorporated by reference herein). Among the newly-identified adeno-associated virus (AAV) isolates, AAV serotype 8 (AAV8) and AAV serotype 9 (AAV9) have gained much attention because rAAV vectors derived from these two serotypes can transduce various organs including the liver, heart, skeletal muscles and central nervous system with high efficiency following systemic administration via the periphery (Foust K D et al., Nat Biotechnol 27, 59-65 (2009); Gao et al, 2004, supra; Ghosh A et al., Mol Ther 15, 750-755 (2007); Inagaki K et al, Mol Ther 14, 45-53 (2006); Nakai H et al., J Virol 79, 214-224 (2005); Pacak C A et al., Circ Res 99, e3-e9 (2006); Wang Z et al., Nat Biotechnol 23, 321-328 (2005); and Zhu T et al., Circulation 112, 2650-2659 (2005), all of which are incorporated by reference herein).

The robust transduction by rAAV8 and rAAV9 vectors has been presumed to be ascribed to strong tropism for these cell types, efficient cellular uptake of vectors, and/or rapid uncoating of virion shells in cells (Thomas C E et al., J Virol 78, 3110-3122 (2004), incorporated by reference herein). In addition, emergence of capsid-engineered rAAV with better performance has significantly broadened the utility of rAAV as a vector toolkit (Asokan A et al., Mol Ther, published in advance of press doi:10.1038/mt.2011.287 (2012), incorporated by reference herein). Proof-of-concept for rAAV-mediated gene therapy has been shown in many preclinical animal models of human diseases. Phase I/II clinical studies have been initiated or completed for genetic diseases including hemophilia B (Manno C S et al., Nat Med 12, 342-347 (2006) and Nathwani A C et al., N Engl J Med 365, 2357-2365 (2011), both of which are incorporated by reference herein); muscular dystrophy (Mendell J R et al., N Engl J Med 363, 1429-1437 (2011), incorporated by reference herein); cardiac failure (Jessup M et al., Circulation 124, 304-313 (2011), incorporated by reference herein); blinding retinopathy (Maguire A M et al., Lancet 374, 1597-1605 (2009), incorporated by reference herein); and α1 anti-trypsin deficiency (Flotte T R et al., Hum Gene Ther 22, 1239-1247 (2011), incorporated by reference herein), among others.

Although rAAV vectors have widely been used in preclinical animal studies and have been tested in clinical safety studies, the current rAAV-mediated gene delivery systems remain suboptimal for broader clinical applications. The sequence of an AAV viral capsid protein defines numerous features of a particular AAV vector. For example, the capsid protein affects capsid structure and assembly, interactions with AAV nonstructural proteins such as Rep and AAP proteins, interactions with host body fluids and extracellular matrix, clearance of the virus from the blood, vascular permeability, antigenicity, reactivity to neutralizing antibodies, tissue/organ/cell type tropism, efficiency of cell attachment and internalization, intracellular trafficking routes, virion uncoating rates, among others. Furthermore, the relationship between a given AAV capsid amino acid sequence and the characteristics of the rAAV vector are unpredictable. Therefore, new rAAV vectors with altered capsid proteins are needed in order to maximize the benefit of AAV based therapies.

SUMMARY

Disclosed herein are rAAV vectors comprising one or more mutations in the viral capsid. The AAVs comprising the mutations disclosed herein may have altered phenotypes relative to AAVs that do not comprise the mutations. Altered phenotypes that may result from viruses comprising the mutations include, but are not limited to tissue specific targeting and exclusion, enhanced viral transduction, enhanced viral yield, and lack of recognition by immune sera raised against unmutated viruses, etc.

In certain embodiments, the disclosed mutations include mutations at one or more of the following residues of SEQ ID NO: 1: L380, T381, L382, N383, I440, D441, Y446, L447, T450, I451, V465, P468, S469, N470, M471, Q474, G475, Y484, R485, E500, F501, W503, R514, N515, S516, or L517, whether alone or in combination with each other or any other mutation.

In certain embodiments, the disclosed mutations include mutations at one or more of the following residues of SEQ ID NO: 1: P504, G505, and Q590, whether alone or in combination with each other or any other mutation.

In particular embodiments, these mutations or combinations thereof may affect the ability of a viral vector comprising those mutations to bind to one or more tissues or to exclude binding to one or more tissues. In particular embodiments, these mutations exclude binding to the liver.

In other embodiments, the disclosed mutations also include mutations in the following residues of SEQ ID NO: 4: Q464, A467, D469, I470, R471, D472, S474, Y500, S501, and D514, whether alone or in combination with any other mutation.

In particular embodiments, these mutations or combinations thereof may affect the ability of a viral vector comprising those mutations to bind to a cell type—in particular, a cell type with a glycosylation site comprising a terminal galactose.

BRIEF DESCRIPTION OF THE FIGURES

FIG. 7A shows the results when the experiment is performed in duplicate. FIG. 7B shows the results when the experiment is performed in triplicate.

In FIG. 9A, recombinant adeno-associated virus serotype 1 (rAAV1), rAAV2, rAAV8 or rAAV9 vector expressing the lacZ gene were injected into mice via the tail vein in bolus at a dose of $1.0 \times 10^{13}$ vg/kg (n=3-7 per group). Concentrations of rAAV particles in the blood were plotted as a function of time after injection. The data was obtained as described in (Kotchey N M et al., 2011, below) using 20 mice. All concentrations were normalized to that of AAV9. In FIG. 9B, the barcoded AAV library ID 394 was administered and blood samples were collected in the same manner as described above and sequenced. The data were limited to those serotypes also assessed in FIG. 9A. FIG. 9C shows all the pharmacokinetic data obtainable in the experiment shown in FIG. 9B. For FIGS. 9B and 9C, n=2 mice. Vertical bars represent standard errors of the mean.

In FIG. 11B, it is assumed that AAV2 transduces Pro5 and Lec2 cells at the same rate (Bell C L et al, J Clin Invest 121, 2427-2435 (2011), incorporated by reference herein.

FIG. 14A depicts the amino acid sequences of the AAV2R585E.9-1, AAV2R585E.9-2, AAV2R585E.9-3, AAV2R585E.9-4, and AAV2R585E.9-5 capsids. The red residues are mutations introduced in the AAV2R585E capsid to create a portion of (9-1, 9-3, and 9-4) or the full (9-2) galactose binding motif identified using AAV Barcode-Seq analysis.

FIG. 14B depicts Lec2 and Pro5 cell transduction AAV-CMV-GFP vectors with AAV2R585E.9-1, 9-2, 9-3, 9-4, and 9-5 capsids. The negative control is a lysate of 293 cells transfected with a GFP-expressing plasmid.

FIG. 14C is a bar graph depicting the ability of each AAV vector to bind to Pro5 and Lec2 cells. 9-2 and 9-3 efficiently bind to Lec2 cells, indicating that they have the ability to bind to the AAV9 primary receptor, galactose.

FIG. 14D is a bar graph depicting the efficiency at which each AAV vector transduces Pro5 and Lec2 cells. 9-3 does not transduce Lec2 cells as efficiently as AAV9 or AAV9-2, though AAV9-3 does bind to galactose.

FIG. 14E is a graphic depicting the -EFAW-RNSL- motif (right half) is important for postattachment viral processing.

FIG. 15 depicts the Lec2 transduction efficiency of hexapeptide scan AAV2R585E mutants that carry a potion of the galactose binding motif described herein. n.a., not applicable due to insufficient production of intact viral particles.

FIG. 23 shows the vector genome copy numbers in tissues determined by Southern blot analysis. The values are normalized with the values observed in AAV9-transduced tissues.

FIG. 24 depicts the sequence of AAV2R585E.9-2-derived mutants comprising liver detargeting mutations AAV2R585E.9-2 T503A/G504A (mtTG), AAV2R585E.9-2 Q589A (mtQ), and AAV2R585E.9-2 T503A/G504A/Q589A (mtTGQ).

DETAILED DESCRIPTION

Figure 1:
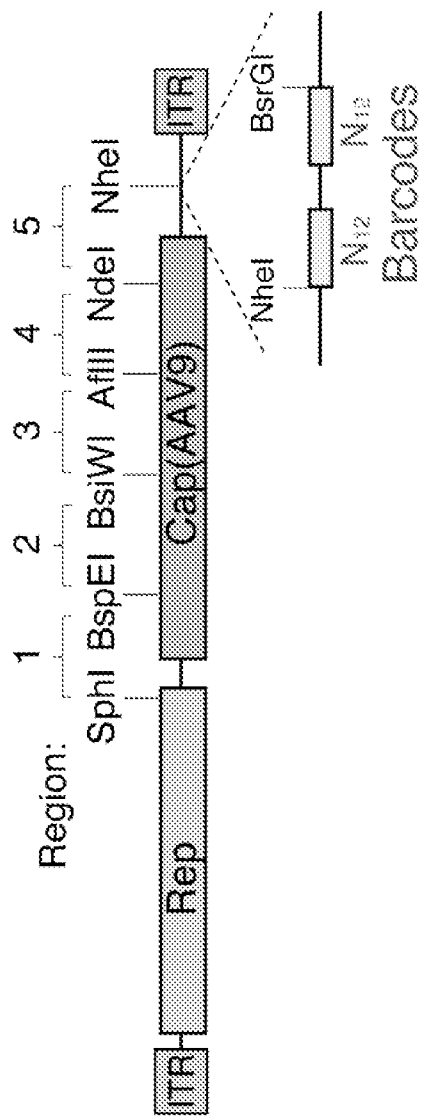
FIG. 1 is a viral genome map of AAV9-SBBANN2-BC. Two N12 barcodes (virus barcodes or VBCs) are inserted downstream of the poly A signal (pA). Each VBC can be PCR-amplified with the left or right VBC-specific set of primers. Unique restriction enzyme sites have been introduced for efficient cloning of PCR products with defined mutations.

The term "AAV vector" as used herein means any vector that comprises or derives from components of AAV and is suitable to infect mammalian cells, including human cells, of any of a number of tissue types, such as brain, heart, lung, skeletal muscle, liver, kidney, spleen, or pancreas, whether in vitro or in vivo. The term "AAV vector" may be used to refer to an AAV type viral particle (or virion) comprising at least a nucleic acid molecule encoding a protein of interest.

Additionally, the AAVs disclosed herein may be derived from various serotypes, including combinations of serotypes (e.g., "pseudotyped" AAV) or from various genomes (e.g., single-stranded or self-complementary). In particular embodiments, the AAV vectors disclosed herein may comprise desired proteins or protein variants. A "variant" as used herein, refers to an amino acid sequence that is altered by one or more amino acids. The variant may have "conservative" changes, wherein a substituted amino acid has similar structural or chemical properties, e.g., replacement of leucine with isoleucine. More rarely, a variant may have "nonconservative" changes, e.g., replacement of a glycine with a tryptophan. Analogous minor variations may also include amino acid deletions or insertions, or both. In certain embodiments, the AAV vectors disclosed herein may comprise a protein that differs by one or more amino acids from SEQ ID NO: 1 or SEQ ID NO: 4.

Nucleotide sequences, such as polynucleotides, encoding the proteins of the present disclosure are provided herein. The nucleotides of the present dislcosure can be composed of either RNA or DNA. The disclosure also encompasses those polynucleotides that are complementary in sequence to the polynucleotides disclosed herein.

Because of the degeneracy of the genetic code, a variety of different polynucleotide sequences can encode the proteins of the present disclosure. In addition, it is well within the skill of a person trained in the art to create alternative polynucleotide sequences encoding the same, or essentially the same, proteins disclosed herein. These variant or alternative polynucleotide sequences are within the scope of the current disclosure. As used herein, references to "essentially the same" sequence refers to sequences which encode amino acid substitutions, deletions, additions, or insertions which do not eliminate the detectability of the polypeptide encoded by the polynucleotides of the present disclosure.

The current disclosure also includes variants of the polynucleotides and polypeptides disclosed herein. Variant sequences include those sequences wherein one or more peptides or nucleotides of the sequence have been substituted, deleted, and/or inserted.

Polynucleotide and polypeptide sequences of the current disclosure can also be defined in terms of particular identity and/or similarity with certain polynucleotides and poypeptides described herein. The sequence identity will typically be greater than 60%, preferably greater than 75%, more preferably greater than 80%, even more preferably greater than 90%, and can be greater than 95%. The identity and/or similarity of a sequence can be 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% as compared to a sequence disclosed herein. Unless otherwise specified, as used herein percent sequence identity and/or similarity of two sequences can be determined using the algorithm of Karlin and Altschul (1990), modified as in Karlin and Altschul (1993). Such an algorithm is incorporated into the NBLAST and XBLAST programs of Altschul et al. (1990). BLAST searches can be performed with the NBLAST program, score=100, wordlength=12, to obtain sequences with the desired percent sequence identity. To obtain gapped alignments for comparison purposes, Gapped BLAST can be used as described in Altschul et al. (1997). When utilizing BLAST and Gapped BLAST programs, the default parameters of the respective programs (NBLAST and XBLAST) can be used.

Methods of producing AAV vectors as disclosed herein are well known in the art, including methods, for example, using packaging cells, auxiliary viruses or plasmids, and/or baculovirus systems (see, e.g., Samulski et al., J. Virology 63, 3822 (1989); Xiao et al., J. Virology 72, 2224 (1998); Inoue et al., J. Virol. 72, 7024 (1998); WO1998/022607; and WO2005/072364).

Methods of producing pseudotyped AAV vectors are also known (see, e.g., WO00/28004), as well as various modifications or formulations of AAV vectors, to reduce their immunogenicity upon in vivo administration (see, e.g., WO01/23001; WO00/73316; WO04/112727; WO05/ 005610; and WO99/06562). In some embodiments, AAV vectors may be prepared or derived from various serotypes of AAVs which may be mixed together or mixed with other types of viruses to produce chimeric (e.g., pseudotyped) AAV viruses.

In particular embodiments, the AAV vector may be a human serotype AAV vector. In such embodiments, a human AAV may be derived from any known serotype, e.g., from any one of serotypes 1-11, for instance from AAV1, AAV2, AAV4, AAV6, or AAV9. One specific, non-limiting example of such an AAV vector may include a vector comprising a nucleic acid molecule comprising an ITR and packaging sequence, operatively linked to a nucleic acid encoding an expression cassette for a protein of interest, and a nucleic acid encoding a protein of interest in an AAV9-derived capsid that differs from SEQ ID NO: 1 or SEQ ID NO: 4 by one or more amino acids.

In certain embodiments, the AAV vectors disclosed herein may comprise at least one mutation of one or more of the following residues in the amino acid sequence of its viral capsid: L380, T381, L382, N383, I440, D441, Y446, L447, T450, I451, V465, P468, S469, N470, M471, Q474, G475, Y484, R485, E500, F501, W503, P504, G505, R514, N515, S516, L517, and A590. For example, the AAV vectors disclosed herein may comprise at least one mutation selected from L380A, T381A, L382A, N383A, I440A, D441A, Y446A, L447A, T450A, I451A, V465A, P468A, S469A, N470A, M471A, Q474A, G475A, Y484A, R485A, E500A, F501A, W503A, P504A, G505A, R514A, N515A, S516A, L517A, and A590A. In further embodiments, the AAV vectors disclosed herein may comprise at least one double mutation selected from L380A/T381A, L382A/N383A, I440A/D441A, Y446A/L447A, T450A/I451A, P468A/S469A, N470A/M471A, Q474A/G475A, Y484A/R485A, E500A/F501A, R514A/N515A and S516A/L517A.

In particular embodiments, the AAV vectors disclosed herein may comprise at least one mutation of one or more of the following residues in the amino acid sequence of its viral capsid: Q464, A467, D469, I470, R471, D472, S474, Y500, S501, and D514. For example, the AAV vectors disclosed herein may comprise at least one mutation selected from Q464R, Q464V, A467P, D469G, D469T, I470M, R471A, R471S, D472V, D472E, D472N, S474P, S474A, S474G, Y500E, S501F, and D514R.

In some embodiments, the AAV vectors disclosed herein may comprise a polynucleotide that encodes a protein with an amino acid sequence selected from at least one of SEQ ID NO: 1, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16,SEQ ID NO: 18, SEQ ID NO: 19, SEQ ID NO: 20, SEQ ID NO: 21, SEQ ID NO: 23, SEQ ID NO: 24, and SEQ ID NO: 25, or fragments thereof.

The AAV vectors disclosed herein may include a nucleic acid encoding a protein of interest. In various embodiments, the nucleic acid also may include one or more regulatory sequences allowing expression and, in some embodiments, secretion of the protein of interest, such as e.g., a promoter, enhancer, polyadenylation signal, an internal ribosome entry site (IRES), a sequence encoding a protein transduction domain (PTD), and the like. Thus, in some embodiments, the nucleic acid may comprise a promoter region operably linked to the coding sequence to cause or improve expression of the protein of interest in infected cells. Such a promoter may be ubiquitous, cell- or tissue-specific, strong, weak, regulated, chimeric, etc., for example to allow efficient and stable production of the protein in the infected tissue. The promoter may be homologous to the encoded protein, or heterologous, although generally promoters of use in the disclosed methods are functional in human cells. Examples of regulated promoters include, without limitation, Tet on/off element-containing promoters, rapamycin-inducible promoters, tamoxifen-inducible promoters, and metallothionein promoters. Other promoters that may be used include promoters that are tissue specific for tissues such as kidney, spleen, and pancreas. Examples of ubiquitous promoters include viral promoters, particularly the CMV promoter, the RSV promoter, the SV40 promoter, etc., and cellular promoters such as the PGK (phosphoglycerate kinase) promoter and the β-actin promoter.

In some embodiments of the AAV vectors disclosed herein, one or more feedback elements may be used to dampen over-expression of the protein of interest. For example, some embodiments of the AAV vectors may include one or more siRNA sequences that would target the exogenous transcript. In other embodiments, the AAV vector may include one or more additional promoters that may be recognized by inhibitory transcription factors. In various embodiments, the AAV vectors disclosed herein may comprise a construct that may create a homoeostatic feedback loop that may maintain expression levels of the protein of interest at a physiological level.

In various embodiments, the AAV vectors disclosed herein can comprise a nucleic acid that may include a leader sequence allowing secretion of the encoded protein. In some embodiments, fusion of the transgene of interest with a sequence encoding a secretion signal peptide (usually located at the N-terminal of secreted polypeptides) may allow the production of the therapeutic protein in a form that can be secreted from the transduced cell. Examples of such signal peptides include the albumin, the β-glucuronidase, the alkaline protease or the fibronectin secretory signal peptides.

As described herein, effective and long term expression of therapeutic proteins of interest in brain, heart, lung, skeletal muscle, kidney, spleen, or pancreas may be achieved with non-invasive techniques, through peripheral administration of certain AAV vectors, such as an AAV9 vector or an AAV2 vector. Such peripheral administration may include any administration route that does not necessitate direct injection into brain, heart, lung, skeletal muscle, kidney, spleen, or pancreas. More particularly, peripheral administration may include systemic injections, such as intramuscular, intravenous, intraperitoneal, intra-arterial, or subcutaneous injections. In some embodiments, peripheral administration also may include oral administration (see, for instance, WO96/40954), delivery using implants, (see, for instance, WO01/91803), or administration by instillation through the respiratory system, e.g., using sprays, aerosols or any other appropriate formulations.

In various embodiments, the desired doses of the AAV vectors may be easily adapted by the skilled artisan, e.g., depending on the disease condition, the subject, the treatment schedule, etc. In some embodiments, from $10^5$ to $10^{12}$ viral genomes are administered per dose, for example, from $10^6$ to $10^{11}$, from $10^7$ to $10^{11}$, or from $10^8$ to $10^{11}$. In other embodiments, exemplary doses for achieving therapeutic effects may include virus titers of at least about $10^5$, $10^6$, $10^7$, $10^8$, $10^9$, $10^{10}$ or $10^{11}$ viral genomes or more. Virus titer may also be expressed in terms of transducing units, which may be readily calculated by those of skill in the art.

In various embodiments, the AAV vectors disclosed herein may be administered in any suitable form, for instance, either as a liquid solution or suspension, as a solid form suitable for solution or suspension in liquid prior to injection, as a gel or as an emulsion. The vectors may be formulated with any appropriate and pharmaceutically acceptable excipient, carrier, adjuvant, diluent, etc. For instance, for injection, a suitable carrier or diluent may be an isotonic solution, a buffer, sterile and pyrogen-free water, or, for instance, a sterile and pyrogen-free phosphate-buffered saline solution. For inhalation, the carrier may be in particulate form.

The vectors may be administered in a "therapeutically-effective" amount, e.g., an amount that is sufficient to alleviate (e.g., decrease, reduce) at least one of the symptoms associated with a disease state, or to provide improvement in the condition of the subject. In some embodiments, repeated administrations may be performed, for instance using either the same or a different peripheral administration route and/or the same vector or a distinct vector such as a different mutant form of AAV9 or AAV2.

Sequences

SEQ ID NO: 1 is the amino acid sequence of the unmutated AAV9 capsid.

SEQ ID NO: 2 is the nucleic acid sequence of the unmutated AAV9 capsid.

SEQ ID NO: 3 is the nucleic acid sequence of the pAAV9-SBBANN2-BC plasmid.

SEQ ID NO: 4 is the amino acid sequence of the unmutated AAV2 capsid.

SEQ ID NO: 5 is the amino acid sequence of mutant AAVR585E-465-16000.

SEQ ID NO: 6 is the amino acid sequence of mutant AAVR585E-465-00700.

SEQ ID NO: 7 is the amino acid sequence of mutant AAVR585E-465-00080.

SEQ ID NO: 8 is the amino acid sequence of mutant AAVR585E-465-00009.

SEQ ID NO: 9 is the amino acid sequence of mutant AAVR585E-467-16000.

SEQ ID NO: 10 is the amino acid sequence of mutant AAVR585E-467-00080.

SEQ ID NO: 11 is the amino acid sequence of mutant AAVR585E-467-00009.

SEQ ID NO: 12 is the amino acid sequence of mutant AAVR585E-469-00080.

SEQ ID NO: 13 is the amino acid sequence of mutant AAVR585E-469-00009.

SEQ ID NO: 14 is the amino acid sequence of mutant AAV2R585E.9-1.

SEQ ID NO: 15 is the amino acid sequence of mutant AAV2R585E.9-2.

SEQ ID NO: 16 is the amino acid sequence of mutant AAV2R585E.9-3.

SEQ ID NO: 17 is the nucleotide sequence of pUC118-AAV2R585E-SBBXEB-PBS.

SEQ ID NO: 18 is the amino acid sequence of mutant AAV2R585E.9-4

SEQ ID NO: 19 is the amino acid sequence of mutant AAV2R585E.9-5.

SEQ ID NO: 20 is the amino acid sequence of a P504A/G505A double mutant.

SEQ ID NO: 21 is the amino acid sequence of a Q590A mutant.

SEQ ID NO: 22 is the nucleotide sequence of the pHLP22-R585E.92 plasmid.

SEQ ID NO: 23 is the amino acid sequence of AAV2R585E.9-2 T503A/G504A double mutant, SEQ ID NO: 24 is the amino acid sequence of AAV2R585E.9-2 Q589A mutant.

SEQ ID NO: 25 is the amino acid sequence of AAV2R585E.9-2 T503A/G504A/Q589A triple mutant.

EXAMPLES

The following examples are illustrative of disclosed methods. In light of this disclosure, those of skill in the art will recognize that variations of these examples and other examples of the disclosed method would be possible without undue experimentation.

Example 1

AAV Barcode-Seq pAAV9-SBBANN2-BC is a wild-type AAV plasmid designed to facilitate high-throughput site directed mutagenesis of the AAV9 capsid. The parental plasmids used to synthesize pAAV9-SBBANN2-BC were the wild-type AAV2 plasmid pUC620 (Avigen Inc.) and the AAV9 helper plasmid p5E18-VD2/9 (Gao et al. 2004, supra).

The pAAV9-SBBANN2-BC plasmid was synthesized as follows:

The AAV2 capsid gene in pUC620 was replaced with the AAV9 cap gene from p5E18-VD2/9 (SEQ ID NO: 2). A Bgl II site was also introduced downstream of the capsid gene open reading frame (ORF). Additionally, a silent mutation was introduced in the AAV2 rep gene to create a new Sph I site. Also, silent mutations were introduced within the AAV9 cap gene to create new BspEI, Afl II and Nde I sites for convenient molecular cloning of AAV9 capsid mutants. Finally, a cassette comprising a set of two 12-nucleotide virus DNA barcodes (VBCs), three primer binding sites to efficiently PCR-amplify the VBCs, and a probe sequence that facilitates quantitative PCR, was subcloned 3' of the polyadenylation signal of the AAV genome (FIG. 1).

A DNA-barcoded pAAV9-SBBANN2-BC based plasmid library was created by inserting double stranded oligonucleotides with random sequences between the NheI and BsrGI restriction sites in pAAV9-SBBANN2-BC. The libraries were then used as platforms to creating DNA-barcoded capsid mutant AAV plasmid libraries. A pAAV9-SBBANN2-BC based library could include as many as 7×10$^6$ individual plasmids.

Figure 3:
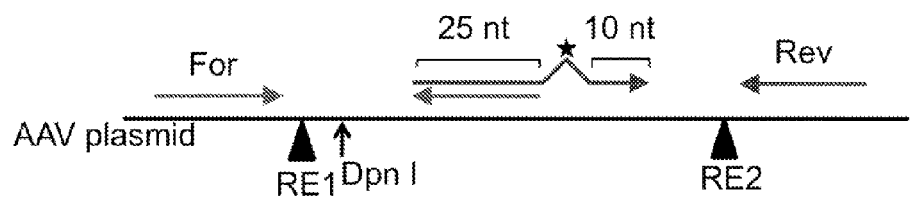
FIG. 3 is a representation of the bridging PCR strategy to introduce defined mutations into the AAV9 capsid protein in AAV9-SBBANN2-BC.

DNA-barcoded pAAV9-SBBANN2-BC plasmid constructs with double alanine mutations at defined locations were synthesized. A bridging PCR technique illustrated in FIG. 3 is used to introduce a double alanine mutation at a defined location in the AAV9 capsid protein (SEQ ID NO: 1). Referring now to FIG. 3, left and right side DNA fragments are individually amplified by corresponding PCR primer sets and are treated with Dpn I. The amplified fragments are then used as a template for a bridging PCR reaction. The asterisk in the figure indicates a mutation to be introduced. The amplified fragments are then cut with restriction enzymes that cut at the sites indicated by RE1 and RE2. The amplified and restricted fragments are then inserted into the corresponding restriction enzyme sites of pAAV9-SBBANN2-BC. Mutagenesis is performed using a PCR primer comprising a GCTGCT sequence that is used to introduce two consecutive alanine mutations into the capsid protein.

Plasmid libraries were created by mixing on the order of 10 products of the bridged PCR reaction, adding them to a single plasmid cut at the corresponding restriction sites, and ligating them into the plasmid. Confirmation of incorporation of the plasmid insert and/or the presence of the desired mutation was performed by DNA sequencing and by restriction enzyme digestion followed by gel electrophoresis of DNA.

Figure 2:
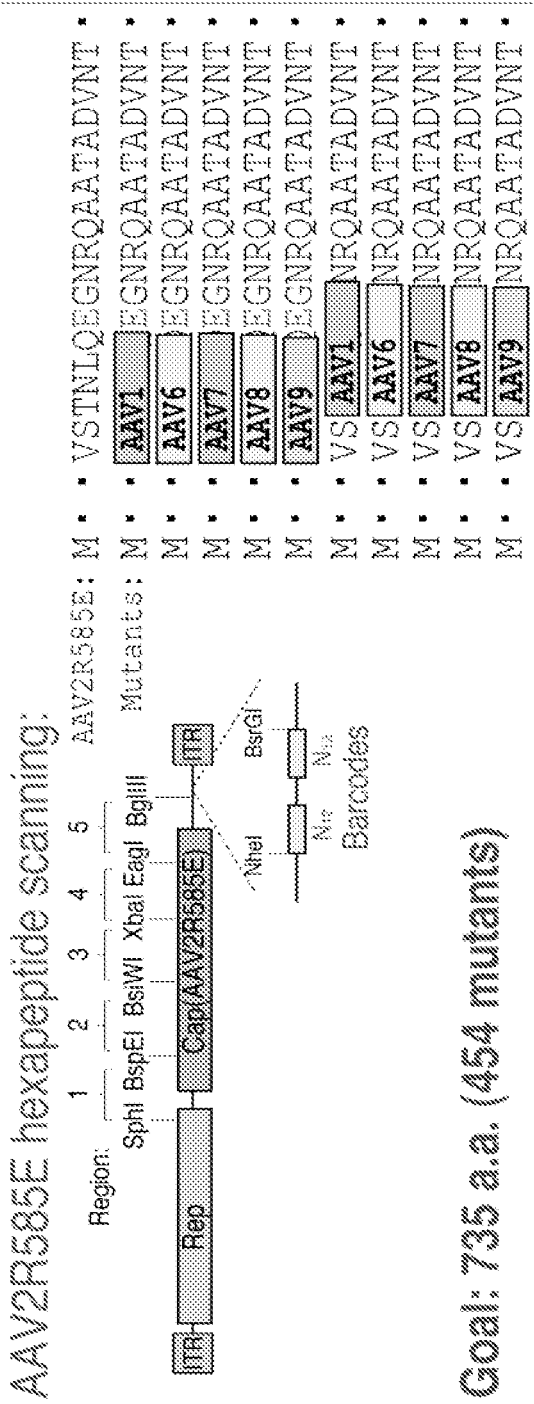
FIG. 2 is a viral genome map of AAV2R585E-SBBXEB-BC. Two N12 barcodes (virus barcodes or VBCs) are inserted downstream of the poly A signal (pA). Each VBC can be PCR-amplified with the left or right VBC-specific set of primers. Unique restriction enzyme sites have been introduced for efficient cloning of PCR products with defined mutations.

FIG. 2 is a viral genome map of AAV2R585E-SBBXEB-BC. AAV2R585E-SBBXEB-BC can be produced in HEK293 cells using the plasmid pAAV2R585E-SBBXEB-BC, which is a derivative of pUC118-AAV2R585E-SB-BXEB-PBS (SEQ ID NO: 17). The following changes were made to pUC118-AAV2R585E-SBBXEB-PBS to create pAAV2R585E-SBBXEB-BC: a Bgl II site was introduced downstream of the cap gene open reading frame (ORF); an R585E mutation was introduced in the AAV2 cap gene to ablate AAV2's heparin binding ability; a silent mutation was introduced in the AAV2 rep gene to create an Sph I site; silent mutations were introduced within the AAV2 cap gene to create new BspEI, Xba I and Eag I sites for convenient molecular cloning of AAV2 capsid mutants; silent mutations were introduced within the AAV2 cap gene to create new Dpn I sites at two locations to facilitate molecular cloning of AAV2 capsid mutants; and a cassette containing a set of two 12-nucleotide virus DNA barcodes (VBC), 3 primer binding sites to PCR-amplify VBCs, and a target sequence of qPCR, was placed downstream of the polyadenylation signal of the AAV genome.

A DNA-barcoded pAAV2R585E-SBBXEB-BC plasmid library was created by inserting double stranded oligonucleotides with random sequences between the NheI and BsrGI restriction sites in pAAV2R585E-SBBXEB-BC, as described above. The library was then used as a platform to create DNA-barcoded capsid mutant AAV plasmid libraries. A pAAV2R585E-SBBXEB-BC library could include as many as 6×10$^6$ individual plasmids. Such a library was synthesized with hexapeptide replacement mutations at defined locations (FIG. 2, right panel.)

From the plasmids, DNA-barcoded AAV virus libraries were then produced. AAV production and purification is as described in Grimm D et al., Blood 102, 2412-2419 (2003), which is incorporated by reference herein, except that AAV helper plasmid is not used at the AAV production. This is due to the AAVs in the library carrying both the rep and cap genes. Therefore AAV helper plasmid is not required to produce virus from the library plasmid. Each library may contain hundreds of different AAV capsid mutants, each of which has a unique set of DNA barcodes in its viral genome.

When an AAV library is produced using a plasmid DNA pool that contains multiple different mutant plasmids, genotype-phenotype dissociation or capsid mosaicism may occur where a viral genome may not necessarily code the capsid protein of the virion (Muller O J et al., Nat Biotechnol 21, 1040-1046 (2003), incorporated by reference herein). To preclude this possibility, each AAV clone of the controls and mutants are produced individually and then mixed after the completion of the virus production. Then the viral clone pool is purified according to the procedure described in Grimm, et al., 2003, supra.

Figure 4:
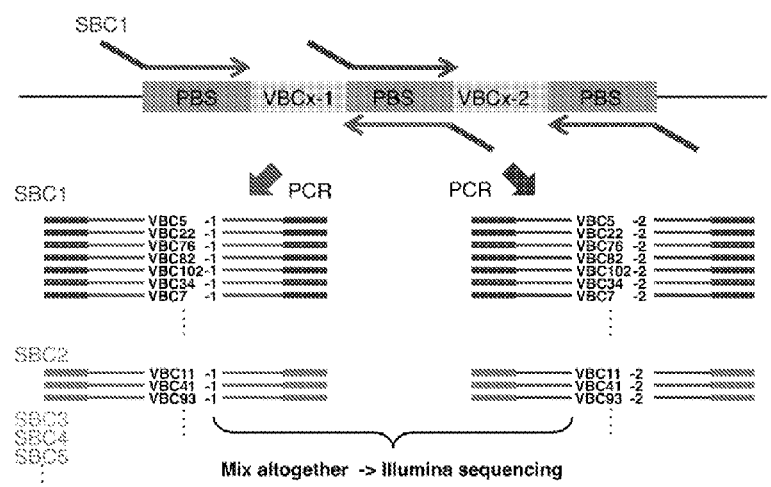
FIG. 4 is a representation of the AAV Barcode-Seq Procedure disclosed herein. VBC-1 and VBC-2 are individually amplified from a sample using primers that are adjacent to a sample specific barcode (SBC). 6VBC-1 and VBC-2 may be any of hundreds of different VBCs (e.g., VBC1-1, VBC2-1, VBC3-1 and so on as depicted in the figure). SBC-indexed VBC-1 and VBC-2 PCR products from all the samples are mixed together and subjected to Illumina sequencing to profile a total set of barcodes in a sample. By profiling the total set of barcodes, the viral genomes of each mutant may be quantified in the sample.

FIG. 4 outlines the AAV Barcode-Seq analysis. AAV viral genomes were extracted from samples of interest. The AAV viral genomes in this case were those derived from various AAV clones present in a library. The viral genome of each AAV clone has a clone-specific set of two viral DNA barcodes (shown as VBCx-1 and VBCx-2 in FIG. 4, wherein x represents the clone number). All the VBCx-1s and VBCx-2s present in a sample can be PCR amplified with VBC-1- and VBC-2-specific primer sets, respectively. Each primer is tagged with sample-specific barcode (SBC) for multi-sample indexing for Illumina sequencing. The SBCs used were 5-nucleotide-long SBCs previously reported by Craig et al. (Craig D W et al., Nat Methods 5, 887-893 (2008), incorporated by reference herein). However, longer or shorter barcodes may be used. The maximum number of SBC-indexed PCR products used per lane in Illumina sequencing was 96 (48 SBCs×2 VBCs). Once all the VBC-1 and VBC-2 PCR products from all the samples of interest were obtained, they were mixed together, and subjected to Illumina sequencing. Although a low sequence diversity of PCR products in reference image construction (Bentley D R et al., Nature 456, 53-59 (2008), incorporated by reference herein) may occur in while using Illumina sequencing of PCR products, the use of frame shifting primers, overcame this potential problem.

Illumina sequencing was performed using an Illumina GAIIx or HiSeq2000 generating approximately 10-100 million reads per lane. Sequencing reads were sorted according to SBCs and VBCs by an algorithm implemented in Perl.

Example 2

Using AAV Barcode-Seq to Quantify AAV Genomes in a Sample

AAV Barcode-Seq faces particular challenges in that a viral genome may account for only less than 0.0001% of DNA molecules in a sample. As a result, the viral genomes present in a sample are PCR-amplified prior to sequencing.

To address how accurately AAV Barcode-Seq could quantify viral genomes in a sample, three plasmid DNA pools were created. Each pool consisted of 100 pAAV9-SBBANN2-BC clones, and each clone had a unique VBC1 and VBC2. Pool 1 contained pAAV9-SBBANN2-BC clones at the same concentration, while pools 2 and 3 were a mixture of pAAV9-SBBANN2-BC clones at various but known concentrations that differed by a maximum of 10000 fold. In Pool 2, Clone No. 1 and Clone No. 100 were set at the lowest and highest concentrations, respectively, while in Pool 3, the concentrations of clone no. 1 and no. 100 were set as the highest and lowest concentrations, respectively. Using the three pools as PCR templates, VBC1 and VBC2 were amplified independently by 35 cycles of PCR with SBC-tagged primers. The PCR reactions were performed in quadruplicate and the resulting PCR products were sequenced.

Figure 5:
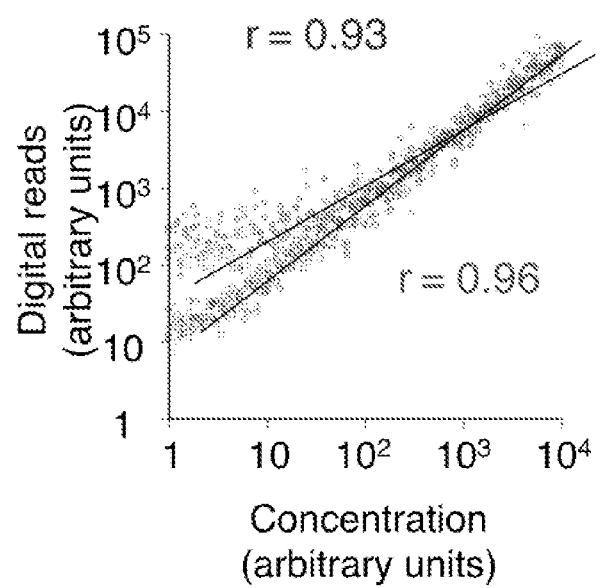
FIG. 5 is a scatter plot showing the relationship between the number of Illumina sequence reads and the concentration of DNA template in the AAV Barcode-Seq analysis. Digital sequence read numbers of 100 different DNA concentrations spread over a 4 log range were plotted against the plasmid DNA template concentrations. Normalization was done based on the observed small differences in PCR efficiencies between VBCs determined by a separate control experiment.

Sequence read numbers were obtained in a range from 400K-3M per one PCR product (that is, one SBC-indexed VBC1 or VBC2 PCR product). When using Pool 1, the averages of the coefficients of variation (a normalized measure of dispersion of the distribution) of the 100 VBC sequence read numbers in the quadruplicated PCR products were 0.63 and 0.57 for VBC1 and VBC2, respectively, while the averages of the coefficients of variation of the globally normalized sequence read numbers of the same VBC in the quadruplicated PCR products were 0.13 and 0.19 for VBC1 and VBC2. The relatively high coefficients of variation between VBCs indicate that PCR amplification efficiencies could vary to some degree depending on the sequence of VBCs. The small degree of dispersion among the normalized sequence read numbers for the same VBC in the four independent PCR reactions indicates high reproducibility. Pools 2 and 3 showed that the sequence read numbers are linearly correlated with the concentrations of each barcode in at least 3 log range with the Pearson's coefficients of 0.93 and 0.96 for VBC1 and VBC2, respectively, when the read numbers are globally normalized and corrected with relative PCR amplification efficiencies determined by the experiment using Pool 1 (see, FIG. 5).

In AAV Barcode-Seq, DNA-barcoded AAV libraries may contain reference AAV clones with wild type AAV9 capsid as well as the capsid from heparin binding mutant AAV2R585E in addition to mutant clones. Additionally, multiple clones per reference and/or multiple clones per mutant may be included in the libraries. Each of these multiple clones may differ in their individual VBC's such that two reference clones that are otherwise identical may have different VBC's.

Figure 6:
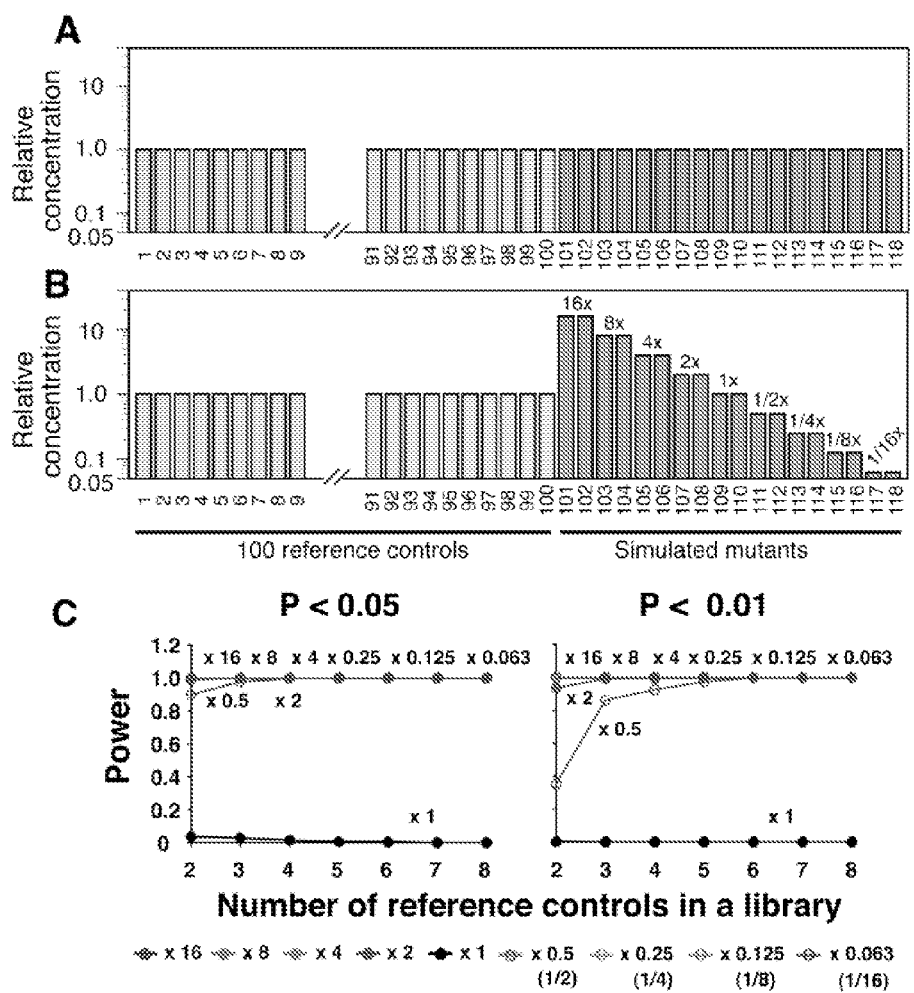
FIG. 6A and FIG. 6B each depict a Monte Carlo simulation study to assess the statistical power of the AAV Barcode-Seq analysis using two plasmid DNA libraries. The two libraries consisted of 118 pAAV9-SBBANN2-BC clones, each clone having a unique VBC1 and VBC2. The library in FIG. 6A mimics an AAV library stock and the library in FIG. 6B mimics a sample in which mutant clones are present in a range of concentrations.
In FIG. 6C, different numbers of reference controls in the library are randomly selected and compared to simulated mutants in duplicated experiments. The statistical comparison using a Mann Whitney U-test was done 500 times to determine the power of the analysis.

To investigate the sensitivity and power of the analysis, two plasmid DNA pools, each containing 118 pAAV9-SBBANN2-BC clones were generated. Each clone within the pool had a unique set of VBC1 and VBC2 (see, FIG. 6). One pool mimics viral genomes recovered from an AAV library stock in which reference controls and simulated mutants are mixed at an equimolar ratio (see, FIG. 6A). The second pool mimics viral genomes recovered from an experimental sample in which the mutant clones are at varying concentrations—for example, given two genomes having a representation in the pool at 1×, the remaining clones can be represented at 1/16×, 1/8×, 1/4×, 1/2×, 2×, 4×, 8× or 16×, with two genomes per concentration (see, FIG. 6B). The pools were analyzed using AAV-Barcode Seq. Monte Carlo simulation combined with Mann Whitney U-test indicated high sensitivity and power for the AAV-Barcode Seq (see, FIG. 6C).

Example 3

Using AAV Barcode-Seq to Examine Distribution of AAV Libraries In Vivo

Figure 7:
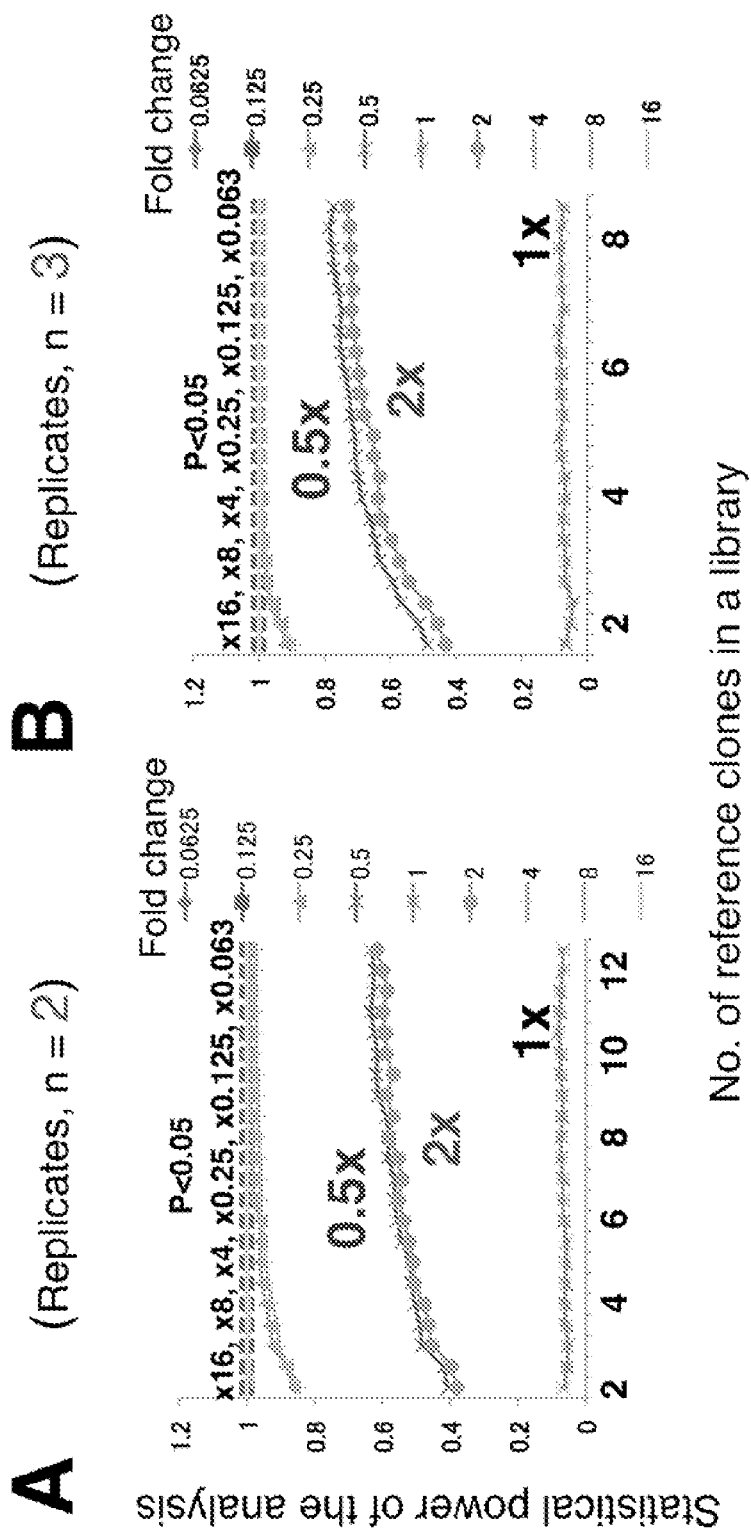
FIG. 7A and FIG. 7B each depict a Monte Carlo simulation study to assess the statistical power of the AAV Barcode-Seq analysis of AAV-transduced tissues. A DNA-barcoded AAV library consisting of 100 identical AAV9 clones, each with a pair of unique DNA barcodes, was intravenously administered into mice (n=2), and the liver tissues were harvested 11 days post injection. Total DNA was extracted from the samples and subjected to the AAV Barcode-Seq analysis. The data were used in a Monte Carlo simulation study.

AAV library 394 was injected in two mice, and the liver tissues were harvested 11 days post-injection. VBCs were PCR-amplified by PCR from total DNA extracted from the liver tissue and sequenced. The AAV library used (Library ID 394) consisted of a mixture of 100 AAV9 virus preparations that are genetically identical but were synthesized in separate culture dishes. Each of the 100 AAV9 clones can be individually identified because each has a clone-specific set of DNA barcodes incorporated in its viral genome. The composition of AAV9 is summarized in Table 1 below. Liver transduction efficiencies of each clone exhibited a coefficient of variation of 0.25 in one mouse and 0.42 in the other. When analyzed by a Monte Carlo simulation approach, a power of nearly 0.8 in detecting 2-fold differences (2 fold increase and decrease) with a p value of <0.05 was attainable by the inclusion of 8 or more reference clones in an AAV library (see, FIG. 7).

TABLE 1 composition of AAV library 394, total of 132 individually barcoded clones.

| Serotype | Description | Number of barcoded clones |
|---|---|---|
| AAV9 | Control | 100 |
| AAV2R585E | Control | 10 |
| AAV1 | Wild Type | 2 |
| AAV2 | Wild Type | 2 |
| AAV3 | Wild Type | 2 |
| AAV4 | Wild Type | 2 |
| AAV5 | Wild Type | 2 |
| AAV6 | Wild Type | 2 |
| AAV7 | Wild Type | 2 |
| AAV8 | Wild Type | 2 |

TABLE 1-continued composition of AAV library 394, total of 132 individually barcoded clones.

| Serotype | Description | Number of barcoded clones |
|---|---|---|
| AAVrh10 | Wild Type | 2 |
| AAV1&9 hybrid 1 | Wild type | 2 |
| AAV1&9 hybrid 2 | Wild type | 2 |

Example 4

Figure 8:
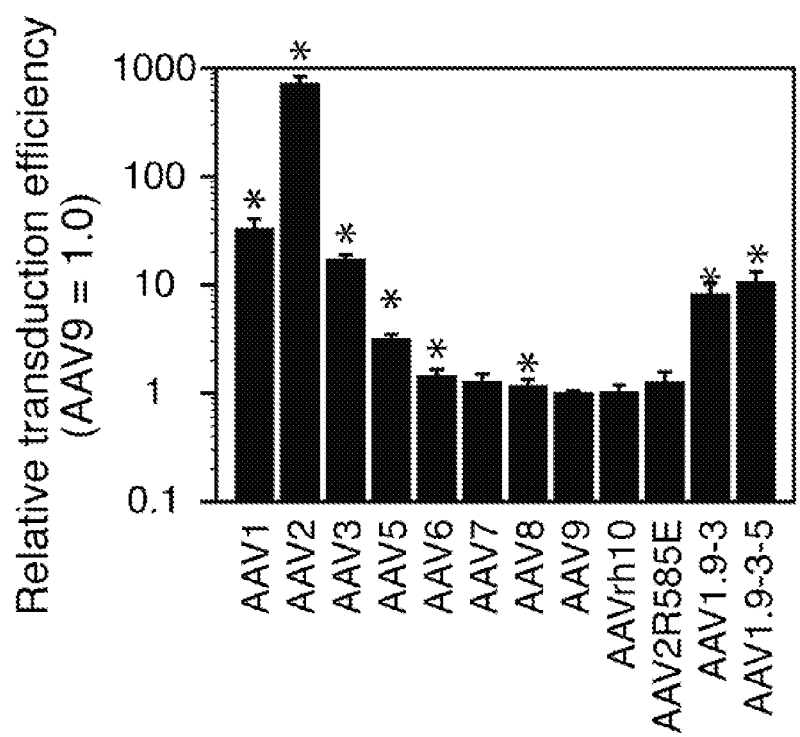
FIG. 8 depicts HEK 293 cell transduction efficiencies of various serotypes and variants. HEK 293 cells were infected with a DNA-barcoded AAV library containing 12 different AAV serotypes and variants. Transduction efficiencies were determined by AAV Barcode-Seq 48 hours post infection. The values are normalized by the transduction efficiency of AAV9. The experiment was done in triplicate. Vertical bars are SEMs.

Using AAV Barcode-Seq to Assess In Vitro Transduction Efficiency of AAV Variants A population of HEK 293 cells was infected with a DNA barcoded AAV library 394 at a multiplicity of infection (M01) of $10^5$. The library contained the indicated AAV serotypes and variants. Results are shown in FIG. 8.

Example 5

Using AAV Barcode-Seq to Assess Blood Clearance of AAV Variants

It has been reported that AAV9 exhibits distinctively delayed blood clearance compared to other serotypes when infused intravenously in mice. In addition, AAV1 is rapidly eliminated from the blood circulation and AAV2 is cleared very rapidly for the first 30 minutes following intravenous administration and slowly cleared thereafter (see, FIG. 9A and Kotchey N M et al., Mol Ther 19, 1079-1089 (2011), incorporated by reference herein).

Figure 9:
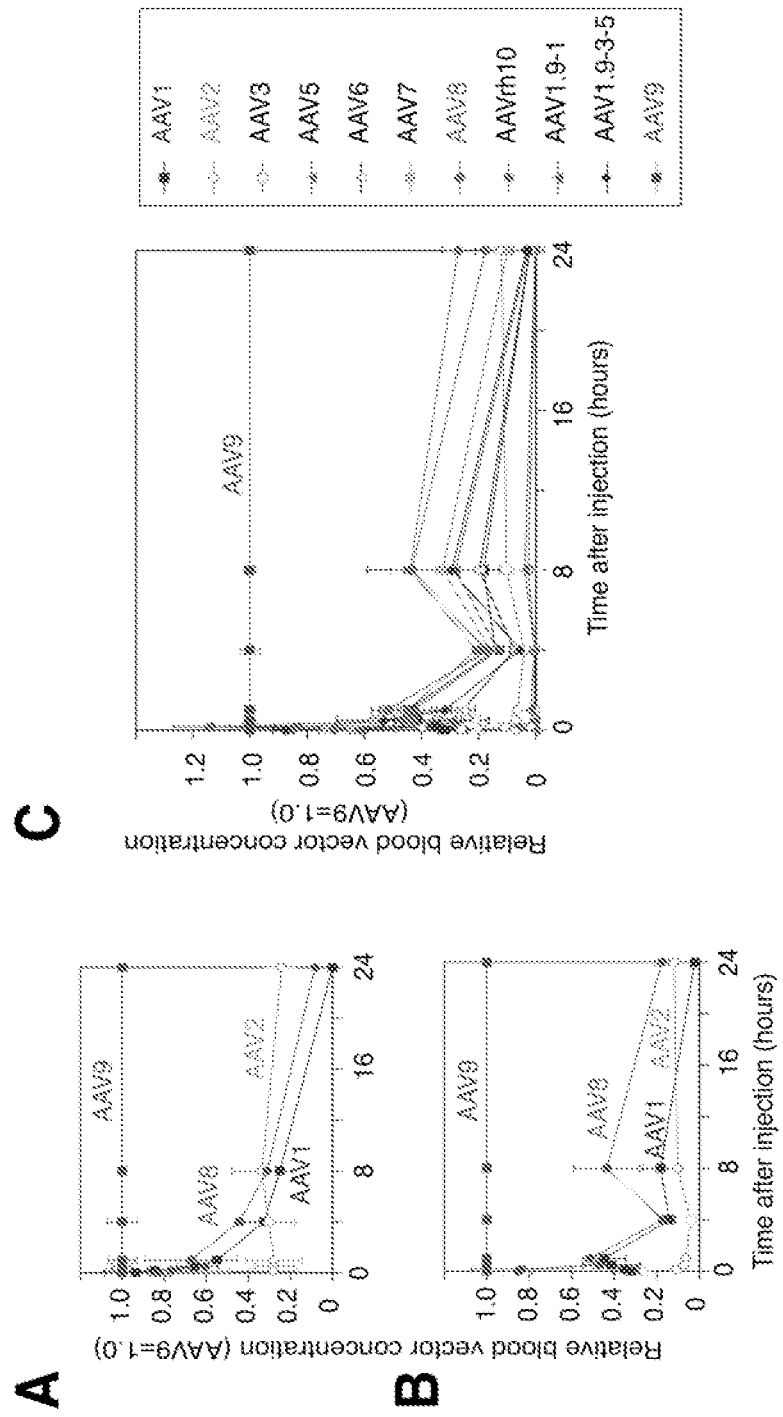
FIG. 9 depicts blood vector concentration-time curves following intravenous injection of various AAV serotypes or variants in mice.

In FIG. 9B, the same pharmacokinetic features were also observed using AAV Barcode-Seq. FIG. 9C shows that the results were observed after using only two mice. Without AAV Barcode-Seq, at least 33 mice and a significant amount of time would be required to obtain the same information.

Example 6

Figure 10:
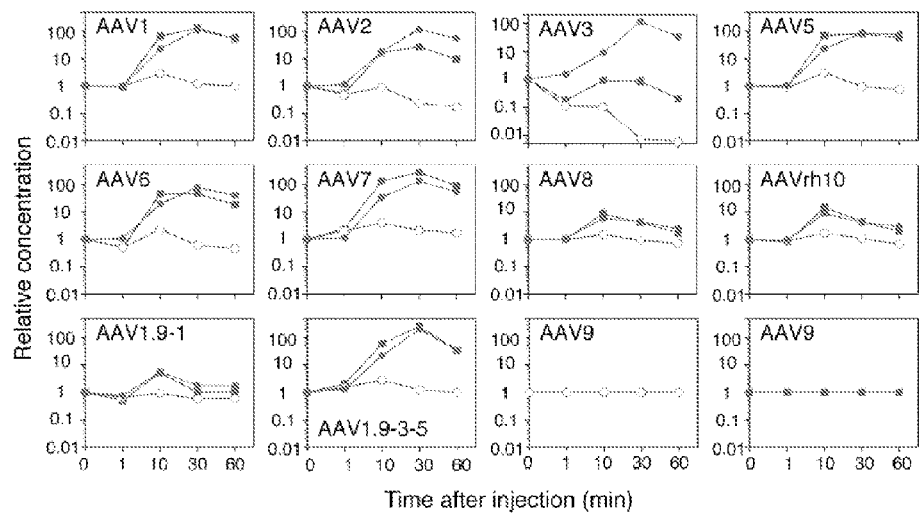
FIG. 10 is a set of graphs depicting the results of an analysis of the indicated serotypes for their reactivity to mouse anti-AAV9 neutralizing antibody as determined by AAV Barcode-Seq. Either naive or AAV9-preimmunized adult mice (n=2 each) were injected with the barcoded AAV library ID 394 via the tail vein, and blood samples were collected 1, 10, 30 and 60 min post injection. Then AAV genomes of each serotype in each sample were quantified by AAV Barcode-Seq. The blue and red lines show the blood vector concentrations relative to that of AAV9 (i.e., the relative concentrations) in naive mice and the anti-AAV9 antibody-harboring mice, respectively. Because AAV9 particles are quickly cleared from the blood circulation in AAV9 antibody-harboring mice, the relative blood concentrations of the AAV serotypes that are not neutralized with anti-AAV9 antibody exhibit a dramatic increase at 10 min and remain thereafter at a high level except for AAV3, which is cleared from the blood circulation very rapidly. In contrast, the AAV serotypes that are neutralized exhibit a pharmacokinetic property similar to that of AAV9. Green lines are ratios of the relative concentrations in the anti-AAV9 antibody-harboring mice to those in naive mice.
Figure 11:
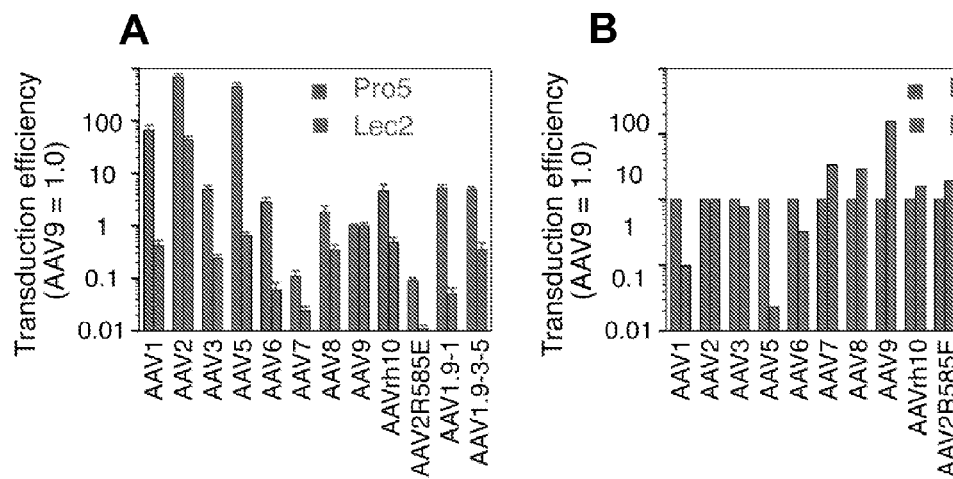
FIG. 11A and FIG. 11B depict the transduction efficiencies in CHO Pro5 and Lec2 cells with various AAV serotypes and variants determined by the AAV Barcode-Seq. CHO Pro5 and Lec2 cells were infected with DNA-barcoded various AAV serotypes and variants (AAV library ID 394). Forty-eight hours after infection, transduction efficiencies were determined by AAV Barcode-Seq. The results are normalized by the value of AAV9 (A) or AAV2 (B).
Figure 12:
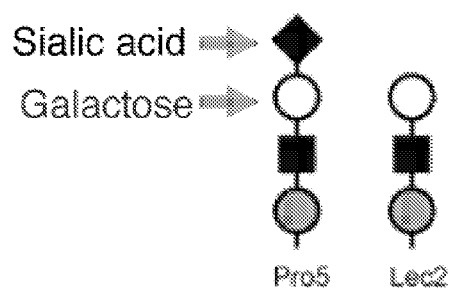
FIG. 12 is a graphical depiction of the cell surface glycans of CHO Pro5 and Lec2 cells. Terminal sialic acid serves as the receptor for AAV1, AAV5, and AAV6 while terminal galactose is the receptor for AAV9.

Using AAV Barcode-Seq to Assess Reactivity to Neutralizing Antibodies AAV Variants Reactivity to neutralizing antibodies against the AAV capsid was investigated by injecting intravenously the AAV library ID 394 (see, Table 2) into naive mice and mice that had been previously immunized with an intravenous injection of $1.0 \times 10^{11}$ vector genomes (vg) of AAV9-CMV-lacZ 3, or more, weeks prior to the intravenous infusion of AAV library ID 394. Blood concentrations of each AAV serotype or variant were then quantified by the AAV Barcode-Seq and normalized to the blood concentration of AAV9. Results are shown in FIG. 10.

It has been shown previously that the level of AAV neutralizing antibody in the blood circulation of mice previously immunized with AAV as described above is sufficient to eliminate a majority of infused AAV viral particles within 30 minutes (Kotchey N M et al., 2011, supra). In mice previously immunized with AAV9, the AAV9-normalized relative blood concentration of a serotype not recognized by anti-AAV9 antibodies would significantly increase for the first hour following AAV injection. The increase does not occur with a serotype that is recognized by anti-AAV9 antibodies. When the relative pharmacokinetic profiles of each serotype or variant were compared between the naive animals and AAV9 antibody-positive animals, a clear distinction was observed between the AAV serotypes or variants that are neutralized with anti-AAV9 antibody (i.e., AAV8, AAVrh10, and AAV1.9-1) and those that are not neutralized. This observation on the cross-reactivity of anti-AAV9 neutralizing antibody shows that the results from AAV Barcode-Seq recapitulate results obtained by other methods (Gao G et al., 2004, supra).

Example 7

Using AAV Barcode-Seq to Assess In Vivo Transduction of AAV Variants

Three mice were injected with AAV library ID 394 via the tail vain at a dose of $1.0 \times 10^{12}$ vg/mouse. Six to eight weeks post-injection, various tissues were harvested. Total DNA was extracted from each tissue sample and sequenced. AAV Barcode-Seq revealed that AAV8, AAV9 and AAVrh10, known to have high transduction efficiency also exhibit higher transduction efficiency compared to other serotypes in many tissues using AAV Barcode-Seq. Similarly, AAV3 is known to have poor transduction and that result is recapitulated using AAV Barcode-Seq.

Example 8

Mutations in AAV9 Capsid Assessed by AAV Barcode-Seq

The first atomic structure of an AAV determined was that of AAV2 in 2002 (Xie Q et al., Proc Natl Acad Sci USA 99, 10405-10410 (2002), incorporated by reference herein). Since then, the three dimensional structures of other serotypes, AAV1, AAV3, AAV4, AAV5, AAV6, AAV7, AAV8 and AAV9 have been determined completely or partially by X-ray crystallography and cryo-electron microscopy combined with image reconstruction (DiMattia M et al., Acta Crystallogr Sect F Struct Biol Cryst Commun 61, 917-921 (2005); Govindasamy L et al., J Virol 80, 11556-11570 (2006); Lerch T F et al., Virology 403, 26-36 (2010); Miller E B et al., Acta Crystallogr Sect F Struct Biol Cryst Commun 62, 1271-1274 (2006); Nam H et al., J Virol 81, 12260-12271 (2007); Padron E et al., J Virol 79, 5047-5058 (2005); Quesada O et al., Acta Crystallogr Sect F Struct Biol Cryst Commun 63, 1073-1076 (2007); Xie Q et al., Virology 420, 10-19 (2008), all of which are incorporated by reference herein).

The structures above have significantly advanced knowledge of AAV capsid structure-function relationships, and accelerated the research on AAV capsid engineering aimed at creating novel AAV capsids with better biological performance or altered tropism (Asokan A et al., 2012, supra, and Girod A et al., Nat Med 5, 1438 (1999), incorporated by reference herein). The main strategic paradigm in protein research is to obtain and use protein structural information to identify potential structural domains, predict their phenotypic roles, and then perform targeted mutagenesis on the structural domains to elucidate the phenotypes. Structural biology approaches provides a comprehensive picture of the whole protein or protein complex of interest and takes advantage of a wealth of structural information of various types of proteins to predict functions (Thornton J M et al, Nat Struct Biol 7, 991-994 (2000). That said, this approach may not be the most efficient way to interrogate the roles of structural domains of viral capsids. Phenotypic outcomes of capsids depend on their quaternary structure, and therefore, viral capsids are structurally, functionally and often coevolutionarily constrained in a manner specific to each viral species. As a result, it is difficult to understand functional roles and the significance of each amino acid or group thereof in a region of interest solely through structural studies without complementing data obtained by mutagenesis experiments. With regard to the AAV capsid it has been shown that only one or a few amino acid mutations can significantly change the phenotype of the viral capsid and that the correlation between a given mutation and the resulting phenotype is highly unpredictable (Excoffon K J et al., Proc Natl Acad Sci USA 106, 3865-3870 (2009); Pulicherla N et al., Mol Ther 19, 1070-1078 (2011); and Vandenberghe L H et al., Gene Ther 16, 1416-1428 (2009); all of which are incorporated by reference herein).

Example 9 pAAV2R585E-SBBXEB-BC Plasmid Hexapeptide Screen

An additional library is created using AAV Barcode SEQ comprising the pAAV2R585E-SBBXEB-BC plasmid construct in which a hexapeptide in the AAV2 capsid is replaced with the corresponding hexapeptide derived from AAV1, 6, 7, 8 or 9 capsid (FIG. 2). These plasmid constructs are used to produce AAV viral particles. With this set of AAV2R585E capsid mutants, functional significance of less-conserved short amino acid stretches of the AAV1, 6, 7, 8 and 9 capsid can be investigated. A bridging PCR technique is used to change a hexapeptide sequence from one to another at a defined location (FIG. 2)

Example 10

Identification of Mutations that Confer Binding of Terminal Galactose on AAV2

Recently, two research groups have identified terminal galactose on cell surface glycans as the primary receptor for AAV9 (Bell C L et al, J Clin Invest 121, 2427-2435 (2011) and Shen S et al, J Biol Chem 286, 13532-13540 (2011); both of which are incorporated by reference herein) using the CHO cell lines, Pro5 and Lec2. Lec2 is a derivative of Pro5 and lacks terminal sialic acid in its cell surface glycans due to a defect in cytidine monophosphate (CMP)—sialic acid transporter (Eckhardt M et al, J Biol Chem 273, 20189-20195 (1998); incorporated by reference herein). These studies demonstrate that surface binding and transduction efficiencies of AAV9 are much higher in Lec2 cells and neuraminidase-treated Pro5 cells relative to untreated Pro5 cells. The enhanced transduction of LecS is inhibited by cotreatment with galactose-binding lectins. Heparan sulfate proteoglycan is the primary receptor for AAV2, and its binding motif on the AAV2 capsid has been identified (Kern A et al, J Virol 77, 11072-11081 (2003) and Opie S R et al, J Virol 77, 6995-7006 (2003); both of which are incorporated by reference herein).

AAV9 double alanine mutant libraries IDs 401, 406 and 407 were used to investigate which amino acids are responsible for binding to terminal galactose, the AAV9's cell surface receptor. Cells were pre-cooled to 4° C., exposed to each of the libraries and incubated at 4° C. for one hour to allow viral particles bind to cell surface. The cell surface-bound AAV particles were recovered and subjected to the AAV Barcode-Seq analysis.

Mutants with the following sets of mutations: L380A/T381A, L382A/N383A, I440A/D441A, Y446A/L447A, T450A/I451A, V465A, P468A/S469A, N470A/M471A, Q474A/G475A, Y484A/R485A, E500A/F501A, W503A, R514A/N515A and S516A/L517A exhibited significant impairment of cell surface binding to Lec2 cells compared to the wild type (i.e., >78% decrease in cell surface binding, $p<0.05$).

To narrow down the amino acids that are most critical for galactose binding, the evolutionary conservation and topological location of each of the amino acids disclosed above. Those amino acids critical for galactose binding are those that are evolutionarily variable, surface exposed, and form a cluster on the surface of the capsid, and that such a set of such amino acids should be unique to AAV9.

Figure 22:
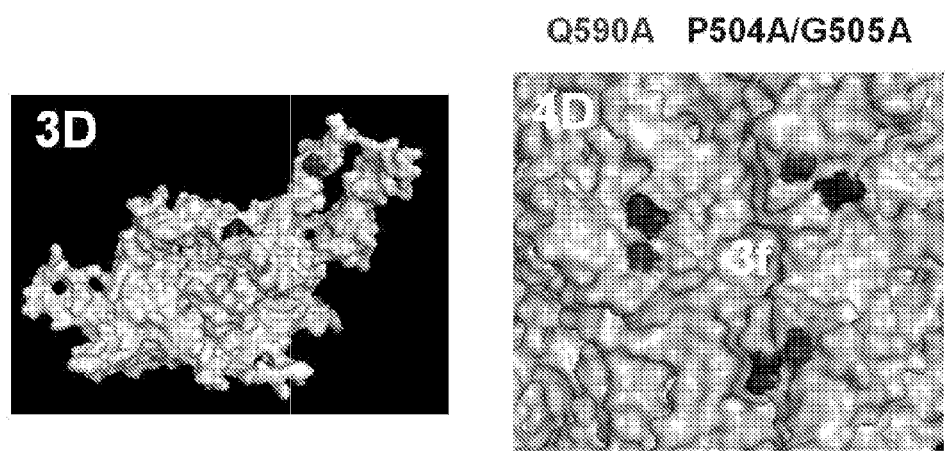
FIG. 22 is a representation of the topological location of P504/G505 (blue) and Q590 (red). Although they reside separately in primary structure and tertiary (3D) structure, they are located next to each other in the three-fold symmetry axis region in quaternary structure.

The amino acid sequences of AAV1, 2, 3, 6, 7, 8 and 9, which represent each of all the AAV clades (Gao, et al., 2004), were assessed for level of conservation across clades. Of the 26 amino acids described above, all but 12 were highly conserved across AAV1, 2, 3, 6, 7, 8 and 9. Those non-conserved amino acids were I451, V465, P468, S469, N470, M471, G475, Y484, E500, F501, N515 and L517. Of those 12 amino acids, 9 (I451, V465, P468, S469, N470, E500, F501, N515 and L517) are surface exposed, forming two subclusters on the surface of the capsid: I451, E500, F501, N515 and L517 form one subcluster and V465, P468, S469, and N470 form another subcluster. These two subclusters are bridged by surface-exposed Y446/L447, forming a larger cluster between the three prominent spikes around the 3-fold symmetry axis (FIG. 22). Because the double alanine mutation of Y446/L447, which are fully conserved in AAV1, 2, 3, 6, 7, 8 and 9, results in a dramatic decrease in the Lec2 cell binding ability, our observations indicates an important role of Y446/L447 in maintaining the function of the AAV9-specific motif for the binding to its cognate receptor.

Figure 13:
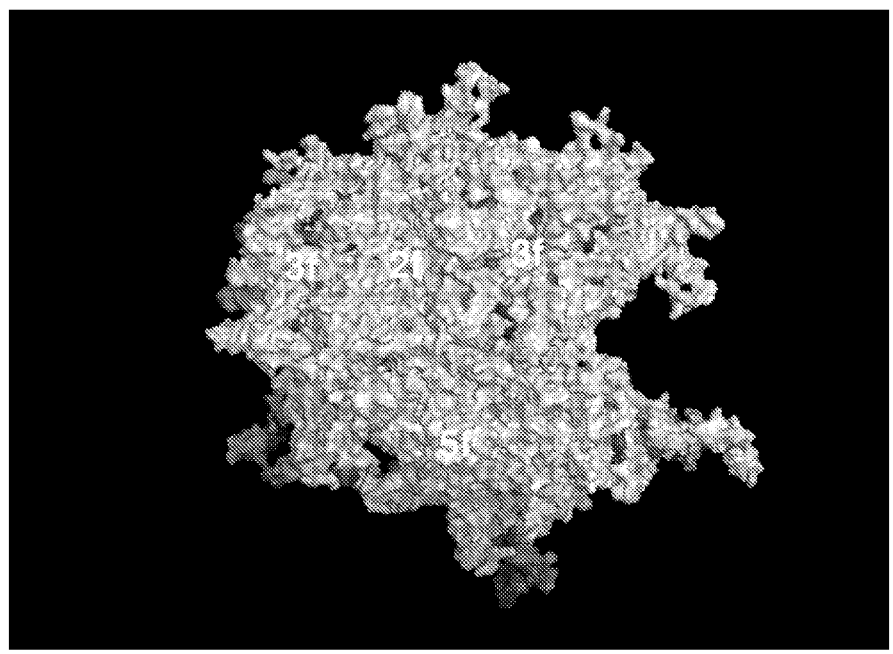
FIG. 13 is a model of the AAV9 capsid indicating the location of the amino acids shown to be important for binding to Lec2 cell surface receptor. Double alanine mutations of the colored amino acids result in significant impairment of the binding to Lec2 cell surface receptor. Red and blue amino acids are strictly conserved residues among AAV1, 2, 3, 6, 7, 8 and 9. The green (V465, P468, S469, and N470) and yellow (I451, E500, F501, N515 and L517) amino acids are variable among the serotypes and form 2 clusters, which are bridged by the strictly conserved Y446/L447 (blue), forming a larger cluster.

This concept is illustrated in FIG. 13, the nine amino acids listed from a cluster made up of two subclusters on the surface of the viral capsid protein. I451, E500, F501, N515, L517 are shown in medium grey, Y446 and L447 are shown in dark grey, and V465, P468, S469, and N470 are shown in light grey.

To further investigate the roles of the amino acids that were identified as those that play a role in the galactose binding, AAV2 capsid amino acids were mutated such that AAV2 capsid acquires the galactose binding motif. To this end, the AAV2R585E.9 series was created comprising AAV2R585E.9-1, AAV2R585E.9-2, AAV2R585E.9-3, AAV2R585E.9-4, and AAV2R585E.9-5 which are identified as SEQ ID NO: 14, SEQ ID NO: 15, SEQ ID NO: 16, SEQ ID NO: 18, and SEQ ID NO: 19 herein. The mutations in each relative to AAV2 and AAV9 are highlighted in FIG. 14A. As shown in FIGS. 14B, C, and D, AAV2R585E.9-2, transduced Lec2 cells at a level comparable to that of AAV9 and much higher than that of the parental AAV2R585E, while it transduces Pro5 cells at a low level similar to that of AAV2R585E or AAV9. FIGS. 14B, C, and D also show that AAV2R585E.9-1, which carries only Y500F/S501A/D514N mutations, AAV2R585E.9-3, which carries only Q464V/A476P/D469N/I470M/R471A/D472V/S474G mutations, AAV2R585E.9-4, which carries only A467P/D469N/I470M mutations, and AAV2R585E.9-5 which carries only A467P/D469N/I470M/R471A/D472V mutations did not transduce Lec2 cells as readily as AAV2R585E.9-2. This indicates that the right half of the motif -EFAW-RNSL- is important for post-attachment viral processing and is dispensable for galactose binding.

Figure 16A:
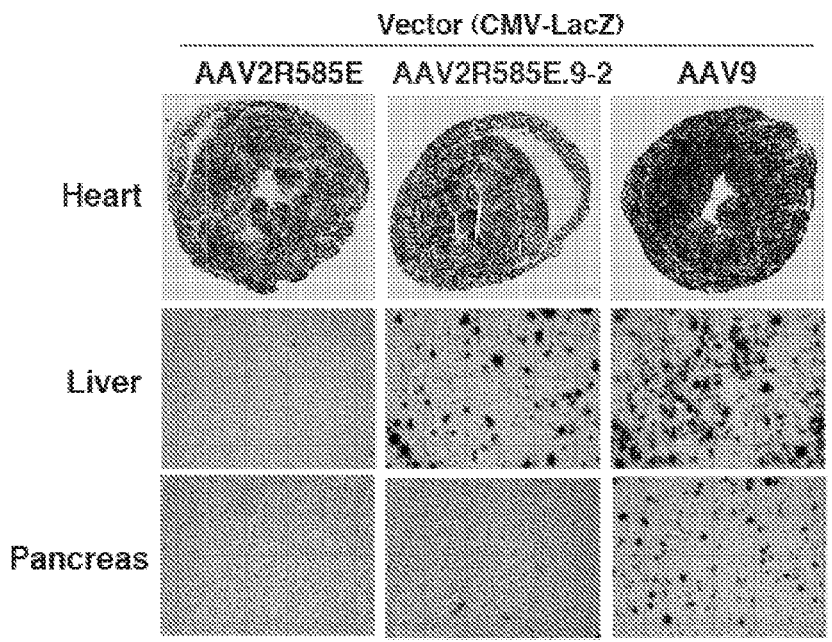
FIG. 16A is a set of images showing the in vivo transduction efficiency of 9-2. AAV-CMV-lacZ vector was packaged with AAV2R585E.9-2 capsid. This was injected into wild type C57Bl/6 Rag1−/− mice at a dose of 1×10$^{12}$ vector genomes per mouse. The images indicate that 9-2 can transduce the heart and liver as efficiently as AAV9. The parental AAV2R585E transduced the heart efficiently, but did not transduce the liver.
Figure 16B:
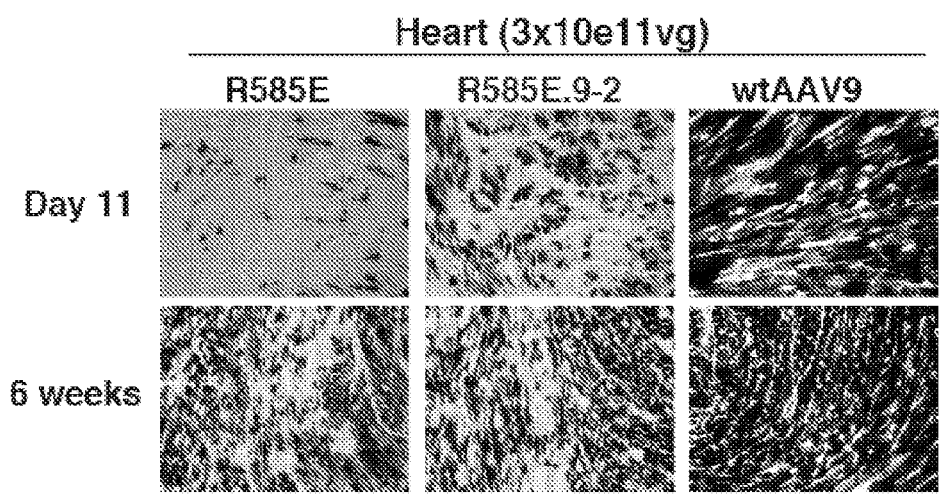
FIG. 16B is a set of images showing the difference in transgene expression between AAV2R585E (parental) and 9-2. The amino acid substitutions incorporated in 9-2 significantly accelerate the kinetics.
Figures 16C, 17:
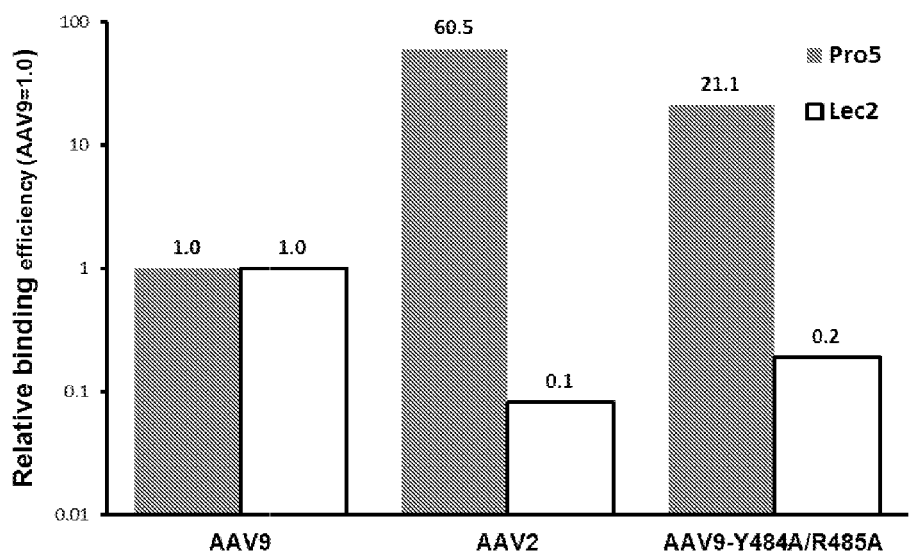
FIG. 16C is a depiction of vector genome copy number in the indicated tissues as determined by Southern Blot analysis.
FIG. 17 is a bar graph depicting the results of a cell surface binding assay using AAV2, AAV9, and AAV9 Y484A/R485A viral particles to bind to Pro5 and Lec2 cells at 4° C. Cell surface bound particles were quantified by viral genome qPCR.

In addition to this in vitro experiment, the biological properties of 9-2 in mice were established. Mice were injected with an AAV-CMV-lacZ vector including the 9-2 capsid intravenously. Eleven days and six weeks after injection, various organs were harvested including the liver, heart, and pancreas. As shown in FIGS. 16A, 16B, and 16C herein, the 9-2 capsid transduced the liver and heart as efficiently as AAV9 although the transduction efficiency in pancreas was less than that of AAV9. The 9-2 motif conferred not only the ability to bind galactose and transduce the liver on AAV2R585E, but it also accelerated transgene expression kinetics to a similar degree as that of AAV9.

These data indicate that AAV2R585E.9-2 has acquired AAV9-like biological properties with regard to transduction and is capable of binding to galactose on the cell surface.

The Pro5 and Lec2 cell transduction experiments using the DNA-barcoded hexapeptide scan AAV2R585E libraries ID 396 and 405 have also lent support to our conclusion that the galactose binding motif reside in the region we identified. Particularly, the "-P-NM-" sequence contained in the galactose binding motif appears to be an important motif of the observed enhancement in binding to Lec2. However, the "-P-NM-" by itself was not sufficient for the galactose binding (FIG. 16). When AAV2R585E carries the additional mutations, A464P/I470M or I470M/R471A, Lec2 transduction efficiencies are increased by several fold with statistical significance compared to AAV2R585E (Table 2). However, the degree of Lec2 transduction with either A464P/I470M or I470M/R471A by itself is much less than that with AAV2R585E. Interestingly, the effect by the A464P/I470M or I470M/R471A mutation is abolished when R471A/D472E is introduced (see AAVR585E-467-00700 and AAVR585E-469-00700).

Example 11

Y484A/R485A

In particular, the Y484A/R485A double mutation bound to various cell types at a much higher efficiency than AAV9, though it lacks the ability to bind the terminal galactose. As shown in FIG. 17, the double mutant binds to Pro5 cells 60 times better than the parental AAV9. Neuraminidase treatment of Pro5 cells did not impair binding of the virus.

Figure 18:
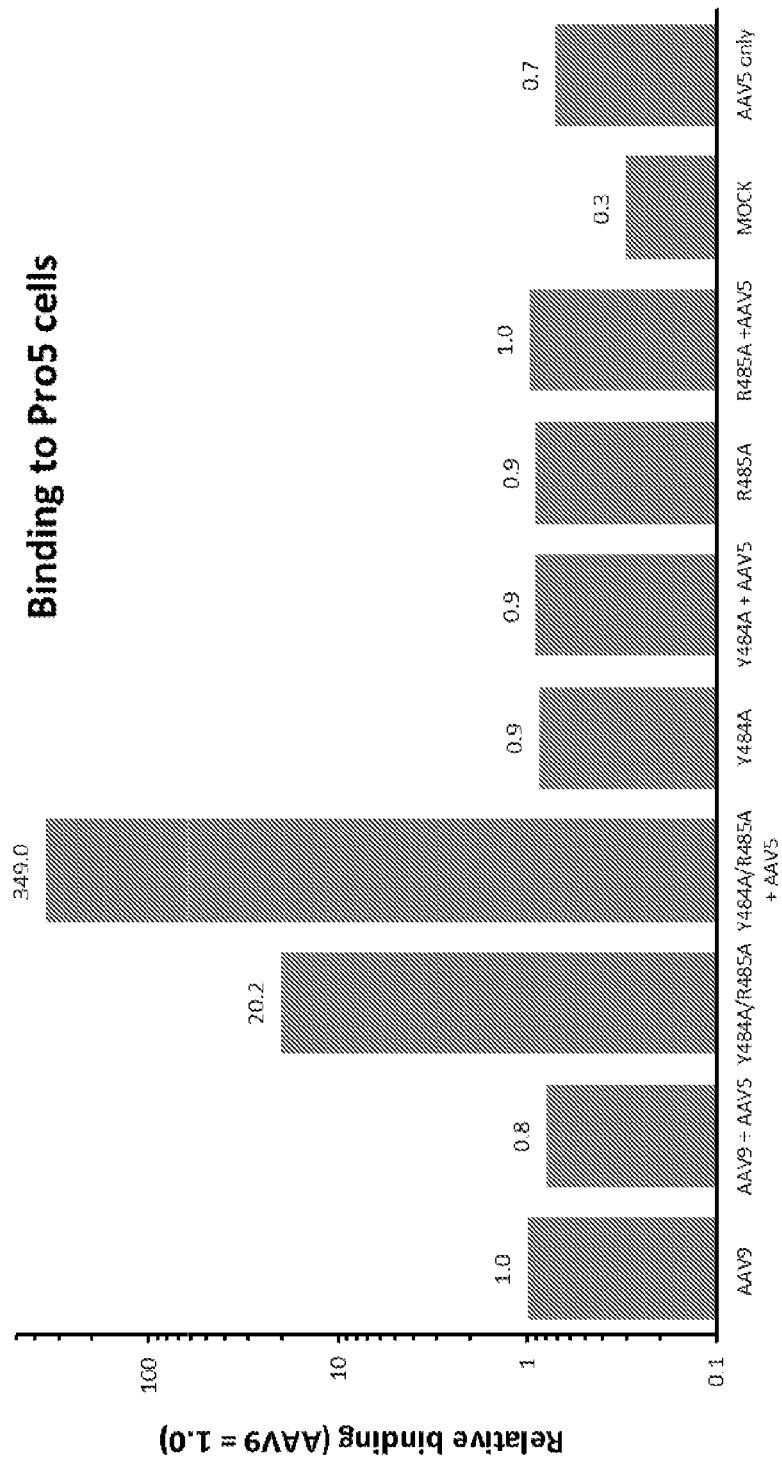
FIG. 18 is a bar graph depicting the results of a cell surface binding assay in the presence or absence of a 100-fold excess of AAV5 as a competitor. AAV5 had no effect on cell surface binding except in the presence of AAV9 Y484A/R485A.

Virus constructs comprising the single mutations AAV9Y484A and AAV9R485A were developed and a cell surface binding competition assay was performed using AAV5 as a competitor. Although neither single mutant showed an increase in cell surface binding, in a surprising result, the AAV9 Y484A/R485A double mutant exhibited 349-fold better cell surface binding relative to parental wild type AAV9 in the presence of AAV5 (FIG. 18.)

Figure 19:
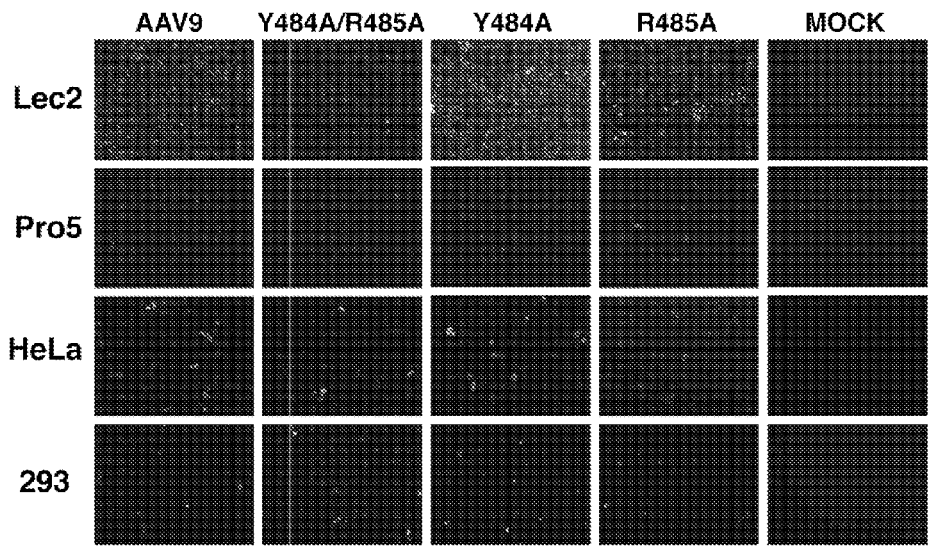
FIG. 19 is a set of images depicting the transduction efficiency of Y484 and/or R485 mutants in four cell lines in vitro. A Y484A/R485A mutation increases cell surface binding but does not result in increased transduction. Each single mutation (Y484A alone or R485A alone) both have increased transduction efficiency but similar binding to the wild type virus.

The ability of the Y484A and R485A single mutants to transduce cells was also tested. FIG. 19 shows that the Y484A/R485Y double mutant did not increase transduction efficiency. However, surprisingly, each single mutation Y484A and R485A each showed increased transduction efficiency in Lec2 cells.

TABLE 2

| Mutant ID | AA Substitution | Lec 2 Tx | Lec2Tx/ Pro5 Tx |
|---|---|---|---|
| AAVR585E-461-16000 | Q461L/Q464R/A465G/G466S | NC | |
| AAVR585E-461-00700 | S463Y/A465G | NA | NA |
| AAVR585E-461-00080 | Q461G/A465G | NC | |
| AAVR585E-461-00009 | Q461K/Q464V | NC | |
| AAVR585E-463-16000 | Q464R/A465G/G466S/A467P/S468A | NC | |
| AAVR585E-463-00700 | S463Y/A465G/A467P | NA | NA |
| AAVR585E-463-00080 | A465G/A467P/S468N | NC | |
| AAVR585E-463-00009 | Q464V/A467P | NC | |
| AAVR585E-465-16000 | A465G/G466S/A467P/S468A/D469G/I470M | 5.5 | 1.9 |
| AAVR585E-465-00700 | A465G/A467P/D469T/I470M | 6.2 | 1.3 |
| AAVR585E-465-00080 | A465G/A467P/S468N/D469T/I470M | 4.1 | 1.9 |
| AAVR585E-465-00009 | A467P/D469N/I470M | 5.8 | 1.3 |
| AAVR585E-467-16000 | A467P/S468A/D469G/I470M/R471S/D472V | 2.4 | 1.1 |
| AAVR585E-467-00700 | A467P/D469T/I470M/R471A/D472E | NC | |
| AAVR585E-467-00080 | A467P/S468N/D469T/I470M/R471A/D472N | 4.1 | 2.3 |
| AAVR585E-467-00009 | A467P/D469N/I470M/R471A/D472V | 5.9 | 2.0 |
| AAVR585E-469-16000 | D469G/I470M/R471S/D472V/S474P | NA | NA |
| AAVR585E-469-00700 | D469T/I470M/R471A/D472E/S474A | NC | |
| AAVR585E-469-00080 | D469T/I470M/R471A/D472N/S474A | 4.6 | 3.0 |
| AAVR585E-469-00009 | I470M/R471A/D472V/S474G | 5.9 | 3.1 |
| AAVR585E-471-16000 | R471S/D472V/S474P/R475K | NA | NA |
| AAVR585E-471-00700 | R471A/D472E/S474A/R475K | NC | |
| AAVR585E-471-00080 | R471A/D472N/S474A/R475K | NC | |
| AAVR585E-471-00009 | R471A/D472V/S474G | NC | |
| AAVR585E-473-16000 | S474P/R475K | NA | NA |
| AAVR585E-473-00780 | S474A/R475K | NC | |
| AAVR585E-473-00009 | S474G/W477Y/L478I | N.A. | N.A. |

Amino acids indicated in bold are mutations introduced in AAV2R585E to create AAVR585E.9. Transduction of AAV2R585E = 1.0.
NC—No Change: no statistically significant difference in transduction relative to AAV2R585E.
All values shown greater than 1.0 are statistically significant relative to AAV2R585E (p < 0.05).
NA., not applicable due to insufficient viral particle formation.
Tx—transduction.

Example 12

Identification of AAV9 Capsid Amino Acid Mutations that Affect Tissue Transduction to the Liver A total of 3 adult male mice were injected intravenously with DNA-barcoded AAV9 mutant libraries IDs 401, 406 and 407. The following 12 tissues; brain, heart, lung, liver, kidney, spleen, intestine, pancreas, testis, muscle, fat and skin 6 to 8 weeks after injection. Total DNA was extracted from each tissue and subjected to the AAV Barcode-Seq analysis. Table 3 shows the composition of AAV9 mutant libraries ID#'s 401, 406, 407 for double alanine mutants, two clones of each set of double mutants are included.

TABLE 3 composition of AAV9 mutant libraries ID #'s 401, 406, and 407.

| Library | AAV | # mutants | # clones | Amino Acids of SEQ ID NO: 1 covered | Total # of clones |
|---|---|---|---|---|---|
| 401 | AAV9 | Control | 15 | | 106 |
| | AAV2R585E | Control | 15 | | |
| | AAV9 double alanine mutants | 38 | 76 | 540-615 | |
| 406 | AAV9 | Control | 15 | | 214 |
| | AAV2R585E | Control | 15 | | |
| | AAV9 double alanine mutants | 92 | 184 | 356-539 | |
| 407 | AAV9 | Control | 15 | | 152 |
| | AAV2R585E | Control | 15 | | |
| | AAV9 double alanine mutants | 61 | 122 | 616-736 | |

Figure 20:
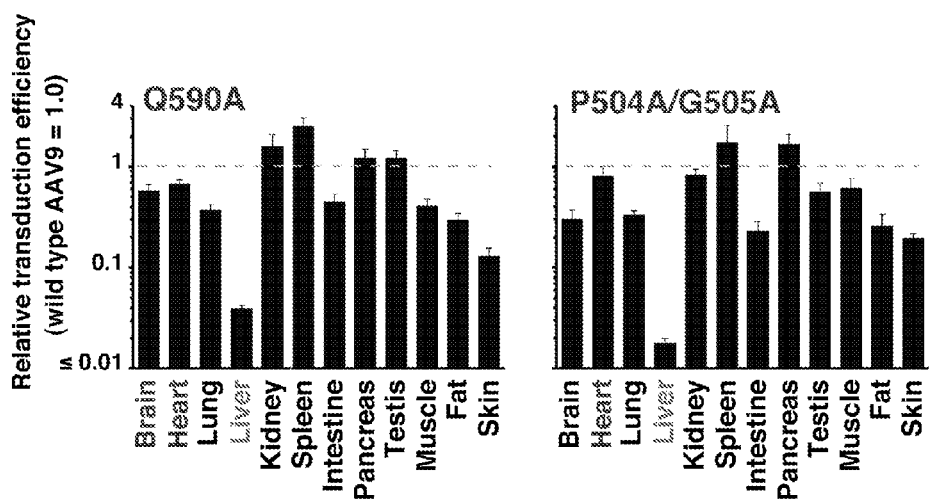
FIG. 20 is a bar graph showing the results from Table 4 and Example 12 below. The indicated mutants transduce poorly to the liver. Transduction efficiency is normalized to that of wild type AAV9. The data represent the mean and standard deviation of 3 animals.

Table 4 and FIG. 20 show that a P504A/G505A double mutant and a Q590A single mutant display efficient transduction of most tissue types, but is excluded from the liver.

TABLE 4 transduction of the indicated mutants into tissues.

| Mutations | B | H | Lu | Lv | K | S | I | P | T | M | F | Sk |
|---|---|---|---|---|---|---|---|---|---|---|---|---|
| P504A/G505A | 0.30 | 1 | 0.33 | 0.02 | 1 | 1 | 0.23 | 1 | 0.56 | 0.61 | 0.26 | 0.19 |
| Q590A | 0.57 | 0.67 | 0.37 | 0.04 | 1 | 2.49 | 0.45 | 1 | 1 | 0.40 | 0.29 | 0.13 |

Abbreviations:
B = Blood,
H = Heart,
Lu = Lung,
Lv = Liver,
K = Kidney,
S = Spleen,
I = Intestine,
P = Prostate,
T = Testis,
M = Muscle,
F = Fat,
Sk = Skin.

Figure 21:
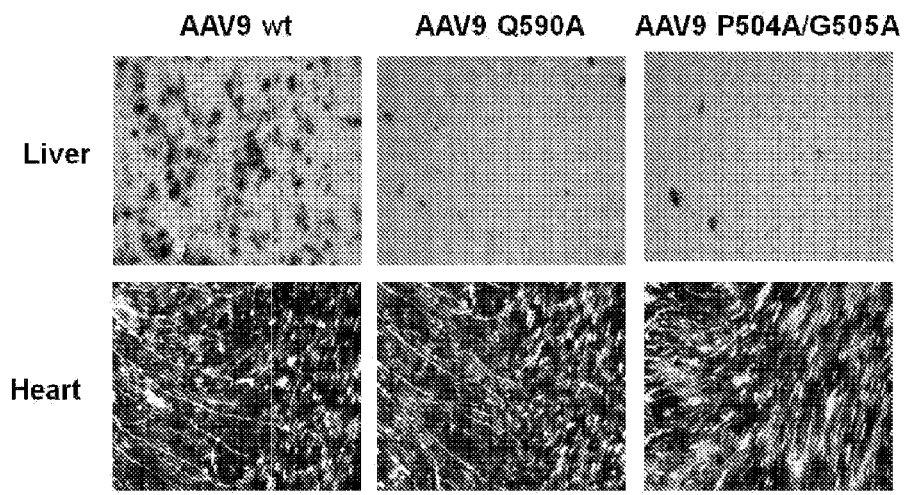
FIG. 21 is a set of images showing the in vivo transduction efficiency of AAV9P504A/G505A and AAV9Q590 vectors. An AAV-CMV-lacZ vector was packaged with these AAV9 mutant capsids were administered to C57Bl/6 or Rag1−/− mice at a dose of 1×10$^{12}$ vector genomes per mouse. Tissue transduction efficiency was assessed by XGal staining 6 weeks post-injection. The two mutants avoided the liver while transducing the heart as efficiently as the wild type AAV9.

These two mutants were then tested in mice. AAV-CMV-lacZ viral genomes were packaged into these mutant capsids to create a lacZ marker gene expressing AAV vectors. These vectors were then intravenously injected into C57BL/6 wild type mice or Rag1−/− mice to evaluate tissue transduction efficiency. We harvested tissues from the wild type mice 11 days post-injection to investigate transgene expression in the early phase of AAV-mediated gene delivery. For longer-term assessment, we harvested tissues from Rag1−/− mice 6 weeks post-injection. Rag1−/− immunodeficient mice were used for a long-term follow-up to avoid efficacy-limiting host immune response against the immunogenic lacZ gene product. As a result, we confirmed that these two mutants have a liver-detargeting phenotype while preserving the ability to transduce the heart efficiently (FIG. 21). Although these amino acids are located separately in protein primary or tertiary structure, they are next to each other in quaternary structure (FIG. 22). This conforms to the fact that these two mutations resulted in manifesting almost the same phenotype. The liver-detargeting nature was also confirmed by the molecular analysis of vector genome copy numbers (FIG. 23).

Figure 25:
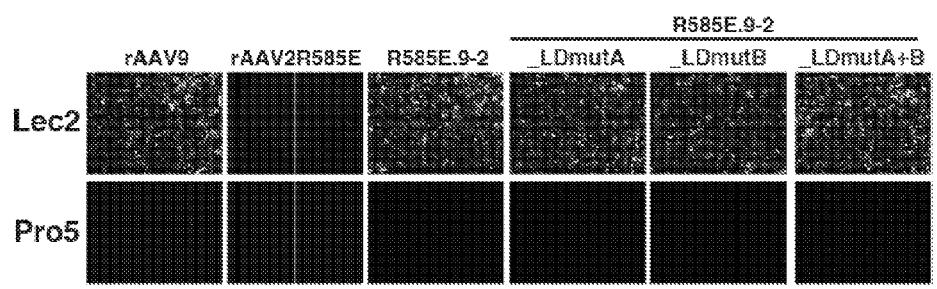
FIG. 25 is a set of images showing in vitro transduction efficiency of AAV2R585E.9-2-derived mutants carrying the liver-detargeting mutations identified in the context of AAV9. All the mutants, mtTG, mtQ and mtTGQ, show the same in vitro transduction profile of that for the parental AAV2R585E and the wild type AAV9.
Figure 26:
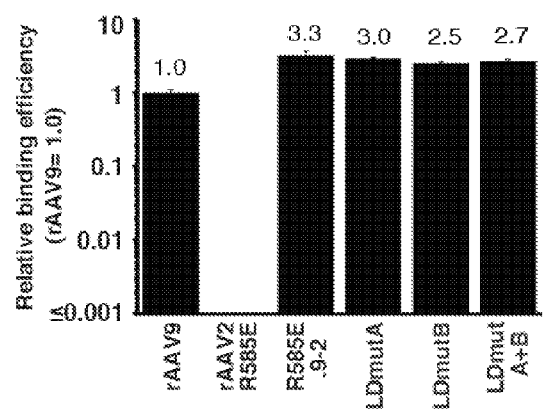
FIG. 26 shows the results of cell surface binding assay. All the mutants, mtTG, mtQ and mtTGQ, binds to Lec2 cells as efficiently as the parental AAV2R585E.9-2 and approximately 3-fold better than the wild type AAV9.
Figure 27:
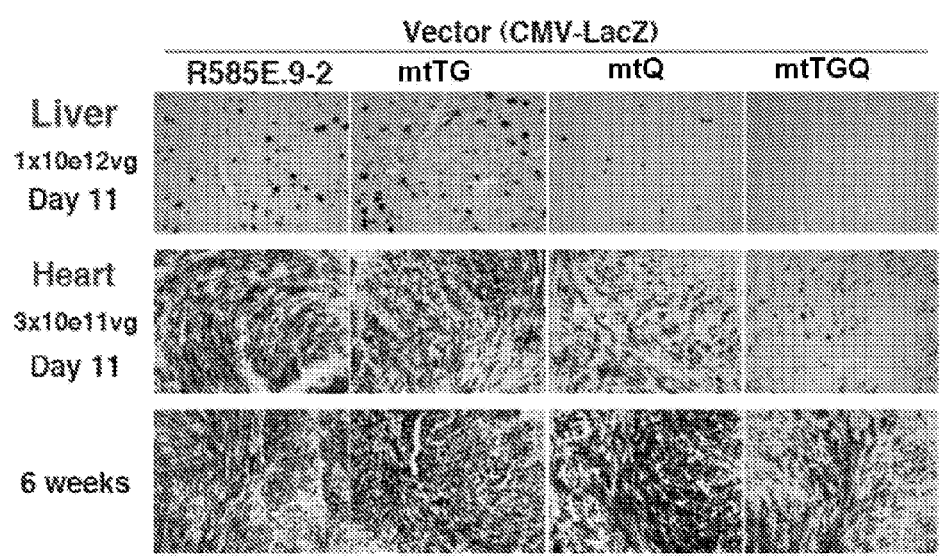
FIG. 27 is a set of images showing in vivo transduction efficiency of AAV2R585E.9-2-derived mutants carrying the liver-detargeting mutations identified in the context of AAV9. The mutants, mtTG and mtTGQ showed a liver-detargeting phenotype that preserved the heart transduction efficiency. mtQ did not have any effect, but had an ancillary role. C57BL/6 wild type mice and Rag1−/− mice were injected with AAV-CMV-lacZ vector encapsidated with the AAV capsids indicated in the figure. 11 days (for wild type mice) and 6 weeks (for Rag−/− mice) post-injection, tissue transduction efficiency was determined by XGal staining.

T503/G504 and Q589 in AAV2 are residues corresponding to P504/G505 and Q590 in AAV9. To investigate whether introduction of alanine mutations to these residues in the AAV2R585E.9-2 capsid also abolishes the ability to mediate liver transduction, we created three AAV2R585E.9-2 capsid mutants carrying T503A/G504A (mtTG), Q589A (mtQ) and T503A/G504A/Q589A (mt-TGQ) (FIG. 24) and packaged the lacZ or GFP expressing AAV viral genome into them. AAV helper plasmids used for AAV vector production were created based on pHLP22-R585E.9-2, which is the AAV helper plasmid for the production of AAV2R585E.9-2. These mutant AAV vectors were tested both in vitro and in vivo. No phenotypic changes were observed in vitro in that the in vitro transduction pattern was the same as that of AAV9 or the parental AAV2R585E.9-2 (FIG. 25). All of mtTG, mtQ and mtTGQ, bound to Lec2 cells as efficiently as the parental AAV2R585E.9-2 and approximately 3-fold better than the wild type AAV9 (FIG. 26). However, in mice, it was found that mtTG substantially attenuated liver transduction and mtTGQ completely abolished liver transduction, while both mtTG and mtTGQ retained the capability of transducing the heart (FIG. 27). Q589A had only an ancillary role in the context of AAV2R585E.9-2.

The invention claimed is:

1. An adeno associated virus plasmid comprising:
a polynucleotide that encodes a protein with the amino acid sequence of SEQ ID NO: 1 or an amino acid sequence having at least about 60%, at least about 75%, at least about 80%, at least about 90%, or at least about 95% sequence identity to SEQ ID NO: 1, wherein the protein further comprises a mutation at at least one of L380, T381, L382, N383, I440, D441, Y446, L447, I450, T451, V465, S469, N470, M471, Q474, G475, Y484, R485, E500, W503, P504, R514, N515, S516, and L517.

2. The adeno associated virus plasmid of claim 1, wherein the mutation is at at least one of I451, V465, S469, N470, M471, G475, Y484, E500, N515, and L517.

3. The adeno associated virus plasmid of claim 1, wherein the mutation is at least one of Y484A and R485A.

4. The adeno associated virus plasmid of claim 1, wherein the mutation is in a viral capsid protein.

5. An adeno associated virus plasmid comprising:
a polynucleotide that encodes a protein with the amino acid sequence of SEQ ID NO: 4 or an amino acid sequence having at least about 60%, at least about 75%, at least about 80%, at least about 90%, or at least about 95% sequence identity to SEQ ID NO: 4, the protein further comprises a mutation at at least one of Q464, A467, D469, I470, R471, D472, S474, S501, and D514.

6. The adeno associated virus plasmid of claim 5, wherein the mutation is at least one of Q464R, Q464V, A467P, D469G, D469T, I470M, R471A, R471S, D472V, D472E, D472N, S474P, S474A, S474G, S501F, and D514R.

7. An adeno associated virus plasmid comprising:
a polynucleotide that encodes a protein with an amino acid sequence selected from at least one of SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 18, SEQ ID NO: 19, SEQ ID NO: 20, SEQ ID NO: 21, SEQ ID NO: 23, SEQ ID NO: 24, and SEQ ID NO: 25.

8. The adeno associated virus plasmid of claim 5, wherein the mutation is in a viral capsid protein.

9. The plasmid of claim 1, wherein the polynucleotide encodes a protein comprising a mutation at an additional amino acid.

10. An adeno associated virus vector derived from the plasmid of claim 1.

11. A method of delivering a polynucleotide that encodes a protein of interest to a tissue in a subject, the method comprising:
administering an effective amount of an adeno associated virus vector to the subject, wherein the adeno associated virus vector comprises an adeno associated virus plasmid comprising:
a polynucleotide that encodes a protein with the amino acid sequence of SEQ ID NO: 1 or an amino acid sequence having at least about 90% or at least about 95% sequence identity to SEQ ID NO: 1, wherein the protein further comprises a mutation at at least one of L380, T381, L382, N383, I440, D441, Y446, L447, T450, I451, V465, S469, N470, M471, Q474, G475, Y484, R485, E500, W503, P504, R514, N515, S516, and L517.

12. An adeno associated virus vector derived from the plasm id of claim 5.

13. A method of delivering a polynucleotide that encodes a protein of interest to a tissue in a subject, the method comprising:
administering an effective amount of an adeno associated virus vector to the subject, wherein the adeno associated virus vector comprises an adeno associated virus plasmid comprising:
a polynucleotide that encodes a protein with the amino acid sequence of SEQ ID NO: 4 or an amino acid sequence having at least about 90%, or at least about 95% sequence identity to SEQ ID NO: 4, the protein further comprises a mutation at at least one of Q464, A467, D469, I470, R471, D472, S474, S501, and D514.

14. An adeno associated virus plasmid comprising:
a polynucleotide that encodes a protein with the amino acid sequence of SEQ ID NO: 4 or an amino acid sequence having at least about 60%, at least about 75%, at least about 80%, at least about 90%, or at least about 95% sequence identity to SEQ ID NO: 4, further comprising a Y500E mutation.

15. An adeno associated virus plasmid comprising:

a polynucleotide that encodes a protein with the amino acid sequence of SEQ ID NO: 1 or an amino acid sequence having at least about 60%, at least about 75%, at least about 80%, at least about 90%, or at least about 95% sequence identity to SEQ ID NO: 1, further comprising at least one of a F501A mutation, a G505A mutation, and a Q590A mutation.

* * * * *

SEQUENCE LISTING

<160> NUMBER OF SEQ ID NOS: 25

<210> SEQ ID NO 1
<211> LENGTH: 736
<212> TYPE: PRT
<213> ORGANISM: adeno associated virus

<400> SEQUENCE: 1

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
    130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
        355                 360                 365

```
Ala Asp Val Phe Met Ile Pro Gln Tyr Gly Tyr Leu Thr Leu Asn Asp
        370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
                420                 425                 430

Asp Arg Leu Met Asn Pro Leu Ile Asp Gln Tyr Leu Tyr Tyr Leu Ser
            435                 440                 445

Lys Thr Ile Asn Gly Ser Gly Gln Asn Gln Gln Thr Leu Lys Phe Ser
450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Gly Ala Ser Ser Trp Ala Leu Asn
            500                 505                 510

Gly Arg Asn Ser Leu Met Asn Pro Gly Pro Ala Met Ala Ser His Lys
        515                 520                 525

Glu Gly Glu Asp Arg Phe Phe Pro Leu Ser Gly Ser Leu Ile Phe Gly
530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Ala Gln Ala Gln
            580                 585                 590

Thr Gly Trp Val Gln Asn Gln Gly Ile Leu Pro Gly Met Val Trp Gln
        595                 600                 605

Asp Arg Asp Val Tyr Leu Gln Gly Pro Ile Trp Ala Lys Ile Pro His
610                 615                 620

Thr Asp Gly Asn Phe His Pro Ser Pro Leu Met Gly Gly Phe Gly Met
625                 630                 635                 640

Lys His Pro Pro Pro Gln Ile Leu Ile Lys Asn Thr Pro Val Pro Ala
                645                 650                 655

Asp Pro Pro Thr Ala Phe Asn Lys Asp Lys Leu Asn Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735

<210> SEQ ID NO 2
<211> LENGTH: 2211
<212> TYPE: DNA
<213> ORGANISM: adeno associated virus

<400> SEQUENCE: 2
atggctgccg atggttatct tccagattgg ctcgaggaca accttagtga aggaattcgc     60
```

-continued

| | |
|---|---|
| gagtggtggg ctttgaaacc tggagcccct caacccaagg caaatcaaca acatcaagac | 120 |
| aacgctcgag gtcttgtgct tccgggttac aaataccttg gacccggcaa cggactcgac | 180 |
| aaggggagc cggtcaacgc agcagacgcg gcggccctcg agcacgacaa ggcctacgac | 240 |
| cagcagctca aggccggaga caacccgtac ctcaagtaca accacgccga cgccgagttc | 300 |
| caggagcggc tcaaagaaga tacgtctttt gggggcaacc tcgggcgagc agtcttccag | 360 |
| gccaaaaaga ggcttcttga acctcttggt ctggttgagg aagcggctaa gacggctcct | 420 |
| ggaaagaaga ggcctgtaga gcagtctcct caggaaccgg actcctccgc gggtattggc | 480 |
| aaatcgggtg cacagcccgc taaaaagaga ctcaatttcg gtcagactgg cgacacagag | 540 |
| tcagtcccag accctcaacc aatcggagaa cctcccgcag cccctcagg tgtgggatct | 600 |
| cttacaatgg cttcaggtgg tggcgcacca gtggcagaca taacgaaggt gccgatgga | 660 |
| gtgggtagtt cctcgggaaa ttggcattgc gattcccaat ggctggggga cagagtcatc | 720 |
| accaccagca cccgaacctg ggccctgccc acctacaaca tcacctcta aagcaaatc | 780 |
| tccaacagca catctggagg atcttcaaat gacaacgcct acttcggcta cagcaccccc | 840 |
| tgggggtatt ttgacttcaa cagattccac tgccacttct caccacgtga ctggcagcga | 900 |
| ctcatcaaca caactggggg attccggcct aagcgactca acttcaagct cttcaacatt | 960 |
| caggtcaaag aggttacgga caacaatgga gtcaagacca tcgccaataa ccttaccagc | 1020 |
| acggtccagg tcttcacgga ctcagactat cagctcccgt acgtgctcgg gtcggctcac | 1080 |
| gagggctgcc tcccgccgtt cccagcggac gttttcatga ttcctcagta cgggtatctg | 1140 |
| acgcttaatg atggaagcca ggccgtgggt cgttcgtcct tttactgcct ggaatatttc | 1200 |
| ccgtcgcaaa tgctaagaac gggtaacaac ttccagttca gctacgagtt tgagaacgta | 1260 |
| cctttccata gcagctacgc tcacagccaa agcctggacc gactaatgaa tcccactcatc | 1320 |
| gaccaatact tgtactatct ctcaaagact attaacggtt ctggacagaa tcaacaaacg | 1380 |
| ctaaaattca gtgtggccgg acccagcaac atggctgtcc agggaagaaa ctacatacct | 1440 |
| ggacccagct accgacaaca acgtgtctca accactgtga ctcaaaacaa caacagcgaa | 1500 |
| tttgcttggc ctgagcttc ttcttgggct ctcaatggac gtaatagctt gatgaatcct | 1560 |
| ggacctgcta tggccagcca caagaagga gaggaccgtt tctttccttt gtctggatct | 1620 |
| ttaatttttg gcaaacaagg aactggaaga gacaacgtgg atgcggacaa agtcatgata | 1680 |
| accaacgaag aagaaattaa aactactaac ccggtagcaa cggagtccta tggacaagtg | 1740 |
| gccacaaacc accagagtgc ccaagcacag gcgcagaccg gctgggttca aaaccaagga | 1800 |
| atacttccgg gtatggtttg gcaggacaga gatgtgtacc tgcaaggacc catttgggcc | 1860 |
| aaaattcctc acacggacgg caactttcac ccttctccgc tgatgggagg gtttggaatg | 1920 |
| aagcacccgc ctcctcagat cctcatcaaa aacacacctg tacctgcgga tcctccaacg | 1980 |
| gccttcaaca aggacaagct gaactctttc atcacccagt attctactgg ccaagtcagc | 2040 |
| gtggagatcg agtgggagct gcagaaggaa acagcaagc gctggaaccc ggagatccag | 2100 |
| tacacttcca actattacaa gtctaataat gttgaatttg ctgttaatac tgaaggtgta | 2160 |
| tatagtgaac cccgccccat tggcaccaga tacctgactc gtaatctgta a | 2211 |

```
<210> SEQ ID NO 3
<211> LENGTH: 7953
<212> TYPE: DNA
<213> ORGANISM: Artificial Sequence
<220> FEATURE:
<223> OTHER INFORMATION: Plasmid
```

```
<220> FEATURE:
<221> NAME/KEY: misc_feature
<222> LOCATION: (4471)..(4482)
<223> OTHER INFORMATION: n is a, c, g, or t
<220> FEATURE:
<221> NAME/KEY: misc_feature
<222> LOCATION: (4503)..(4514)
<223> OTHER INFORMATION: n is a, c, g, or t

<400> SEQUENCE: 3
```

| | | | | | |
|---|---|---|---|---|---|
| aagctcctgc | aggcagctgc | gcgctcgctc | gctcactgag | gccgcccggg | caaagcccgg |   60 |
| gcgtcgggcg | acctttggtc | gcccggcctc | agtgagcgag | cgagcgcgca | gagagggagt |  120 |
| ggccaactcc | atcactaggg | gttcctggag | gggtggagtc | gtgacgtgaa | ttacgtcata |  180 |
| gggttaggga | ggtcctgtat | tagaggtcac | gtgagtgttt | tgcgacattt | tgcgacacca |  240 |
| tgtggtcacg | ctgggtattt | aagcccgagt | gagcacgcag | ggtctccatt | ttgaagcggg |  300 |
| aggtttgaac | gcgcagccgc | catgccgggg | ttttacgaga | ttgtgattaa | ggtccccagc |  360 |
| gaccttgacg | ggcatctgcc | cggcatttct | gacagctttg | tgaactgggt | ggccgagaag |  420 |
| gaatgggagt | tgccgccaga | ttctgacatg | gatctgaatc | tgattgagca | ggcacccctg |  480 |
| accgtggccg | agaagctgca | gcgcgacttt | ctgacggaat | ggcgccgtgt | gagtaaggcc |  540 |
| ccggaggccc | ttttctttgt | gcaatttgag | aagggagaga | gctacttcca | catgcacgtg |  600 |
| ctcgtggaaa | ccaccggggt | gaaatccatg | gttttgggac | gtttcctgag | tcagattcgc |  660 |
| gaaaaactga | ttcagagaat | ttaccgcggg | atcgagccga | ctttgccaaa | ctggttcgcg |  720 |
| gtcacaaaga | ccagaaatgg | cgccggaggc | gggaacaagg | tggtggatga | gtgctacatc |  780 |
| cccaattact | tgctccccaa | aacccagcct | gagctccagt | gggcgtggac | taatatggaa |  840 |
| cagtatttaa | gcgcctgttt | gaatctcacg | gagcgtaaac | ggttggtggc | gcagcatctg |  900 |
| acgcacgtgt | cgcagacgca | ggagcagaac | aaagagaatc | agaatcccaa | ttctgatgcg |  960 |
| ccggtgatca | gatcaaaaac | ttcagccagg | tacatggagc | tggtcgggtg | gctcgtggac | 1020 |
| aaggggatta | cctcggagaa | gcagtggatc | caggaggacc | aggcctcata | catctccttc | 1080 |
| aatgcggcct | ccaactcgcg | gtcccaaatc | aaggctgcct | tggacaatgc | gggaaagatt | 1140 |
| atgagcctga | ctaaaaccgc | ccccgactac | ctggtgggcc | agcagcccgt | ggaggacatt | 1200 |
| tccagcaatc | ggatttataa | aattttggaa | ctaaacgggt | acgatcccca | atatgcggct | 1260 |
| tccgtctttc | tgggatgggc | cacgaaaaag | ttcggcaaga | ggaacaccat | ctggctgttt | 1320 |
| gggcctgcaa | ctaccgggaa | gaccaacatc | gcggaggcca | tagcccacac | tgtgcccttc | 1380 |
| tacgggtgcg | taaactggac | caatgagaac | tttcccttca | acgactgtgt | cgacaagatg | 1440 |
| gtgatctggt | gggaggaggg | gaagatgacc | gccaaggtcg | tggagtcggc | caaagccatt | 1500 |
| ctcggaggaa | gcaaggtgcg | cgtggaccag | aaatgcaagt | cctcggccca | gatagacccg | 1560 |
| actcccgtga | tcgtcacctc | caacaccaac | atgtgcgccg | tgattgacgg | gaactcaacg | 1620 |
| accttcgaac | accagcagcc | gttgcaagac | cggatgttca | aatttgaact | cacccgccgt | 1680 |
| ctggatcatg | actttgggaa | ggtcaccaag | caggaagtca | aagactttt | ccggtgggca | 1740 |
| aaggatcacg | tggttgaggt | ggagcatgaa | ttctacgtca | aaagggtgg | agccaagaaa | 1800 |
| agacccgccc | ccagtgacgc | agatataagt | gagcccaaac | gggtgcgcga | gtcagttgcg | 1860 |
| cagccatcga | cgtcagacgc | ggaagcttcg | atcaactacg | cggacaggta | ccaaaacaaa | 1920 |
| tgttctcgtc | acgtgggcat | gaatctgatg | ctgtttccct | gcagacaatg | cgagagactg | 1980 |
| aatcagaatt | caaatatctg | cttcactcac | ggtgtcaaag | actgtttaga | gtgctttccc | 2040 |

-continued

```
gtgtcagaat ctcaacccgt ttctgtcgtc aaaaaggcgt atcagaaact gtgctacatt    2100
catcacatca tgggaaaggt gccagacgct tgcactgcat gcgacctggt caatgtggac    2160
ttggatgact gtgtttctga acaataaatg acttaaacca ggtatggctg ccgatggtta    2220
tcttccagat tggctcgagg acaaccttag tgaaggaatt cgcgagtggt gggcttttgaa   2280 acctggagcc cctcaaccca aggcaaatca acaacatcaa gacaacgctc gaggtcttgt    2340
gcttccgggt tacaaatacc ttggacccgg caacggactc gacaaggggg agccggtcaa    2400
cgcagcagac gcggcggccc tcgagcacga caaggcctac gaccagcagc tcaaggccgg    2460
agacaacccg tacctcaagt acaaccacgc cgacgccgag ttccaggagc ggctcaaaga    2520
agatacgtct tttgggggca acctcgggcg agcagtcttc caggccaaaa agaggcttct    2580
tgaacctctt ggtctggttg aggaagcggc taagacggct cctggaaaga agaggcctgt    2640
agagcagtct cctcaggaac cggactcctc cgcgggtatt ggcaaatcgg gtgcacagcc    2700
cgctaaaaag agactcaatt tcggtcagac tggcgacaca gagtcagttc cggaccctca    2760
accaatcgga gaacctcccg cagcccctc aggtgtggga tctcttacaa tggcttcagg    2820
tggtggcgca ccagtggcag acaataacga aggtgccgat ggagtgggta gttcctcggg    2880
aaattggcat tgcgattccc aatggctggg ggacagagtc atcaccacca gcacccgaac    2940
ctgggccctg cccacctaca acaatcacct ctacaagcaa atctccaaca gcacatctgg    3000
aggatcttca aatgacaacg cctacttcgg ctacagcacc ccctgggggt attttgactt    3060
caacagattc cactgccact tctcaccacg tgactggcag cgactcatca acaacaactg    3120
gggattccgg cctaagcgac tcaacttcaa gctcttcaac attcaggtca agagggttac    3180
ggacaacaat ggagtcaaga ccatcgccaa taaccttacc agcacggtcc aggtcttcac    3240 ggactcgac tatcagctcc cgtacgtgct cgggtcggct cacgagggct gcctcccgcc    3300
gttcccagcg gacgttttca tgattcctca gtacgggtat ctgacgctta atgatggaag    3360
ccaggccgtg ggtcgttcgt cctttttactg cctggaatat tttcccgtcgc aaatgctaag    3420 aacgggtaac aacttccagt tcagctacga gtttgagaac gtaccttttcc atagcagcta    3480 cgctcacagc caaagcctgg accgactaat gaatccactc atcgaccaat acttgtacta    3540
tctctcaaag actattaacg gttctggaca gaatcaacaa acgctaaaat tcagtgtggc    3600
cggacccagc aacatggctg tccagggaag aaactacata cctggaccca gctaccgaca    3660
acaacgtgtc tcaaccactg tgactcaaaa caacaacagc gaatttgctt ggcctggagc    3720
ttcttcttgg gctctcaatg gacgtaatag cttgatgaat cctggacctg ctatggccag    3780
ccacaaagaa ggagaggacc gtttctttcc cttaagtgga tctttaattt ttggcaaaca    3840
aggaactgga agagacaacg tggatgcgga caaagtcatg ataaccaacg aagaagaaat    3900
taaaactact aacccggtag caacggagtc ctatggacaa gtggccacaa accaccagag    3960
tgcccaagca caggcgcaga ccggctgggt tcaaaaccaa ggaatacttc cgggtatggt    4020
ttggcaggac agagatgtgt acctgcaagg acccatatgg gccaaaattc ctcacacgga    4080
cggcaacttt cacccttctc cgctgatggg agggtttgga atgaagcacc cgcctcctca    4140
gatcctcatc aaaaacacac ctgtacctgc ggatcctcca acggccttca acaaggacaa    4200
gctgaactct ttcatcaccc agtattctac tggccaagtc agcgtggaga tcgagtggga    4260
gctgcagaag gaaaacagca agcgctggaa cccggagatc cagtacactt ccaactatta    4320
caagtctaat aatgttgaat ttgctgttaa tactgaaggt gtatatagtg aaccccgccc    4380
cattggcacc agatacctga ctcgtaatct gtaattgctt gttaatcaat aaaccgttta    4440
```

-continued

```
attcacctac gtacttccgc tcatgctagc nnnnnnnnnn nnacggaaat acgatgtcgg    4500
gannnnnnnn nnnntgtaca gcaaagaccc caacgagaag cgcgatcaca tggtcctgct    4560
ggagttcgtg accgccgcca ccggttgatt cgtttcagtt gaactttggt ctctgcgaag    4620
ggcgaattcg ttttagataa gtagcatggc gggttaatca ttaactacaa ggaacccta    4680
gtgatggagt tggccactcc ctctctgcgc gctcgctcgc tcactgaggc cgggcgacca    4740
aaggtcgccc gacgcccggg ctttgcccgg gcggcctcag tgagcgagcg agcgcgcagc    4800
tgcctgcagg tcgactctag aggatccccg ggtaccgagc tcgaattcac tggccgtcgt    4860
tttacaacgt cgtgactggg aaaaccctgg cgttacccaa cttaatcgcc ttgcagcaca    4920
tcccccttc gccagctggc gtaatagcga agaggcccgc accgatcgcc ttcccaaca    4980
gttgcgcagc ctgaatggcg aatggcgcct gatgcggtat tttctcctta cgcatctgtg    5040
cggtatttca caccgcatac gtcaaagcaa ccatagtacg cgccctgtag cggcgcatta    5100
agcgcggcgg gtgtggtggt tacgcgcagc gtgaccgcta cacttgccag cgccctagcg    5160
cccgctcctt tcgctttctt cccttccttt ctcgccacgt tcgccggctt tccccgtcaa    5220
gctctaaatc gggggctccc tttagggttc cgatttagtg ctttacggca cctcgacccc    5280
aaaaaacttg atttgggtga tggttcacgt agtgggccat cgccctgata cggttttt    5340
cgccctttga cgttggagtc cacgttcttt aatagtggac tcttgttcca aactggaaca    5400
acactcaacc ctatctcggg ctattctttt gatttataag ggattttgcc gatttcggcc    5460
tattggttaa aaaatgagct gatttaacaa aaatttaacg cgaattttaa caaaatatta    5520
acgtttacaa ttttatggtg cactctcagt acaatctgct ctgatgccgc atagttaagc    5580
cagccccgac acccgccaac acccgctgac gcgccctgac gggcttgtct gctcccggca    5640
tccgcttaca gacaagctgt gaccgtctcc gggagctgca tgtgtcagag gttttcaccg    5700
tcatcaccga aacgcgcgag acgaaagggc ctcgtgatac gcctattttt ataggttaat    5760
gtcatgataa taatggtttc ttagacgtca ggtggcactt ttcggggaaa tgtgcgcgga    5820
acccctattt gtttattttt ctaaatacat tcaaatatgt atccgctcat gagacaataa    5880
ccctgataaa tgcttcaata atattgaaaa aggaagagta tgagtattca acatttccgt    5940
gtcgccctta ttcccttttt tgcggcattt tgccttcctg ttttgctca cccagaaacg    6000
ctggtgaaag taaaagatgc tgaagatcag ttgggtgcac gagtgggtta catcgaactg    6060
gatctcaaca gcggtaagat ccttgagagt tttcgccccg aagaacgttt tccaatgatg    6120
agcactttta aagttctgct atgtggcgcg gtattatccc gtattgacgc cgggcaagag    6180
caactcggtc gccgcataca ctattctcag aatgacttgg ttgagtactc accagtcaca    6240
gaaaagcatc ttacggatgg catgacagta agagaattat gcagtgctgc cataaccatg    6300
agtgataaca ctgcggccaa cttacttctg acaacgatcg gaggaccgaa ggagctaacc    6360
gcttttttgc acaacatggg ggatcatgta actcgccttg atcgttggga accggagctg    6420
aatgaagcca taccaaacga cgagcgtgac accacgatgc ctgtagcaat ggcaacaacg    6480
ttgcgcaaac tattaactgg cgaactactt actctagctt cccggcaaca attaatagac    6540
tggatggagg cggataaagt tgcaggacca cttctgcgct cggcccttcc ggctggctgg    6600
tttattgctg ataaatctgg agccggtgag cgtgggtctc gcggtatcat tgcagcactg    6660
gggccagatg gtaagccctc ccgtatcgta gttatctaca cgacggggag tcaggcaact    6720
atggatgaac gaaatagaca gatcgctgag ataggtgcct cactgattaa gcattggtaa    6780
```

-continued

```
ctgtcagacc aagtttactc atatatactt tagattgatt taaaacttca ttttttaattt      6840
aaaaggatct aggtgaagat ccttttttgat aatctcatga ccaaaatccc ttaacgtgag      6900
ttttcgttcc actgagcgtc agaccccgta gaaaagatca aaggatcttc ttgagatcct      6960
ttttttctgc gcgtaatctg ctgcttgcaa acaaaaaaac caccgctacc agcggtggtt      7020
tgtttgccgg atcaagagct accaactctt tttccgaagg taactggctt cagcagagcg      7080
cagataccaa atactgtcct tctagtgtag ccgtagttag gccaccactt caagaactct      7140
gtagcaccgc ctacatacct cgctctgcta atcctgttac cagtggctgc tgccagtggc      7200
gataagtcgt gtcttaccgg gttggactca agacgatagt taccggataa ggcgcagcgg      7260
tcgggctgaa cggggggttc gtgcacacag cccagcttgg agcgaacgac ctacaccgaa      7320
ctgagatacc tacagcgtga gctatgagaa agcgccacgc ttcccgaagg agaaaggcg       7380
gacaggtatc cggtaagcgg cagggtcgga acaggagagc gcacgaggga gcttccaggg      7440
ggaaacgcct ggtatcttta tagtcctgtc gggtttcgcc acctctgact tgagcgtcga      7500
tttttgtgat gctcgtcagg gggcggagc ctatggaaaa acgccagcaa cgcggccttt       7560
ttacggttcc tggccttttg ctggcctttt gctcacatgt tctttcctgc gttatcccct      7620
gattctgtgg ataaccgtat taccgccttt gagtgagctg ataccgctcg ccgcagccga      7680
acgaccgagc gcagcgagtc agtgagcgag gaagcggaag agcgcccaat acgcaaaccg      7740
cctctccccg cgcgttggcc gattcattaa tgcagctggc acgacaggtt cccgactgg       7800
aaagcgggca gtgagcgcaa cgcaattaat gtgagttagc tcactcatta ggcaccccag      7860
gctttacact ttatgcttcc ggctcgtatg ttgtgtggaa ttgtgagcgg ataacaattt      7920
cacacaggaa acagctatga ccatgattac gcc                                   7953
```

<210> SEQ ID NO 4
<211> LENGTH: 735
<212> TYPE: PRT
<213> ORGANISM: Adeno Associated Virus

<400> SEQUENCE: 4

```
Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro
            20                  25                  30

Lys Pro Ala Glu Arg His Lys Asp Asp Ser Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Glu Ala Asp Ala Ala Ala Leu Glu His Asp Lys Ala Tyr Asp
65                  70                  75                  80

Arg Gln Leu Asp Ser Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Pro Val Lys Thr Ala Pro Gly Lys Lys Arg
    130                 135                 140

Pro Val Glu His Ser Pro Val Glu Pro Asp Ser Ser Ser Gly Thr Gly
145                 150                 155                 160

Lys Ala Gly Gln Gln Pro Ala Arg Lys Arg Leu Asn Phe Gly Gln Thr
```

```
                     165                 170                 175
Gly Asp Ala Asp Ser Val Pro Asp Pro Gln Pro Leu Gly Gln Pro Pro
                180                 185                 190

Ala Ala Pro Ser Gly Leu Gly Thr Asn Thr Met Ala Thr Gly Ser Gly
            195                 200                 205

Ala Pro Met Ala Asp Asn Asn Glu Gly Ala Asp Gly Val Gly Asn Ser
        210                 215                 220

Ser Gly Asn Trp His Cys Asp Ser Thr Trp Met Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
            260                 265                 270

Phe Gly Tyr Ser Thr Pro Trp Gly Tyr Phe Asp Phe Asn Arg Phe His
        275                 280                 285

Cys His Phe Ser Pro Arg Asp Trp Gln Arg Leu Ile Asn Asn Asn Trp
    290                 295                 300

Gly Phe Arg Pro Lys Arg Leu Asn Phe Lys Leu Phe Asn Ile Gln Val
305                 310                 315                 320

Lys Glu Val Thr Gln Asn Asp Gly Thr Thr Thr Ile Ala Asn Asn Leu
                325                 330                 335

Thr Ser Thr Val Gln Val Phe Thr Asp Ser Glu Tyr Gln Leu Pro Tyr
            340                 345                 350

Val Leu Gly Ser Ala His Gln Gly Cys Leu Pro Pro Phe Pro Ala Asp
        355                 360                 365

Val Phe Met Val Pro Gln Tyr Gly Tyr Leu Thr Leu Asn Asn Gly Ser
    370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Thr Phe Ser Tyr Thr Phe Glu
                405                 410                 415

Asp Val Pro Phe His Ser Ser Tyr Ala His Ser Gln Ser Leu Asp Arg
            420                 425                 430

Leu Met Asn Pro Leu Ile Asp Gln Tyr Leu Tyr Tyr Leu Ser Arg Thr
        435                 440                 445

Asn Thr Pro Ser Gly Thr Thr Thr Gln Ser Arg Leu Gln Phe Ser Gln
    450                 455                 460

Ala Gly Ala Ser Asp Ile Arg Asp Gln Ser Arg Asn Trp Leu Pro Gly
465                 470                 475                 480

Pro Cys Tyr Arg Gln Gln Arg Val Ser Lys Thr Ser Ala Asp Asn Asn
                485                 490                 495

Asn Ser Glu Tyr Ser Trp Thr Gly Ala Thr Lys Tyr His Leu Asn Gly
            500                 505                 510

Arg Asp Ser Leu Val Asn Pro Gly Pro Ala Met Ala Ser His Lys Asp
        515                 520                 525

Asp Glu Glu Lys Phe Phe Pro Gln Ser Gly Val Leu Ile Phe Gly Lys
    530                 535                 540

Gln Gly Ser Glu Lys Thr Asn Val Asp Ile Glu Lys Val Met Ile Thr
545                 550                 555                 560

Asp Glu Glu Glu Ile Arg Thr Thr Asn Pro Val Ala Thr Glu Gln Tyr
                565                 570                 575

Gly Ser Val Ser Thr Asn Leu Gln Arg Gly Asn Arg Gln Ala Ala Thr
            580                 585                 590
```

```
Ala Asp Val Asn Thr Gln Gly Val Leu Pro Gly Met Val Trp Gln Asp
        595                 600                 605
Arg Asp Val Tyr Leu Gln Gly Pro Ile Trp Ala Lys Ile Pro His Thr
    610                 615                 620
Asp Gly His Phe His Pro Ser Pro Leu Met Gly Gly Phe Gly Leu Lys
625                 630                 635                 640
His Pro Pro Pro Gln Ile Leu Ile Lys Asn Thr Pro Val Pro Ala Asn
                645                 650                 655
Pro Ser Thr Thr Phe Ser Ala Ala Lys Phe Ala Ser Phe Ile Thr Gln
                660                 665                 670
Tyr Ser Thr Gly Gln Val Ser Val Glu Ile Glu Trp Glu Leu Gln Lys
            675                 680                 685
Glu Asn Ser Lys Arg Trp Asn Pro Glu Ile Gln Tyr Thr Ser Asn Tyr
        690                 695                 700
Asn Lys Ser Val Asn Val Asp Phe Thr Val Asp Thr Asn Gly Val Tyr
705                 710                 715                 720
Ser Glu Pro Arg Pro Ile Gly Thr Arg Tyr Leu Thr Arg Asn Leu
                725                 730                 735

<210> SEQ ID NO 5
<211> LENGTH: 735
<212> TYPE: PRT
<213> ORGANISM: Adeno Associated Virus

<400> SEQUENCE: 5

Met Ala Ala Asp Gly Tyr Leu Pro Asp Trp Leu Glu Asp Thr Leu Ser
1               5                   10                  15
Glu Gly Ile Arg Gln Trp Trp Lys Leu Lys Pro Gly Pro Pro Pro Pro
            20                  25                  30
Lys Pro Ala Glu Arg His Lys Asp Asp Ser Arg Gly Leu Val Leu Pro
        35                  40                  45
Gly Tyr Lys Tyr Leu Gly Pro Phe Asn Gly Leu Asp Lys Gly Glu Pro
    50                  55                  60
Val Asn Glu Ala Asp Ala Ala Ala Leu Glu His Asp Lys Ala Tyr Asp
65                  70                  75                  80
Arg Gln Leu Asp Ser Gly Asp Asn Pro Tyr Leu Lys Tyr Asn His Ala
                85                  90                  95
Asp Ala Glu Phe Gln Glu Arg Leu Lys Glu Asp Thr Ser Phe Gly Gly
            100                 105                 110
Asn Leu Gly Arg Ala Val Phe Gln Ala Lys Lys Arg Val Leu Glu Pro
        115                 120                 125
Leu Gly Leu Val Glu Glu Pro Val Lys Thr Ala Pro Gly Lys Lys Arg
    130                 135                 140
Pro Val Glu His Ser Pro Val Glu Pro Asp Ser Ser Ser Gly Thr Gly
145                 150                 155                 160
Lys Ala Gly Gln Gln Pro Ala Arg Lys Arg Leu Asn Phe Gly Gln Thr
                165                 170                 175
Gly Asp Ala Asp Ser Val Pro Asp Pro Gln Pro Leu Gly Gln Pro Pro
            180                 185                 190
Ala Ala Pro Ser Gly Leu Gly Thr Asn Thr Met Ala Thr Gly Ser Gly
        195                 200                 205
Ala Pro Met Ala Asp Asn Asn Glu Gly Ala Asp Gly Val Gly Asn Ser
    210                 215                 220
Ser Gly Asn Trp His Cys Asp Ser Thr Trp Met Gly Asp Arg Val Ile
```

```
            225                 230                 235                 240
        Thr Thr Ser Thr Arg Thr Trp Ala Leu Pro Thr Tyr Asn Asn His Leu
                        245                 250                 255

Tyr Lys Gln Ile Ser Ser Gln Ser Gly Ala Ser Asn Asp Asn His Tyr
                        260                 265                 270

Phe Gly Tyr Ser Thr Pro Trp Gly Tyr Phe Asp Phe Asn Arg Phe His
                        275                 280                 285

Cys His Phe Ser Pro Arg Asp Trp Gln Arg Leu Ile Asn Asn Asn Trp
        290                 295                 300

Gly Phe Arg Pro Lys Arg Leu Asn Phe Lys Leu Phe Asn Ile Gln Val
        305                 310                 315                 320

Lys Glu Val Thr Gln Asn Asp Gly Thr Thr Thr Ile Ala Asn Asn Leu
                        325                 330                 335

Thr Ser Thr Val Gln Val Phe Thr Asp Ser Glu Tyr Gln Leu Pro Tyr
                        340                 345                 350

Val Leu Gly Ser Ala His Gln Gly Cys Leu Pro Pro Phe Pro Ala Asp
                        355                 360                 365

Val Phe Met Val Pro Gln Tyr Gly Tyr Leu Thr Leu Asn Asn Gly Ser
                        370                 375                 380

Gln Ala Val Gly Arg Ser Ser Phe Tyr Cys Leu Glu Tyr Phe Pro Ser
        385                 390                 395                 400

Gln Met Leu Arg Thr Gly Asn Asn Phe Thr Phe Ser Tyr Thr Phe Glu
                        405                 410                 415

Asp Val Pro Phe His Ser Ser Tyr Ala His Ser Gln Ser Leu Asp Arg
                        420                 425                 430

Leu Met Asn Pro Leu Ile Asp Gln Tyr Leu Tyr Tyr Leu Ser Arg Thr
                        435                 440                 445

Asn Thr Pro Ser Gly Thr Thr Thr Gln Ser Arg Leu Gln Phe Ser Gln
                        450                 455                 460

Gly Ser Pro Ala Gly Met Arg Asp Gln Ser Arg Asn Trp Leu Pro Gly
        465                 470                 475                 480

Pro Cys Tyr Arg Gln Gln Arg Val Ser Lys Thr Ser Ala Asp Asn Asn
                        485                 490                 495

Asn Ser Glu Tyr Ser Trp Thr Gly Ala Thr Lys Tyr His Leu Asn Gly
                        500                 505                 510

Arg Asp Ser Leu Val Asn Pro Gly Pro Ala Met Ala Ser His Lys Asp
                        515                 520                 525

Asp Glu Glu Lys Phe Phe Pro Gln Ser Gly Val Leu Ile Phe Gly Lys
                        530                 535                 540

Gln Gly Ser Glu Lys Thr Asn Val Asp Ile Glu Lys Val Met Ile Thr
        545                 550                 555                 560

Asp Glu Glu Glu Ile Arg Thr Thr Asn Pro Val Ala Thr Glu Gln Tyr
                        565                 570                 575

Gly Ser Val Ser Thr Asn Leu Gln Arg Gly Asn Arg Gln Ala Ala Thr
                        580                 585                 590

Ala Asp Val Asn Thr Gln Gly Val Leu Pro Gly Met Val Trp Gln Asp
                        595                 600                 605

Arg Asp Val Tyr Leu Gln Gly Pro Ile Trp Ala Lys Ile Pro His Thr
                        610                 615                 620

Asp Gly His Phe His Pro Ser Pro Leu Met Gly Gly Phe Gly Leu Lys
        625                 630                 635                 640

His Pro Pro Pro Gln Ile Leu Ile Lys Asn Thr Pro Val Pro Ala Asn
                        645                 650                 655
```

```
Pro Ser Thr Thr Phe Ser Ala Ala Lys Phe Ala Ser Phe Ile Thr Gln
        660                 665                 670

Tyr Ser Thr Gly Gln Val Ser Val Glu Ile Glu Trp Glu Leu Gln Lys
    675                 680                 685

Glu Asn Ser Lys Arg Trp Asn Pro Glu Ile Gln Tyr Thr Ser Asn Tyr
690                 695                 700

Asn Lys Ser Val Asn Val Asp Phe Thr Val Asp Thr Asn Gly Val Tyr
705                 710                 715                 720

Ser Glu Pro Arg Pro Ile Gly Thr Arg Tyr Leu Thr Arg Asn Leu
                725                 730                 735

<210> SEQ ID NO 6
<211> LENGTH: 735
<212> TYPE: PRT
<213> ORGANISM: Adeno Associated Virus

<400> SEQUENCE: 6

Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro Pro
            20                  25                  30

Lys Pro Ala Glu Arg His Lys Asp Asp Ser Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Glu Ala Asp Ala Ala Leu Glu His Asp Lys Ala Tyr Asp
65                  70                  75                  80

Arg Gln Leu Asp Ser Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Pro Val Lys Thr Ala Pro Gly Lys Lys Arg
    130                 135                 140

Pro Val Glu His Ser Pro Val Glu Pro Asp Ser Ser Ser Gly Thr Gly
145                 150                 155                 160

Lys Ala Gly Gln Gln Pro Ala Arg Lys Arg Leu Asn Phe Gly Gln Thr
                165                 170                 175

Gly Asp Ala Asp Ser Val Pro Asp Pro Gln Pro Leu Gly Gln Pro Pro
            180                 185                 190

Ala Ala Pro Ser Gly Leu Gly Thr Asn Thr Met Ala Thr Gly Ser Gly
        195                 200                 205

Ala Pro Met Ala Asp Asn Asn Glu Gly Ala Asp Gly Val Gly Asn Ser
    210                 215                 220

Ser Gly Asn Trp His Cys Asp Ser Thr Trp Met Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
            260                 265                 270

Phe Gly Tyr Ser Thr Pro Trp Gly Tyr Phe Asp Phe Asn Arg Phe His
        275                 280                 285

Cys His Phe Ser Pro Arg Asp Trp Gln Arg Leu Ile Asn Asn Asn Trp
```

-continued

```
                290                 295                 300
Gly Phe Arg Pro Lys Arg Leu Asn Phe Lys Leu Phe Asn Ile Gln Val
305                 310                 315                 320

Lys Glu Val Thr Gln Asn Asp Gly Thr Thr Thr Ile Ala Asn Asn Leu
                325                 330                 335

Thr Ser Thr Val Gln Val Phe Thr Asp Ser Glu Tyr Gln Leu Pro Tyr
                340                 345                 350

Val Leu Gly Ser Ala His Gln Gly Cys Leu Pro Pro Phe Pro Ala Asp
                355                 360                 365

Val Phe Met Val Pro Gln Tyr Gly Tyr Leu Thr Leu Asn Asn Gly Ser
                370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Thr Phe Ser Tyr Thr Phe Glu
                405                 410                 415

Asp Val Pro Phe His Ser Ser Tyr Ala His Ser Gln Ser Leu Asp Arg
                420                 425                 430

Leu Met Asn Pro Leu Ile Asp Gln Tyr Leu Tyr Tyr Leu Ser Arg Thr
                435                 440                 445

Asn Thr Pro Ser Gly Thr Thr Thr Gln Ser Arg Leu Gln Phe Ser Gln
                450                 455                 460

Gly Gly Pro Ser Thr Met Arg Asp Gln Ser Arg Asn Trp Leu Pro Gly
465                 470                 475                 480

Pro Cys Tyr Arg Gln Gln Arg Val Ser Lys Thr Ser Ala Asp Asn Asn
                485                 490                 495

Asn Ser Glu Tyr Ser Trp Thr Gly Ala Thr Lys Tyr His Leu Asn Gly
                500                 505                 510

Arg Asp Ser Leu Val Asn Pro Gly Pro Ala Met Ala Ser His Lys Asp
                515                 520                 525

Asp Glu Glu Lys Phe Phe Pro Gln Ser Gly Val Leu Ile Phe Gly Lys
                530                 535                 540

Gln Gly Ser Glu Lys Thr Asn Val Asp Ile Glu Lys Val Met Ile Thr
545                 550                 555                 560

Asp Glu Glu Glu Ile Arg Thr Thr Asn Pro Val Ala Thr Glu Gln Tyr
                565                 570                 575

Gly Ser Val Ser Thr Asn Leu Gln Arg Gly Asn Arg Gln Ala Ala Thr
                580                 585                 590

Ala Asp Val Asn Thr Gln Gly Val Leu Pro Gly Met Val Trp Gln Asp
                595                 600                 605

Arg Asp Val Tyr Leu Gln Gly Pro Ile Trp Ala Lys Ile Pro His Thr
                610                 615                 620

Asp Gly His Phe His Pro Ser Pro Leu Met Gly Gly Phe Gly Leu Lys
625                 630                 635                 640

His Pro Pro Pro Gln Ile Leu Ile Lys Asn Thr Pro Val Pro Ala Asn
                645                 650                 655

Pro Ser Thr Thr Phe Ser Ala Ala Lys Phe Ala Ser Phe Ile Thr Gln
                660                 665                 670

Tyr Ser Thr Gly Gln Val Ser Val Glu Ile Glu Trp Glu Leu Gln Lys
                675                 680                 685

Glu Asn Ser Lys Arg Trp Asn Pro Glu Ile Gln Tyr Thr Ser Asn Tyr
                690                 695                 700

Asn Lys Ser Val Asn Val Asp Phe Thr Val Asp Thr Asn Gly Val Tyr
705                 710                 715                 720
```

Ser Glu Pro Arg Pro Ile Gly Thr Arg Tyr Leu Thr Arg Asn Leu
            725                 730                 735

<210> SEQ ID NO 7
<211> LENGTH: 735
<212> TYPE: PRT
<213> ORGANISM: Adeno Associated Virus

<400> SEQUENCE: 7

Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro
            20                  25                  30

Lys Pro Ala Glu Arg His Lys Asp Asp Ser Arg Gly Leu Val Leu Pro
            35                  40                  45

Gly Tyr Lys Tyr Leu Gly Pro Phe Asn Gly Leu Asp Lys Gly Glu Pro
    50                  55                  60

Val Asn Glu Ala Asp Ala Ala Leu Glu His Asp Lys Ala Tyr Asp
65                  70                  75                  80

Arg Gln Leu Asp Ser Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Pro Val Lys Thr Ala Pro Gly Lys Lys Arg
130                 135                 140

Pro Val Glu His Ser Pro Val Glu Pro Asp Ser Ser Ser Gly Thr Gly
145                 150                 155                 160

Lys Ala Gly Gln Gln Pro Ala Arg Lys Arg Leu Asn Phe Gly Gln Thr
                165                 170                 175

Gly Asp Ala Asp Ser Val Pro Asp Pro Gln Pro Leu Gly Gln Pro Pro
            180                 185                 190

Ala Ala Pro Ser Gly Leu Gly Thr Asn Thr Met Ala Thr Gly Ser Gly
        195                 200                 205

Ala Pro Met Ala Asp Asn Asn Glu Gly Ala Asp Gly Val Gly Asn Ser
    210                 215                 220

Ser Gly Asn Trp His Cys Asp Ser Thr Trp Met Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
            260                 265                 270

Phe Gly Tyr Ser Thr Pro Trp Gly Tyr Phe Asp Phe Asn Arg Phe His
        275                 280                 285

Cys His Phe Ser Pro Arg Asp Trp Gln Arg Leu Ile Asn Asn Asn Trp
    290                 295                 300

Gly Phe Arg Pro Lys Arg Leu Asn Phe Lys Leu Phe Asn Ile Gln Val
305                 310                 315                 320

Lys Glu Val Thr Gln Asn Asp Gly Thr Thr Thr Ile Ala Asn Asn Leu
                325                 330                 335

Thr Ser Thr Val Gln Val Phe Thr Asp Ser Glu Tyr Gln Leu Pro Tyr
            340                 345                 350

Val Leu Gly Ser Ala His Gln Gly Cys Leu Pro Pro Phe Pro Ala Asp

```
                    355                 360                 365
Val Phe Met Val Pro Gln Tyr Gly Tyr Leu Thr Leu Asn Asn Gly Ser
370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Thr Phe Ser Tyr Thr Phe Glu
                405                 410                 415

Asp Val Pro Phe His Ser Ser Tyr Ala His Ser Gln Ser Leu Asp Arg
            420                 425                 430

Leu Met Asn Pro Leu Ile Asp Gln Tyr Leu Tyr Tyr Leu Ser Arg Thr
        435                 440                 445

Asn Thr Pro Ser Gly Thr Thr Thr Gln Ser Arg Leu Gln Phe Ser Gln
    450                 455                 460

Gly Gly Pro Asn Thr Met Arg Asp Gln Ser Arg Asn Trp Leu Pro Gly
465                 470                 475                 480

Pro Cys Tyr Arg Gln Gln Arg Val Ser Lys Thr Ser Ala Asp Asn Asn
                485                 490                 495

Asn Ser Glu Tyr Ser Trp Thr Gly Ala Thr Lys Tyr His Leu Asn Gly
            500                 505                 510

Arg Asp Ser Leu Val Asn Pro Gly Pro Ala Met Ala Ser His Lys Asp
        515                 520                 525

Asp Glu Glu Lys Phe Phe Pro Gln Ser Gly Val Leu Ile Phe Gly Lys
    530                 535                 540

Gln Gly Ser Glu Lys Thr Asn Val Asp Ile Glu Lys Val Met Ile Thr
545                 550                 555                 560

Asp Glu Glu Glu Ile Arg Thr Thr Asn Pro Val Ala Thr Glu Gln Tyr
                565                 570                 575

Gly Ser Val Ser Thr Asn Leu Gln Arg Gly Asn Arg Gln Ala Ala Thr
            580                 585                 590

Ala Asp Val Asn Thr Gln Gly Val Leu Pro Gly Met Val Trp Gln Asp
        595                 600                 605

Arg Asp Val Tyr Leu Gln Gly Pro Ile Trp Ala Lys Ile Pro His Thr
    610                 615                 620

Asp Gly His Phe His Pro Ser Pro Leu Met Gly Gly Phe Gly Leu Lys
625                 630                 635                 640

His Pro Pro Pro Gln Ile Leu Ile Lys Asn Thr Pro Val Pro Ala Asn
                645                 650                 655

Pro Ser Thr Thr Phe Ser Ala Ala Lys Phe Ala Ser Phe Ile Thr Gln
            660                 665                 670

Tyr Ser Thr Gly Gln Val Ser Val Glu Ile Glu Trp Glu Leu Gln Lys
        675                 680                 685

Glu Asn Ser Lys Arg Trp Asn Pro Glu Ile Gln Tyr Thr Ser Asn Tyr
    690                 695                 700

Asn Lys Ser Val Asn Val Asp Phe Thr Val Asp Thr Asn Gly Val Tyr
705                 710                 715                 720

Ser Glu Pro Arg Pro Ile Gly Thr Arg Tyr Leu Thr Arg Asn Leu
                725                 730                 735

<210> SEQ ID NO 8
<211> LENGTH: 735
<212> TYPE: PRT
<213> ORGANISM: Adeno Associated Virus

<400> SEQUENCE: 8
```

```
Met Ala Ala Asp Gly Tyr Leu Pro Asp Trp Leu Glu Asp Thr Leu Ser
 1               5                  10                  15
Glu Gly Ile Arg Gln Trp Trp Lys Leu Lys Pro Gly Pro Pro Pro Pro
            20                  25                  30
Lys Pro Ala Glu Arg His Lys Asp Asp Ser Arg Gly Leu Val Leu Pro
        35                  40                  45
Gly Tyr Lys Tyr Leu Gly Pro Phe Asn Gly Leu Asp Lys Gly Glu Pro
    50                  55                  60
Val Asn Glu Ala Asp Ala Ala Leu Glu His Asp Lys Ala Tyr Asp
65                  70                  75                  80
Arg Gln Leu Asp Ser Gly Asp Asn Pro Tyr Leu Lys Tyr Asn His Ala
                85                  90                  95
Asp Ala Glu Phe Gln Glu Arg Leu Lys Glu Asp Thr Ser Phe Gly Gly
            100                 105                 110
Asn Leu Gly Arg Ala Val Phe Gln Ala Lys Lys Arg Val Leu Glu Pro
            115                 120                 125
Leu Gly Leu Val Glu Glu Pro Val Lys Thr Ala Pro Gly Lys Lys Arg
    130                 135                 140
Pro Val Glu His Ser Pro Val Glu Pro Asp Ser Ser Ser Gly Thr Gly
145                 150                 155                 160
Lys Ala Gly Gln Gln Pro Ala Arg Lys Arg Leu Asn Phe Gly Gln Thr
                165                 170                 175
Gly Asp Ala Asp Ser Val Pro Asp Pro Gln Pro Leu Gly Gln Pro Pro
            180                 185                 190
Ala Ala Pro Ser Gly Leu Gly Thr Asn Thr Met Ala Thr Gly Ser Gly
            195                 200                 205
Ala Pro Met Ala Asp Asn Asn Glu Gly Ala Asp Gly Val Gly Asn Ser
    210                 215                 220
Ser Gly Asn Trp His Cys Asp Ser Thr Trp Met Gly Asp Arg Val Ile
225                 230                 235                 240
Thr Thr Ser Thr Arg Thr Trp Ala Leu Pro Thr Tyr Asn Asn His Leu
                245                 250                 255
Tyr Lys Gln Ile Ser Ser Gln Ser Gly Ala Ser Asn Asp Asn His Tyr
            260                 265                 270
Phe Gly Tyr Ser Thr Pro Trp Gly Tyr Phe Asp Phe Asn Arg Phe His
            275                 280                 285
Cys His Phe Ser Pro Arg Asp Trp Gln Arg Leu Ile Asn Asn Asn Trp
    290                 295                 300
Gly Phe Arg Pro Lys Arg Leu Asn Phe Lys Leu Phe Asn Ile Gln Val
305                 310                 315                 320
Lys Glu Val Thr Gln Asn Asp Gly Thr Thr Thr Ile Ala Asn Asn Leu
                325                 330                 335
Thr Ser Thr Val Gln Val Phe Thr Asp Ser Glu Tyr Gln Leu Pro Tyr
            340                 345                 350
Val Leu Gly Ser Ala His Gln Gly Cys Leu Pro Pro Phe Pro Ala Asp
            355                 360                 365
Val Phe Met Val Pro Gln Tyr Gly Tyr Leu Thr Leu Asn Asn Gly Ser
    370                 375                 380
Gln Ala Val Gly Arg Ser Ser Phe Tyr Cys Leu Glu Tyr Phe Pro Ser
385                 390                 395                 400
Gln Met Leu Arg Thr Gly Asn Asn Phe Thr Phe Ser Tyr Thr Phe Glu
                405                 410                 415
Asp Val Pro Phe His Ser Ser Tyr Ala His Ser Gln Ser Leu Asp Arg
```

```
                420             425             430
Leu Met Asn Pro Leu Ile Asp Gln Tyr Leu Tyr Tyr Leu Ser Arg Thr
            435                 440                 445

Asn Thr Pro Ser Gly Thr Thr Thr Gln Ser Arg Leu Gln Phe Ser Gln
450                 455                 460

Ala Gly Pro Ser Asn Met Arg Asp Gln Ser Arg Asn Trp Leu Pro Gly
465                 470                 475                 480

Pro Cys Tyr Arg Gln Gln Arg Val Ser Lys Thr Ser Ala Asp Asn Asn
                485                 490                 495

Asn Ser Glu Tyr Ser Trp Thr Gly Ala Thr Lys Tyr His Leu Asn Gly
            500                 505                 510

Arg Asp Ser Leu Val Asn Pro Gly Pro Ala Met Ala Ser His Lys Asp
        515                 520                 525

Asp Glu Glu Lys Phe Phe Pro Gln Ser Gly Val Leu Ile Phe Gly Lys
530                 535                 540

Gln Gly Ser Glu Lys Thr Asn Val Asp Ile Glu Lys Val Met Ile Thr
545                 550                 555                 560

Asp Glu Glu Glu Ile Arg Thr Thr Asn Pro Val Ala Thr Glu Gln Tyr
                565                 570                 575

Gly Ser Val Ser Thr Asn Leu Gln Arg Gly Asn Arg Gln Ala Ala Thr
            580                 585                 590

Ala Asp Val Asn Thr Gln Gly Val Leu Pro Gly Met Val Trp Gln Asp
        595                 600                 605

Arg Asp Val Tyr Leu Gln Gly Pro Ile Trp Ala Lys Ile Pro His Thr
610                 615                 620

Asp Gly His Phe His Pro Ser Pro Leu Met Gly Gly Phe Gly Leu Lys
625                 630                 635                 640

His Pro Pro Pro Gln Ile Leu Ile Lys Asn Thr Pro Val Pro Ala Asn
                645                 650                 655

Pro Ser Thr Thr Phe Ser Ala Ala Lys Phe Ala Ser Phe Ile Thr Gln
            660                 665                 670

Tyr Ser Thr Gly Gln Val Ser Val Glu Ile Glu Trp Glu Leu Gln Lys
        675                 680                 685

Glu Asn Ser Lys Arg Trp Asn Pro Glu Ile Gln Tyr Thr Ser Asn Tyr
690                 695                 700

Asn Lys Ser Val Asn Val Asp Phe Thr Val Asp Thr Asn Gly Val Tyr
705                 710                 715                 720

Ser Glu Pro Arg Pro Ile Gly Thr Arg Tyr Leu Thr Arg Asn Leu
                725                 730                 735

<210> SEQ ID NO 9
<211> LENGTH: 735
<212> TYPE: PRT
<213> ORGANISM: Adeno Associated Virus

<400> SEQUENCE: 9

Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro
            20                  25                  30

Lys Pro Ala Glu Arg His Lys Asp Asp Ser Arg Gly Leu Val Leu Pro
        35                  40                  45

Gly Tyr Lys Tyr Leu Gly Pro Phe Asn Gly Leu Asp Lys Gly Glu Pro
50                  55                  60
```

```
Val Asn Glu Ala Asp Ala Ala Leu Glu His Asp Lys Ala Tyr Asp
 65                  70                  75                  80

Arg Gln Leu Asp Ser Gly Asp Asn Pro Tyr Leu Lys Tyr Asn His Ala
                 85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Pro Val Lys Thr Ala Pro Gly Lys Lys Arg
130                 135                 140

Pro Val Glu His Ser Pro Val Glu Pro Asp Ser Ser Gly Thr Gly
145                 150                 155                 160

Lys Ala Gly Gln Gln Pro Ala Arg Lys Arg Leu Asn Phe Gly Gln Thr
                165                 170                 175

Gly Asp Ala Asp Ser Val Pro Asp Pro Gln Pro Leu Gly Gln Pro Pro
            180                 185                 190

Ala Ala Pro Ser Gly Leu Gly Thr Asn Thr Met Ala Thr Gly Ser Gly
        195                 200                 205

Ala Pro Met Ala Asp Asn Asn Glu Gly Ala Asp Gly Val Gly Asn Ser
210                 215                 220

Ser Gly Asn Trp His Cys Asp Ser Thr Trp Met Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
            260                 265                 270

Phe Gly Tyr Ser Thr Pro Trp Gly Tyr Phe Asp Phe Asn Arg Phe His
        275                 280                 285

Cys His Phe Ser Pro Arg Asp Trp Gln Arg Leu Ile Asn Asn Asn Trp
290                 295                 300

Gly Phe Arg Pro Lys Arg Leu Asn Phe Lys Leu Phe Asn Ile Gln Val
305                 310                 315                 320

Lys Glu Val Thr Gln Asn Asp Gly Thr Thr Thr Ile Ala Asn Asn Leu
                325                 330                 335

Thr Ser Thr Val Gln Val Phe Thr Asp Ser Glu Tyr Gln Leu Pro Tyr
            340                 345                 350

Val Leu Gly Ser Ala His Gln Gly Cys Leu Pro Pro Phe Pro Ala Asp
        355                 360                 365

Val Phe Met Val Pro Gln Tyr Gly Tyr Leu Thr Leu Asn Asn Gly Ser
370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Thr Phe Ser Tyr Thr Phe Glu
                405                 410                 415

Asp Val Pro Phe His Ser Ser Tyr Ala His Ser Gln Ser Leu Asp Arg
            420                 425                 430

Leu Met Asn Pro Leu Ile Asp Gln Tyr Leu Tyr Tyr Leu Ser Arg Thr
        435                 440                 445

Asn Thr Pro Ser Gly Thr Thr Thr Gln Ser Arg Leu Gln Phe Ser Gln
450                 455                 460

Ala Gly Pro Ala Gly Met Ser Val Gln Ser Arg Asn Trp Leu Pro Gly
465                 470                 475                 480

Pro Cys Tyr Arg Gln Gln Arg Val Ser Lys Thr Ser Ala Asp Asn Asn
```

-continued

```
                485                 490                 495
Asn Ser Glu Tyr Ser Trp Thr Gly Ala Thr Lys Tyr His Leu Asn Gly
            500                 505                 510

Arg Asp Ser Leu Val Asn Pro Gly Pro Ala Met Ala Ser His Lys Asp
        515                 520                 525

Asp Glu Glu Lys Phe Phe Pro Gln Ser Gly Val Leu Ile Phe Gly Lys
    530                 535                 540

Gln Gly Ser Glu Lys Thr Asn Val Asp Ile Glu Lys Val Met Ile Thr
545                 550                 555                 560

Asp Glu Glu Glu Ile Arg Thr Thr Asn Pro Val Ala Thr Glu Gln Tyr
                565                 570                 575

Gly Ser Val Ser Thr Asn Leu Gln Arg Gly Asn Arg Gln Ala Ala Thr
            580                 585                 590

Ala Asp Val Asn Thr Gln Gly Val Leu Pro Gly Met Val Trp Gln Asp
        595                 600                 605

Arg Asp Val Tyr Leu Gln Gly Pro Ile Trp Ala Lys Ile Pro His Thr
    610                 615                 620

Asp Gly His Phe His Pro Ser Pro Leu Met Gly Gly Phe Gly Leu Lys
625                 630                 635                 640

His Pro Pro Pro Gln Ile Leu Ile Lys Asn Thr Pro Val Pro Ala Asn
                645                 650                 655

Pro Ser Thr Thr Phe Ser Ala Ala Lys Phe Ala Ser Phe Ile Thr Gln
            660                 665                 670

Tyr Ser Thr Gly Gln Val Ser Val Glu Ile Glu Trp Glu Leu Gln Lys
        675                 680                 685

Glu Asn Ser Lys Arg Trp Asn Pro Glu Ile Gln Tyr Thr Ser Asn Tyr
    690                 695                 700

Asn Lys Ser Val Asn Val Asp Phe Thr Val Asp Thr Asn Gly Val Tyr
705                 710                 715                 720

Ser Glu Pro Arg Pro Ile Gly Thr Arg Tyr Leu Thr Arg Asn Leu
                725                 730                 735

<210> SEQ ID NO 10
<211> LENGTH: 735
<212> TYPE: PRT
<213> ORGANISM: Adeno Associated Virus

<400> SEQUENCE: 10

Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro Pro
            20                  25                  30

Lys Pro Ala Glu Arg His Lys Asp Asp Ser Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Glu Ala Asp Ala Ala Ala Leu Glu His Asp Lys Ala Tyr Asp
65                  70                  75                  80

Arg Gln Leu Asp Ser Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Val Leu Glu Pro
        115                 120                 125
```

-continued

Leu Gly Leu Val Glu Glu Pro Val Lys Thr Ala Pro Gly Lys Lys Arg
130                 135                 140

Pro Val Glu His Ser Pro Val Glu Pro Asp Ser Ser Gly Thr Gly
145                 150                 155                 160

Lys Ala Gly Gln Gln Pro Ala Arg Lys Arg Leu Asn Phe Gly Gln Thr
                165                 170                 175

Gly Asp Ala Asp Ser Val Pro Asp Pro Gln Pro Leu Gly Gln Pro Pro
            180                 185                 190

Ala Ala Pro Ser Gly Leu Gly Thr Asn Thr Met Ala Thr Gly Ser Gly
        195                 200                 205

Ala Pro Met Ala Asp Asn Asn Glu Gly Ala Asp Gly Val Gly Asn Ser
210                 215                 220

Ser Gly Asn Trp His Cys Asp Ser Thr Trp Met Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
            260                 265                 270

Phe Gly Tyr Ser Thr Pro Trp Gly Tyr Phe Asp Phe Asn Arg Phe His
        275                 280                 285

Cys His Phe Ser Pro Arg Asp Trp Gln Arg Leu Ile Asn Asn Asn Trp
290                 295                 300

Gly Phe Arg Pro Lys Arg Leu Asn Phe Lys Leu Phe Asn Ile Gln Val
305                 310                 315                 320

Lys Glu Val Thr Gln Asn Asp Gly Thr Thr Thr Ile Ala Asn Asn Leu
                325                 330                 335

Thr Ser Thr Val Gln Val Phe Thr Asp Ser Glu Tyr Gln Leu Pro Tyr
            340                 345                 350

Val Leu Gly Ser Ala His Gln Gly Cys Leu Pro Pro Phe Pro Ala Asp
        355                 360                 365

Val Phe Met Val Pro Gln Tyr Gly Tyr Leu Thr Leu Asn Asn Gly Ser
370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Thr Phe Ser Tyr Thr Phe Glu
                405                 410                 415

Asp Val Pro Phe His Ser Ser Tyr Ala His Ser Gln Ser Leu Asp Arg
            420                 425                 430

Leu Met Asn Pro Leu Ile Asp Gln Tyr Leu Tyr Tyr Leu Ser Arg Thr
        435                 440                 445

Asn Thr Pro Ser Gly Thr Thr Thr Gln Ser Arg Leu Gln Phe Ser Gln
450                 455                 460

Ala Gly Pro Asn Thr Met Ala Asn Gln Ser Arg Asn Trp Leu Pro Gly
465                 470                 475                 480

Pro Cys Tyr Arg Gln Gln Arg Val Ser Lys Thr Ser Ala Asp Asn Asn
                485                 490                 495

Asn Ser Glu Tyr Ser Trp Thr Gly Ala Thr Lys Tyr His Leu Asn Gly
            500                 505                 510

Arg Asp Ser Leu Val Asn Pro Gly Pro Ala Met Ala Ser His Lys Asp
        515                 520                 525

Asp Glu Glu Lys Phe Phe Pro Gln Ser Gly Val Leu Ile Phe Gly Lys
530                 535                 540

Gln Gly Ser Glu Lys Thr Asn Val Asp Ile Glu Lys Val Met Ile Thr

```
                545                 550                 555                 560
Asp Glu Glu Glu Ile Arg Thr Thr Asn Pro Val Ala Thr Gln Tyr
                    565                 570                 575
Gly Ser Val Ser Thr Asn Leu Gln Arg Gly Asn Arg Gln Ala Ala Thr
                580                 585                 590
Ala Asp Val Asn Thr Gln Gly Val Leu Pro Gly Met Val Trp Gln Asp
                595                 600                 605
Arg Asp Val Tyr Leu Gln Gly Pro Ile Trp Ala Lys Ile Pro His Thr
                610                 615                 620
Asp Gly His Phe His Pro Ser Pro Leu Met Gly Gly Phe Gly Leu Lys
625                 630                 635                 640
His Pro Pro Pro Gln Ile Leu Ile Lys Asn Thr Pro Val Pro Ala Asn
                    645                 650                 655
Pro Ser Thr Thr Phe Ser Ala Ala Lys Phe Ala Ser Phe Ile Thr Gln
                    660                 665                 670
Tyr Ser Thr Gly Gln Val Ser Val Glu Ile Glu Trp Glu Leu Gln Lys
                    675                 680                 685
Glu Asn Ser Lys Arg Trp Asn Pro Glu Ile Gln Tyr Thr Ser Asn Tyr
                690                 695                 700
Asn Lys Ser Val Asn Val Asp Phe Thr Val Asp Thr Asn Gly Val Tyr
705                 710                 715                 720
Ser Glu Pro Arg Pro Ile Gly Thr Arg Tyr Leu Thr Arg Asn Leu
                    725                 730                 735

<210> SEQ ID NO 11
<211> LENGTH: 735
<212> TYPE: PRT
<213> ORGANISM: Adeno Associated Virus

<400> SEQUENCE: 11

Met Ala Ala Asp Gly Tyr Leu Pro Asp Trp Leu Glu Asp Thr Leu Ser
1               5                   10                  15
Glu Gly Ile Arg Gln Trp Trp Lys Leu Lys Pro Gly Pro Pro Pro Pro
                20                  25                  30
Lys Pro Ala Glu Arg His Lys Asp Asp Ser Arg Gly Leu Val Leu Pro
                35                  40                  45
Gly Tyr Lys Tyr Leu Gly Pro Phe Asn Gly Leu Asp Lys Gly Glu Pro
            50                  55                  60
Val Asn Glu Ala Asp Ala Ala Ala Leu Glu His Asp Lys Ala Tyr Asp
65                  70                  75                  80
Arg Gln Leu Asp Ser Gly Asp Asn Pro Tyr Leu Lys Tyr Asn His Ala
                85                  90                  95
Asp Ala Glu Phe Gln Glu Arg Leu Lys Glu Asp Thr Ser Phe Gly Gly
                100                 105                 110
Asn Leu Gly Arg Ala Val Phe Gln Ala Lys Lys Arg Val Leu Glu Pro
            115                 120                 125
Leu Gly Leu Val Glu Glu Pro Val Lys Thr Ala Pro Gly Lys Lys Arg
130                 135                 140
Pro Val Glu His Ser Pro Val Glu Pro Asp Ser Ser Ser Gly Thr Gly
145                 150                 155                 160
Lys Ala Gly Gln Gln Pro Ala Arg Lys Arg Leu Asn Phe Gly Gln Thr
                165                 170                 175
Gly Asp Ala Asp Ser Val Pro Asp Pro Gln Pro Leu Gly Gln Pro Pro
            180                 185                 190
```

```
Ala Ala Pro Ser Gly Leu Gly Thr Asn Thr Met Ala Thr Gly Ser Gly
        195                 200                 205
Ala Pro Met Ala Asp Asn Asn Glu Gly Ala Asp Gly Val Gly Asn Ser
210                 215                 220
Ser Gly Asn Trp His Cys Asp Ser Thr Trp Met Gly Asp Arg Val Ile
225                 230                 235                 240
Thr Thr Ser Thr Arg Thr Trp Ala Leu Pro Thr Tyr Asn Asn His Leu
                245                 250                 255
Tyr Lys Gln Ile Ser Ser Gln Ser Gly Ala Ser Asn Asp Asn His Tyr
            260                 265                 270
Phe Gly Tyr Ser Thr Pro Trp Gly Tyr Phe Asp Phe Asn Arg Phe His
        275                 280                 285
Cys His Phe Ser Pro Arg Asp Trp Gln Arg Leu Ile Asn Asn Asn Trp
    290                 295                 300
Gly Phe Arg Pro Lys Arg Leu Asn Phe Lys Leu Phe Asn Ile Gln Val
305                 310                 315                 320
Lys Glu Val Thr Gln Asn Asp Gly Thr Thr Thr Ile Ala Asn Asn Leu
                325                 330                 335
Thr Ser Thr Val Gln Val Phe Thr Asp Ser Glu Tyr Gln Leu Pro Tyr
                340                 345                 350
Val Leu Gly Ser Ala His Gln Gly Cys Leu Pro Pro Phe Pro Ala Asp
        355                 360                 365
Val Phe Met Val Pro Gln Tyr Gly Tyr Leu Thr Leu Asn Asn Gly Ser
        370                 375                 380
Gln Ala Val Gly Arg Ser Ser Phe Tyr Cys Leu Glu Tyr Phe Pro Ser
385                 390                 395                 400
Gln Met Leu Arg Thr Gly Asn Asn Phe Thr Phe Ser Tyr Thr Phe Glu
                405                 410                 415
Asp Val Pro Phe His Ser Ser Tyr Ala His Ser Gln Ser Leu Asp Arg
                420                 425                 430
Leu Met Asn Pro Leu Ile Asp Gln Tyr Leu Tyr Tyr Leu Ser Arg Thr
                435                 440                 445
Asn Thr Pro Ser Gly Thr Thr Thr Gln Ser Arg Leu Gln Phe Ser Gln
450                 455                 460
Ala Gly Pro Ser Asn Met Ala Val Gln Ser Arg Asn Trp Leu Pro Gly
465                 470                 475                 480
Pro Cys Tyr Arg Gln Gln Arg Val Ser Lys Thr Ser Ala Asp Asn Asn
                485                 490                 495
Asn Ser Glu Tyr Ser Trp Thr Gly Ala Thr Lys Tyr His Leu Asn Gly
            500                 505                 510
Arg Asp Ser Leu Val Asn Pro Gly Pro Ala Met Ala Ser His Lys Asp
            515                 520                 525
Asp Glu Glu Lys Phe Phe Pro Gln Ser Gly Val Leu Ile Phe Gly Lys
        530                 535                 540
Gln Gly Ser Glu Lys Thr Asn Val Asp Ile Glu Lys Val Met Ile Thr
545                 550                 555                 560
Asp Glu Glu Glu Ile Arg Thr Thr Asn Pro Val Ala Thr Glu Gln Tyr
                565                 570                 575
Gly Ser Val Ser Thr Asn Leu Gln Arg Gly Asn Arg Gln Ala Ala Thr
            580                 585                 590
Ala Asp Val Asn Thr Gln Gly Val Leu Pro Gly Met Val Trp Gln Asp
        595                 600                 605
Arg Asp Val Tyr Leu Gln Gly Pro Ile Trp Ala Lys Ile Pro His Thr
```

```
                610               615                620

Asp Gly His Phe His Pro Ser Pro Leu Met Gly Gly Phe Gly Leu Lys
625                 630                 635                 640

His Pro Pro Pro Gln Ile Leu Ile Lys Asn Thr Pro Val Pro Ala Asn
                645                 650                 655

Pro Ser Thr Thr Phe Ser Ala Ala Lys Phe Ala Ser Phe Ile Thr Gln
                660                 665                 670

Tyr Ser Thr Gly Gln Val Ser Val Glu Ile Glu Trp Glu Leu Gln Lys
                675                 680                 685

Glu Asn Ser Lys Arg Trp Asn Pro Glu Ile Gln Tyr Thr Ser Asn Tyr
690                 695                 700

Asn Lys Ser Val Asn Val Asp Phe Thr Val Asp Thr Asn Gly Val Tyr
705                 710                 715                 720

Ser Glu Pro Arg Pro Ile Gly Thr Arg Tyr Leu Thr Arg Asn Leu
                725                 730                 735

<210> SEQ ID NO 12
<211> LENGTH: 735
<212> TYPE: PRT
<213> ORGANISM: Adeno Associated Virus

<400> SEQUENCE: 12

Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro Pro
                20                  25                  30

Lys Pro Ala Glu Arg His Lys Asp Asp Ser Arg Gly Leu Val Leu Pro
                35                  40                  45

Gly Tyr Lys Tyr Leu Gly Pro Phe Asn Gly Leu Asp Lys Gly Glu Pro
            50                  55                  60

Val Asn Glu Ala Asp Ala Ala Leu Glu His Asp Lys Ala Tyr Asp
65                  70                  75                  80

Arg Gln Leu Asp Ser Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
                100                 105                 110

Asn Leu Gly Arg Ala Val Phe Gln Ala Lys Lys Arg Val Leu Glu Pro
            115                 120                 125

Leu Gly Leu Val Glu Glu Pro Val Lys Thr Ala Pro Gly Lys Lys Arg
130                 135                 140

Pro Val Glu His Ser Pro Val Glu Pro Asp Ser Ser Ser Gly Thr Gly
145                 150                 155                 160

Lys Ala Gly Gln Gln Pro Ala Arg Lys Arg Leu Asn Phe Gly Gln Thr
                165                 170                 175

Gly Asp Ala Asp Ser Val Pro Asp Pro Gln Pro Leu Gly Gln Pro Pro
                180                 185                 190

Ala Ala Pro Ser Gly Leu Gly Thr Asn Thr Met Ala Thr Gly Ser Gly
            195                 200                 205

Ala Pro Met Ala Asp Asn Asn Glu Gly Ala Asp Gly Val Gly Asn Ser
210                 215                 220

Ser Gly Asn Trp His Cys Asp Ser Thr Trp Met Gly Asp Arg Val Ile
225                 230                 235                 240

Thr Thr Ser Thr Arg Thr Trp Ala Leu Pro Thr Tyr Asn Asn His Leu
                245                 250                 255
```

-continued

Tyr Lys Gln Ile Ser Ser Gln Ser Gly Ala Ser Asn Asp Asn His Tyr
            260             265             270

Phe Gly Tyr Ser Thr Pro Trp Gly Tyr Phe Asp Phe Asn Arg Phe His
        275             280             285

Cys His Phe Ser Pro Arg Asp Trp Gln Arg Leu Ile Asn Asn Asn Trp
    290             295             300

Gly Phe Arg Pro Lys Arg Leu Asn Phe Lys Leu Phe Asn Ile Gln Val
305             310             315             320

Lys Glu Val Thr Gln Asn Asp Gly Thr Thr Thr Ile Ala Asn Asn Leu
            325             330             335

Thr Ser Thr Val Gln Val Phe Thr Asp Ser Glu Tyr Gln Leu Pro Tyr
            340             345             350

Val Leu Gly Ser Ala His Gln Gly Cys Leu Pro Pro Phe Pro Ala Asp
            355             360             365

Val Phe Met Val Pro Gln Tyr Gly Tyr Leu Thr Leu Asn Asn Gly Ser
        370             375             380

Gln Ala Val Gly Arg Ser Ser Phe Tyr Cys Leu Glu Tyr Phe Pro Ser
385             390             395             400

Gln Met Leu Arg Thr Gly Asn Asn Phe Thr Phe Ser Tyr Thr Phe Glu
            405             410             415

Asp Val Pro Phe His Ser Ser Tyr Ala His Ser Gln Ser Leu Asp Arg
            420             425             430

Leu Met Asn Pro Leu Ile Asp Gln Tyr Leu Tyr Tyr Leu Ser Arg Thr
        435             440             445

Asn Thr Pro Ser Gly Thr Thr Thr Gln Ser Arg Leu Gln Phe Ser Gln
    450             455             460

Ala Gly Ala Ser Thr Met Ala Asn Gln Ala Arg Asn Trp Leu Pro Gly
465             470             475             480

Pro Cys Tyr Arg Gln Gln Arg Val Ser Lys Thr Ser Ala Asp Asn Asn
            485             490             495

Asn Ser Glu Tyr Ser Trp Thr Gly Ala Thr Lys Tyr His Leu Asn Gly
        500             505             510

Arg Asp Ser Leu Val Asn Pro Gly Pro Ala Met Ala Ser His Lys Asp
    515             520             525

Asp Glu Glu Lys Phe Phe Pro Gln Ser Gly Val Leu Ile Phe Gly Lys
530             535             540

Gln Gly Ser Glu Lys Thr Asn Val Asp Ile Glu Lys Val Met Ile Thr
545             550             555             560

Asp Glu Glu Glu Ile Arg Thr Thr Asn Pro Val Ala Thr Glu Gln Tyr
            565             570             575

Gly Ser Val Ser Thr Asn Leu Gln Arg Gly Asn Arg Gln Ala Ala Thr
        580             585             590

Ala Asp Val Asn Thr Gln Gly Val Leu Pro Gly Met Val Trp Gln Asp
    595             600             605

Arg Asp Val Tyr Leu Gln Gly Pro Ile Trp Ala Lys Ile Pro His Thr
610             615             620

Asp Gly His Phe His Pro Ser Pro Leu Met Gly Gly Phe Gly Leu Lys
625             630             635             640

His Pro Pro Pro Gln Ile Leu Ile Lys Asn Thr Pro Val Pro Ala Asn
            645             650             655

Pro Ser Thr Thr Phe Ser Ala Ala Lys Phe Ala Ser Phe Ile Thr Gln
        660             665             670

Tyr Ser Thr Gly Gln Val Ser Val Glu Ile Glu Trp Glu Leu Gln Lys

```
                    675                 680                 685
Glu Asn Ser Lys Arg Trp Asn Pro Glu Ile Gln Tyr Thr Ser Asn Tyr
        690                 695                 700

Asn Lys Ser Val Asn Val Asp Phe Thr Val Asp Thr Asn Gly Val Tyr
705                 710                 715                 720

Ser Glu Pro Arg Pro Ile Gly Thr Arg Tyr Leu Thr Arg Asn Leu
                725                 730                 735

<210> SEQ ID NO 13
<211> LENGTH: 735
<212> TYPE: PRT
<213> ORGANISM: Adeno Associated Virus

<400> SEQUENCE: 13

Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro Pro
            20                  25                  30

Lys Pro Ala Glu Arg His Lys Asp Asp Ser Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Glu Ala Asp Ala Ala Ala Leu Glu His Asp Lys Ala Tyr Asp
65                  70                  75                  80

Arg Gln Leu Asp Ser Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Pro Val Lys Thr Ala Pro Gly Lys Lys Arg
    130                 135                 140

Pro Val Glu His Ser Pro Val Glu Pro Asp Ser Ser Ser Gly Thr Gly
145                 150                 155                 160

Lys Ala Gly Gln Gln Pro Ala Arg Lys Arg Leu Asn Phe Gly Gln Thr
                165                 170                 175

Gly Asp Ala Asp Ser Val Pro Asp Pro Gln Pro Leu Gly Gln Pro Pro
            180                 185                 190

Ala Ala Pro Ser Gly Leu Gly Thr Asn Thr Met Ala Thr Gly Ser Gly
        195                 200                 205

Ala Pro Met Ala Asp Asn Asn Glu Gly Ala Asp Gly Val Gly Asn Ser
    210                 215                 220

Ser Gly Asn Trp His Cys Asp Ser Thr Trp Met Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
            260                 265                 270

Phe Gly Tyr Ser Thr Pro Trp Gly Tyr Phe Asp Phe Asn Arg Phe His
        275                 280                 285

Cys His Phe Ser Pro Arg Asp Trp Gln Arg Leu Ile Asn Asn Asn Trp
    290                 295                 300

Gly Phe Arg Pro Lys Arg Leu Asn Phe Lys Leu Phe Asn Ile Gln Val
305                 310                 315                 320
```

-continued

```
Lys Glu Val Thr Gln Asn Asp Gly Thr Thr Thr Ile Ala Asn Asn Leu
                325                 330                 335
Thr Ser Thr Val Gln Val Phe Thr Asp Ser Glu Tyr Gln Leu Pro Tyr
            340                 345                 350
Val Leu Gly Ser Ala His Gln Gly Cys Leu Pro Pro Phe Pro Ala Asp
        355                 360                 365
Val Phe Met Val Pro Gln Tyr Gly Tyr Leu Thr Leu Asn Asn Gly Ser
    370                 375                 380
Gln Ala Val Gly Arg Ser Ser Phe Tyr Cys Leu Glu Tyr Phe Pro Ser
385                 390                 395                 400
Gln Met Leu Arg Thr Gly Asn Asn Phe Thr Phe Ser Tyr Thr Phe Glu
                405                 410                 415
Asp Val Pro Phe His Ser Ser Tyr Ala His Ser Gln Ser Leu Asp Arg
            420                 425                 430
Leu Met Asn Pro Leu Ile Asp Gln Tyr Leu Tyr Tyr Leu Ser Arg Thr
        435                 440                 445
Asn Thr Pro Ser Gly Thr Thr Thr Gln Ser Arg Leu Gln Phe Ser Gln
    450                 455                 460
Ala Gly Ala Ser Asp Met Ala Val Gln Gly Arg Asn Trp Leu Pro Gly
465                 470                 475                 480
Pro Cys Tyr Arg Gln Gln Arg Val Ser Lys Thr Ser Ala Asp Asn Asn
                485                 490                 495
Asn Ser Glu Tyr Ser Trp Thr Gly Ala Thr Lys Tyr His Leu Asn Gly
            500                 505                 510
Arg Asp Ser Leu Val Asn Pro Gly Pro Ala Met Ala Ser His Lys Asp
        515                 520                 525
Asp Glu Glu Lys Phe Phe Pro Gln Ser Gly Val Leu Ile Phe Gly Lys
    530                 535                 540
Gln Gly Ser Glu Lys Thr Asn Val Asp Ile Glu Lys Val Met Ile Thr
545                 550                 555                 560
Asp Glu Glu Glu Ile Arg Thr Thr Asn Pro Val Ala Thr Glu Gln Tyr
                565                 570                 575
Gly Ser Val Ser Thr Asn Leu Gln Arg Gly Asn Arg Gln Ala Ala Thr
            580                 585                 590
Ala Asp Val Asn Thr Gln Gly Val Leu Pro Gly Met Val Trp Gln Asp
        595                 600                 605
Arg Asp Val Tyr Leu Gln Gly Pro Ile Trp Ala Lys Ile Pro His Thr
    610                 615                 620
Asp Gly His Phe His Pro Ser Pro Leu Met Gly Gly Phe Gly Leu Lys
625                 630                 635                 640
His Pro Pro Pro Gln Ile Leu Ile Lys Asn Thr Pro Val Pro Ala Asn
                645                 650                 655
Pro Ser Thr Thr Phe Ser Ala Ala Lys Phe Ala Ser Phe Ile Thr Gln
            660                 665                 670
Tyr Ser Thr Gly Gln Val Ser Val Glu Ile Glu Trp Glu Leu Gln Lys
        675                 680                 685
Glu Asn Ser Lys Arg Trp Asn Pro Glu Ile Gln Tyr Thr Ser Asn Tyr
    690                 695                 700
Asn Lys Ser Val Asn Val Asp Phe Thr Val Asp Thr Asn Gly Val Tyr
705                 710                 715                 720
Ser Glu Pro Arg Pro Ile Gly Thr Arg Tyr Leu Thr Arg Asn Leu
                725                 730                 735
```

<210> SEQ ID NO 14
<211> LENGTH: 750
<212> TYPE: PRT
<213> ORGANISM: Adeno associated virus

<400> SEQUENCE: 14

Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro
            20                  25                  30

Lys Pro Ala Glu Arg His Lys Asp Asp Ser Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Glu Ala Asp Ala Ala Ala Leu Glu His Asp Lys Ala Tyr Asp
65                  70                  75                  80

Arg Gln Leu Asp Ser Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Pro Val Lys Thr Ala Pro Gly Lys Lys Arg
    130                 135                 140

Pro Val Glu His Ser Pro Val Glu Pro Asp Ser Ser Ser Gly Thr Gly
145                 150                 155                 160

Lys Ala Gly Gln Gln Pro Ala Arg Lys Arg Leu Asn Phe Gly Gln Thr
                165                 170                 175

Gly Asp Ala Asp Ser Val Pro Asp Pro Gln Pro Leu Gly Gln Pro Pro
            180                 185                 190

Ala Ala Pro Ser Gly Leu Gly Thr Asn Thr Met Ala Thr Gly Ser Gly
        195                 200                 205

Ala Pro Met Ala Asp Asn Asn Glu Gly Ala Asp Gly Val Gly Asn Ser
    210                 215                 220

Ser Gly Asn Trp His Cys Asp Ser Thr Trp Met Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
            260                 265                 270

Phe Gly Tyr Ser Thr Pro Trp Gly Tyr Phe Asp Phe Asn Arg Phe His
        275                 280                 285

Cys His Phe Ser Pro Arg Asp Trp Gln Arg Leu Ile Asn Asn Asn Trp
    290                 295                 300

Gly Phe Arg Pro Lys Arg Leu Asn Phe Lys Leu Phe Asn Ile Gln Val
305                 310                 315                 320

Lys Glu Val Thr Gln Asn Asp Gly Thr Thr Thr Ile Ala Asn Asn Leu
                325                 330                 335

Thr Ser Thr Val Gln Val Phe Thr Asp Ser Glu Tyr Gln Leu Pro Tyr
            340                 345                 350

Val Leu Gly Ser Ala His Gln Gly Cys Leu Pro Pro Phe Pro Ala Asp
        355                 360                 365

Val Phe Met Val Pro Gln Tyr Gly Tyr Leu Thr Leu Asn Asn Gly Ser
    370                 375                 380

```
Gln Ala Val Gly Arg Ser Ser Phe Tyr Cys Leu Glu Tyr Phe Pro Ser
385                 390                 395                 400

Gln Met Leu Arg Thr Gly Asn Asn Phe Thr Phe Ser Tyr Thr Phe Glu
            405                 410                 415

Asp Val Pro Phe His Ser Ser Tyr Ala His Ser Gln Ser Leu Asp Arg
        420                 425                 430

Leu Met Asn Pro Leu Ile Asp Gln Tyr Leu Tyr Tyr Leu Ser Arg Thr
    435                 440                 445

Asn Thr Pro Ser Gly Thr Thr Thr Gln Ser Arg Leu Gln Phe Ser Gln
450                 455                 460

Ala Gly Ala Ser Asp Ile Arg Asp Gln Ser Arg Asn Trp Leu Pro Gly
465                 470                 475                 480

Pro Cys Tyr Arg Gln Gln Arg Val Ser Lys Thr Ser Ala Asp Asn Asn
            485                 490                 495

Asn Ser Glu Phe Ala Trp Thr Gly Ala Thr Lys Tyr His Leu Asn Gly
        500                 505                 510

Arg Asn Ser Leu Val Asn Pro Gly Pro Ala Met Ala Ser His Lys Asp
    515                 520                 525

Asp Glu Glu Lys Phe Phe Pro Gln Ser Gly Val Leu Ile Phe Gly Lys
530                 535                 540

Gln Gly Ser Glu Lys Thr Asn Val Asp Ile Glu Lys Val Met Ile Thr
545                 550                 555                 560

Asp Glu Glu Glu Ile Arg Thr Thr Asn Pro Val Ala Thr Glu Gln Tyr
            565                 570                 575

Gly Ser Val Ser Thr Asn Leu Gln Arg Gly Asn Arg Gln Ala Ala Thr
        580                 585                 590

Ala Asp Val Asn Thr Gln Gly Val Leu Pro Gly Met Val Trp Gln Asp
    595                 600                 605

Arg Asp Val Tyr Leu Gln Gly Pro Ile Trp Ala Lys Ile Pro His Thr
610                 615                 620

Asp Gly His Phe His Pro Ser Pro Leu Met Gly Gly Phe Gly Leu Lys
625                 630                 635                 640

His Pro Pro Pro Gln Ile Leu Ile Lys Asn Thr Pro Val Pro Ala Asn
            645                 650                 655

Pro Ser Thr Thr Phe Ser Ala Ala Lys Phe Ala Ser Phe Ile Thr Gln
        660                 665                 670

Tyr Ser Thr Gly Gln Val Ser Val Glu Ile Glu Trp Glu Leu Gln Lys
    675                 680                 685

Glu Asn Ser Lys Arg Trp Asn Pro Glu Ile Gln Tyr Thr Ser Asn Tyr
690                 695                 700

Asn Lys Ser Val Asn Val Asp Phe Thr Val Asp Thr Asn Gly Val Tyr
705                 710                 715                 720

Ser Glu Pro Arg Pro Ile Gly Thr Arg Tyr Leu Thr Arg Asn Leu Ser
            725                 730                 735

Glu Pro Arg Pro Ile Gly Thr Arg Tyr Leu Thr Arg Asn Leu
        740                 745                 750

<210> SEQ ID NO 15
<211> LENGTH: 750
<212> TYPE: PRT
<213> ORGANISM: Adeno Associated Virus

<400> SEQUENCE: 15

Met Ala Ala Asp Gly Tyr Leu Pro Asp Trp Leu Glu Asp Thr Leu Ser
1               5                   10                  15
```

```
Glu Gly Ile Arg Gln Trp Trp Lys Leu Lys Pro Gly Pro Pro Pro
            20                  25                  30
Lys Pro Ala Glu Arg His Lys Asp Asp Ser Arg Gly Leu Val Leu Pro
         35                  40                  45
Gly Tyr Lys Tyr Leu Gly Pro Phe Asn Gly Leu Asp Lys Gly Glu Pro
 50                  55                  60
Val Asn Glu Ala Asp Ala Ala Leu Glu His Asp Lys Ala Tyr Asp
 65                  70                  75                  80
Arg Gln Leu Asp Ser Gly Asp Asn Pro Tyr Leu Lys Tyr Asn His Ala
             85                  90                  95
Asp Ala Glu Phe Gln Glu Arg Leu Lys Glu Asp Thr Ser Phe Gly Gly
            100                 105                 110
Asn Leu Gly Arg Ala Val Phe Gln Ala Lys Lys Arg Val Leu Glu Pro
        115                 120                 125
Leu Gly Leu Val Glu Glu Pro Val Lys Thr Ala Pro Gly Lys Lys Arg
130                 135                 140
Pro Val Glu His Ser Pro Val Glu Pro Asp Ser Ser Gly Thr Gly
145                 150                 155                 160
Lys Ala Gly Gln Gln Pro Ala Arg Lys Arg Leu Asn Phe Gly Gln Thr
            165                 170                 175
Gly Asp Ala Asp Ser Val Pro Asp Pro Gln Pro Leu Gly Gln Pro Pro
        180                 185                 190
Ala Ala Pro Ser Gly Leu Gly Thr Asn Thr Met Ala Thr Gly Ser Gly
        195                 200                 205
Ala Pro Met Ala Asp Asn Asn Glu Gly Ala Asp Gly Val Gly Asn Ser
        210                 215                 220
Ser Gly Asn Trp His Cys Asp Ser Thr Trp Met Gly Asp Arg Val Ile
225                 230                 235                 240
Thr Thr Ser Thr Arg Thr Trp Ala Leu Pro Thr Tyr Asn Asn His Leu
                245                 250                 255
Tyr Lys Gln Ile Ser Ser Gln Ser Gly Ala Ser Asn Asp Asn His Tyr
            260                 265                 270
Phe Gly Tyr Ser Thr Pro Trp Gly Tyr Phe Asp Phe Asn Arg Phe His
        275                 280                 285
Cys His Phe Ser Pro Arg Asp Trp Gln Arg Leu Ile Asn Asn Asn Trp
        290                 295                 300
Gly Phe Arg Pro Lys Arg Leu Asn Phe Lys Leu Phe Asn Ile Gln Val
305                 310                 315                 320
Lys Glu Val Thr Gln Asn Asp Gly Thr Thr Thr Ile Ala Asn Asn Leu
                325                 330                 335
Thr Ser Thr Val Gln Val Phe Thr Asp Ser Glu Tyr Gln Leu Pro Tyr
            340                 345                 350
Val Leu Gly Ser Ala His Gln Gly Cys Leu Pro Pro Phe Pro Ala Asp
        355                 360                 365
Val Phe Met Val Pro Gln Tyr Gly Tyr Leu Thr Leu Asn Asn Gly Ser
        370                 375                 380
Gln Ala Val Gly Arg Ser Ser Phe Tyr Cys Leu Glu Tyr Phe Pro Ser
385                 390                 395                 400
Gln Met Leu Arg Thr Gly Asn Asn Phe Thr Phe Ser Tyr Thr Phe Glu
                405                 410                 415
Asp Val Pro Phe His Ser Ser Tyr Ala His Ser Gln Ser Leu Asp Arg
            420                 425                 430
```

-continued

Leu Met Asn Pro Leu Ile Asp Gln Tyr Leu Tyr Tyr Leu Ser Arg Thr
                435                 440                 445

Asn Thr Pro Ser Gly Thr Thr Thr Gln Ser Arg Leu Gln Phe Ser Val
        450                 455                 460

Ala Gly Pro Ser Asn Met Ala Val Gln Gly Arg Asn Trp Leu Pro Gly
465                 470                 475                 480

Pro Cys Tyr Arg Gln Gln Arg Val Ser Lys Thr Ser Ala Asp Asn Asn
                485                 490                 495

Asn Ser Glu Phe Ala Trp Thr Gly Ala Thr Lys Tyr His Leu Asn Gly
            500                 505                 510

Arg Asn Ser Leu Val Asn Pro Gly Pro Ala Met Ala Ser His Lys Asp
        515                 520                 525

Asp Glu Glu Lys Phe Phe Pro Gln Ser Gly Val Leu Ile Phe Gly Lys
    530                 535                 540

Gln Gly Ser Glu Lys Thr Asn Val Asp Ile Glu Lys Val Met Ile Thr
545                 550                 555                 560

Asp Glu Glu Glu Ile Arg Thr Thr Asn Pro Val Ala Thr Glu Gln Tyr
                565                 570                 575

Gly Ser Val Ser Thr Asn Leu Gln Arg Gly Asn Arg Gln Ala Ala Thr
            580                 585                 590

Ala Asp Val Asn Thr Gln Gly Val Leu Pro Gly Met Val Trp Gln Asp
        595                 600                 605

Arg Asp Val Tyr Leu Gln Gly Pro Ile Trp Ala Lys Ile Pro His Thr
    610                 615                 620

Asp Gly His Phe His Pro Ser Pro Leu Met Gly Gly Phe Gly Leu Lys
625                 630                 635                 640

His Pro Pro Pro Gln Ile Leu Ile Lys Asn Thr Pro Val Pro Ala Asn
                645                 650                 655

Pro Ser Thr Thr Phe Ser Ala Ala Lys Phe Ala Ser Phe Ile Thr Gln
            660                 665                 670

Tyr Ser Thr Gly Gln Val Ser Val Glu Ile Glu Trp Glu Leu Gln Lys
        675                 680                 685

Glu Asn Ser Lys Arg Trp Asn Pro Glu Ile Gln Tyr Thr Ser Asn Tyr
    690                 695                 700

Asn Lys Ser Val Asn Val Asp Phe Thr Val Asp Thr Asn Gly Val Tyr
705                 710                 715                 720

Ser Glu Pro Arg Pro Ile Gly Thr Arg Tyr Leu Thr Arg Asn Leu Ser
                725                 730                 735

Glu Pro Arg Pro Ile Gly Thr Arg Tyr Leu Thr Arg Asn Leu
            740                 745                 750

<210> SEQ ID NO 16
<211> LENGTH: 750
<212> TYPE: PRT
<213> ORGANISM: Adeno Associated Virus

<400> SEQUENCE: 16

Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro
            20                  25                  30

Lys Pro Ala Glu Arg His Lys Asp Asp Ser Arg Gly Leu Val Leu Pro
        35                  40                  45

Gly Tyr Lys Tyr Leu Gly Pro Phe Asn Gly Leu Asp Lys Gly Glu Pro
    50                  55                  60

```
Val Asn Glu Ala Asp Ala Ala Leu Glu His Asp Lys Ala Tyr Asp
 65                  70                  75                  80

Arg Gln Leu Asp Ser Gly Asp Asn Pro Tyr Leu Lys Tyr Asn His Ala
                 85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Pro Val Lys Thr Ala Pro Gly Lys Lys Arg
130                 135                 140

Pro Val Glu His Ser Pro Val Glu Pro Asp Ser Ser Gly Thr Gly
145                 150                 155                 160

Lys Ala Gly Gln Gln Pro Ala Arg Lys Arg Leu Asn Phe Gly Gln Thr
                165                 170                 175

Gly Asp Ala Asp Ser Val Pro Asp Pro Gln Pro Leu Gly Gln Pro Pro
            180                 185                 190

Ala Ala Pro Ser Gly Leu Gly Thr Asn Thr Met Ala Thr Gly Ser Gly
        195                 200                 205

Ala Pro Met Ala Asp Asn Asn Glu Gly Ala Asp Gly Val Gly Asn Ser
210                 215                 220

Ser Gly Asn Trp His Cys Asp Ser Thr Trp Met Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
            260                 265                 270

Phe Gly Tyr Ser Thr Pro Trp Gly Tyr Phe Asp Phe Asn Arg Phe His
        275                 280                 285

Cys His Phe Ser Pro Arg Asp Trp Gln Arg Leu Ile Asn Asn Asn Trp
290                 295                 300

Gly Phe Arg Pro Lys Arg Leu Asn Phe Lys Leu Phe Asn Ile Gln Val
305                 310                 315                 320

Lys Glu Val Thr Gln Asn Asp Gly Thr Thr Thr Ile Ala Asn Asn Leu
                325                 330                 335

Thr Ser Thr Val Gln Val Phe Thr Asp Ser Glu Tyr Gln Leu Pro Tyr
            340                 345                 350

Val Leu Gly Ser Ala His Gln Gly Cys Leu Pro Pro Phe Pro Ala Asp
        355                 360                 365

Val Phe Met Val Pro Gln Tyr Gly Tyr Leu Thr Leu Asn Asn Gly Ser
370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Thr Phe Ser Tyr Thr Phe Glu
                405                 410                 415

Asp Val Pro Phe His Ser Ser Tyr Ala His Ser Gln Ser Leu Asp Arg
            420                 425                 430

Leu Met Asn Pro Leu Ile Asp Gln Tyr Leu Tyr Tyr Leu Ser Arg Thr
        435                 440                 445

Ile Thr Pro Ser Gly Thr Thr Thr Gln Ser Arg Leu Gln Phe Ser Val
450                 455                 460

Ala Gly Pro Ser Asn Met Ala Val Gln Gly Arg Asn Trp Leu Pro Gly
465                 470                 475                 480
```

```
Pro Cys Tyr Arg Gln Gln Arg Val Ser Lys Thr Ser Ala Asp Asn Asn
                    485                 490                 495

Asn Ser Glu Tyr Ser Trp Thr Gly Ala Thr Lys Tyr His Leu Asn Gly
            500                 505                 510

Arg Asp Ser Leu Val Asn Pro Gly Pro Ala Met Ala Ser His Lys Asp
        515                 520                 525

Asp Glu Glu Lys Phe Phe Pro Gln Ser Gly Val Leu Ile Phe Gly Lys
    530                 535                 540

Gln Gly Ser Glu Lys Thr Asn Val Asp Ile Glu Lys Val Met Ile Thr
545                 550                 555                 560

Asp Glu Glu Glu Ile Arg Thr Thr Asn Pro Val Ala Thr Glu Gln Tyr
                565                 570                 575

Gly Ser Val Ser Thr Asn Leu Gln Arg Gly Asn Arg Gln Ala Ala Thr
            580                 585                 590

Ala Asp Val Asn Thr Gln Gly Val Leu Pro Gly Met Val Trp Gln Asp
        595                 600                 605

Arg Asp Val Tyr Leu Gln Gly Pro Ile Trp Ala Lys Ile Pro His Thr
    610                 615                 620

Asp Gly His Phe His Pro Ser Pro Leu Met Gly Gly Phe Gly Leu Lys
625                 630                 635                 640

His Pro Pro Pro Gln Ile Leu Ile Lys Asn Thr Pro Val Pro Ala Asn
                645                 650                 655

Pro Ser Thr Thr Phe Ser Ala Ala Lys Phe Ala Ser Phe Ile Thr Gln
            660                 665                 670

Tyr Ser Thr Gly Gln Val Ser Val Glu Ile Glu Trp Glu Leu Gln Lys
        675                 680                 685

Glu Asn Ser Lys Arg Trp Asn Pro Glu Ile Gln Tyr Thr Ser Asn Tyr
    690                 695                 700

Asn Lys Ser Val Asn Val Asp Phe Thr Val Asp Thr Asn Gly Val Tyr
705                 710                 715                 720

Ser Glu Pro Arg Pro Ile Gly Thr Arg Tyr Leu Thr Arg Asn Leu Ser
                725                 730                 735

Glu Pro Arg Pro Ile Gly Thr Arg Tyr Leu Thr Arg Asn Leu
            740                 745                 750

<210> SEQ ID NO 17
<211> LENGTH: 7910
<212> TYPE: DNA
<213> ORGANISM: Artificial Sequence
<220> FEATURE:
<223> OTHER INFORMATION: Plasmid construct

<400> SEQUENCE: 17
agcgcccaat acgcaaaccg cctctccccg cgcgttggcc gattcattaa tgcagctggc      60
acgacaggtt tcccgactgg aaagcgggca gtgagcgcaa cgcaattaat gtgagttagc     120
tcactcatta ggcaccccag gctttacact ttatgcttcc ggctcgtatg ttgtgtggaa     180
ttgtgagcgg ataacaattt cacacaggaa acagctatga ccatgattac gaattgcctg     240
caggcagctg cgcgctcgct cgctcactga ggccgcccgg gcaaagcccg ggcgtcgggc     300
gacctttggt cgcccggcct cagtgagcga gcgagcgcgc agagagggag tggccaactc     360
catcactagg ggttcctgga ggggtggagt cgtgacgtga attacgtcat agggttaggg     420
aggtcctgta ttagaggtca cgtgagtgtt ttgcgacatt ttgcgacacc atgtggtcac     480
gctgggtatt taagcccgag tgagcacgca gggtctccat tttgaagcgg gaggtttgaa     540
```

-continued

```
cgcgcagccg ccatgccggg gttttacgag attgtgatta aggtccccag cgaccttgac    600
gggcatctgc ccggcatttc tgacagcttt gtgaactggg tggccgagaa ggaatgggag    660
ttgccgccag attctgacat ggatctgaat ctgattgagc aggcaccect gaccgtggcc    720 gagaagctgc agcgcgactt tctgacggaa tggcgccgtg tgagtaaggc cccggaggcc    780
cttttctttg tgcaatttga aagggagag agctacttcc acatgcacgt gctcgtggaa    840
accaccgggg tgaaatccat ggttttggga cgtttcctga gtcagattcg cgaaaaactg    900
attcagagaa tttaccgcgg gatcgagccg actttgccaa actggttcgc ggtcacaaag    960
accagaaatg cgccggagg cgggaacaag gtggtggatg agtgctacat ccccaattac   1020
ttgctcccca aaacccagcc tgagctccag tgggcgtgga ctaatatgga acagtattta   1080
agcgcctgtt tgaatctcac ggagcgtaaa cggttggtgg cgcagcatct gacgcacgtg   1140
tcgcagacgc aggagcagaa caaagagaat cagaatccca attctgatgc gccggtgatc   1200
agatcaaaaa cttcagccag gtacatggag ctggtcgggt ggctcgtgga caaggggatt   1260
acctcggaga agcagtggat ccaggaggac caggcctcat acatctcctt caatgcggcc   1320
tccaactcgc ggtcccaaat caaggctgcc ttggacaatg cgggaaagat tatgagcctg   1380
actaaaaccg ccccegacta cctggtgggc cagcagcccg tggaggacat ttccagcaat   1440
cggatttata aaattttgga actaaacggg tacgatcccc aatatgcggc ttccgtcttt   1500
ctgggatggg ccacgaaaaa gttcggcaag aggaacacca tctggctgtt tgggcctgca   1560
actaccggga agaccaacat cgcggaggcc atagcccaca ctgtgccctt ctacgggtgc   1620
gtaaactgga ccaatgagaa ctttcccttc aacgactgtg tcgacaagat ggtgatctgg   1680
tgggaggagg ggaagatgac cgccaaggtc gtggagtcgg ccaaagccat tctcggagga   1740
agcaaggtgc gcgtggacca gaaatgcaag tcctcggccc agatagaccc gactcccgtg   1800
atcgtcacct ccaacaccaa catgtgcgcc gtgattgacg ggaactcaac gaccttcgaa   1860
caccagcagc cgttgcaaga ccggatgttc aaatttgaac tcacccgccg tctggatcat   1920
gactttggga aggtcaccaa gcaggaagtc aaagactttt ccggtgggc aaaggatcac   1980 gtggttgagt ggagcatga attctacgtc aaaaagggtg agccaagaa agacccgcc   2040 cccagtgacg cagatataag tgagcccaaa cgggtgcgcg agtcagttgc gcagccatcg   2100
acgtcagacg cggaagcttc gatcaactac gcagacaggt accaaaacaa atgttctcgt   2160
cacgtgggca tgaatctgat gctgtttccc tgcagacaat gcgagagaat gaatcagaat   2220
tcaaatatct gcttcactca cggacagaaa gactgtttag agtgctttcc cgtgtcagaa   2280
tctcaacccg tttctgtcgt caaaaaggcg tatcagaaac tgtgctacat tcatcatatc   2340
atgggaaagg tgccagacgc ttgcactgca tgcgatctgg tcaatgtgga tttggatgac   2400
tgcatctttg aacaataaat gatttaaatc aggtatggct gccgatggtt atcttccaga   2460
ttggctcgag gacactctct ctgaaggaat aagacagtgg tggaagctca acctggccc    2520 accaccacca aagcccgcag agcggcataa ggacgacagc aggggtcttg tgcttcctgg   2580
gtacaagtac ctcggaccct tcaacggact cgacaaggga gagccggtca acgaggcaga   2640
cgccgcggcc ctcgagcacg acaaagccta cgaccggcag ctcgacagcg agacaacccc   2700
gtacctcaag tacaaccacg ccgacgcgga gtttcaggag cgccttaaag aagatacgtc   2760
ttttgggggc aacctcggac gagcagtctt ccaggcgaaa aagagggttc ttgaacctct   2820
gggcctggtt gaggaacctg ttaagacggc tccgggaaaa aagaggccgg tagagcactc   2880
tcctgtggag ccagactcct cctccggaac cggaaaggcg gccagcagc ctgcaagaaa   2940
```

```
aagattgaat tttggtcaga ctggagacgc agactcagta cctgacccc  agcctctcgg    3000 acagccacca gcagcccct  ctggtctggg aactaatacg atggctacag gcagtggcgc    3060
accaatggca gacaataacg agggcgccga cggagtgggt aattcctcgg gaaattggca    3120
ttgcgattcc acatggatgg gcgacagagt catcaccacc agcacccgaa cctgggccct    3180
gcccacctac aacaaccacc tctacaaaca aatttccagc caatcaggag cctcgaacga    3240
caatcactac tttggctaca gcacccttg  ggggtatttt gacttcaaca gattccactg    3300
ccacttttca ccacgtgact ggcaaagact catcaacaac aactggggat tccgacccaa    3360
gagactcaac ttcaagctct ttaacattca agtcaaagag gtcacgcaga atgacggtac    3420
gacgacgatt gccaataacc ttaccagcac ggttcaggtg tttactgact cggagtacca    3480
gctcccgtac gtcctcggct cggcgcatca aggatgcctc ccgccgttcc cagcagacgt    3540
cttcatggtg ccacagtatg gatacctcac cctgaacaac gggagtcagg cagtaggacg    3600
atcttcattt tactgcctgg agtactttcc ttctcagatg ctgcgtaccg gaaacaactt    3660
taccttcagc tacacttttg aggacgttcc tttccacagc agctacgctc acagccagag    3720
tctggaccgt ctcatgaatc ctctcatcga ccagtacctg tattacttga gcagaacaaa    3780
cactccaagt ggaaccacca cgcagtcaag gcttcagttt tctcaggccg gagcgagtga    3840
cattcgggac cagtctagaa actggcttcc tggaccctgt taccgccagc agcgagtatc    3900
aaagacatct gcggataaca caacagtga  atactcgtgg actggagcta ccaagtacca    3960
cctcaatggc agagactctc tggtgaatcc gggcccggcc atggcaagcc acaaggacga    4020
tgaagaaaag ttttttcctc agagcgggt  tctcatctt  gggaagcaag gatcagagaa    4080
aacaaatgtg gacattgaaa aggtcatgat tacagacgaa gaggaaatca ggacaaccaa    4140
tcccgtggct acggagcagt atggttctgt atctaccaac ctccaggaag gcaacagaca    4200
agcagctacg gccgatgtca acacacaagg cgttcttcca ggcatggtct ggcaggacag    4260
agatgtgtac cttcagggc  ccatctgggc aaagattcca cacacggacg gacattttca    4320
cccctctccc ctcatggggtg gattcggact taaacaccct cctccacaga ttctcatcaa    4380
gaacaccccg gtacctgcga atccttcgac caccttcagt gcggcaaagt ttgcttcctt    4440
catcacacag tactccacgg gacaggtcag cgtggagatc gagtgggagc tgcagaagga    4500
aaacagcaaa cgctggaatc ccgaaattca gtacacttcc aactacaaca gtctgttaa     4560 tgtggacttt actgtggaca ctaatggcgt gtattcagag cctcgcccca ttggcaccag    4620 ataccctgact cgtaatctgt aattgcttgt taatcaataa accgtttaat tcgtttcagt    4680
tgaactttgg tctctgcgta tttctttctt atctagtttc catggctacg tagatctacc    4740
tacgtacttc cgctcatgct agcacggaaa tacgatgtcg ggatgtacag caaagacccc    4800
aacgagaagc gcgatcacat ggtcctgctg gagttcgtga ccgccgccta cgtagataag    4860
tagcatggcg ggttaatcat taactacaag gaaccctag  tgatggagtt ggccactccc    4920
tctctgcgcg ctcgctcgct cactgaggcc gggcgaccaa aggtcgcccg acgcccgggc    4980
tttgcccggg cggcctcagt gagcgagcga gcgcgcagct gcctgcaggc agcttggcac    5040
tggccgtcgt tttacaacgt cgtgactggg aaaaccctgg cgttacccaa cttaatcgcc    5100
ttgcagcaca tccccctttc gccagctggc gtaatagcga agaggcccgc accgatcgcc    5160
cttcccaaca gttgcgcagc ctgaatgcg  aatggcgcct gatgcggtat tttctcctta    5220
cgcatctgtg cggtatttca caccgcatac gtcaaagcaa ccatagtacg cgccctgtag    5280
```

```
cggcgcatta agcgcggcgg gtgtggtggt tacgcgcagc gtgaccgcta cacttgccag    5340
cgccctagcg cccgctcctt tcgctttctt cccttcctttctcgccacgt tcgccggctt    5400 tccccgtcaa gctctaaatc gggggctccc tttagggttc cgatttagtg ctttacggca    5460
cctcgacccc aaaaaacttg atttgggtga tggttcacgt agtgggccat cgccctgata    5520
gacggttttt cgcccttcga cgttggagtc cacgttcttt aatagtggac tcttgttcca    5580
aactggaaca acactcaacc ctatctcggg ctattctttt gatttataag gattttgcc     5640 gatttcggcc tattggttaa aaatgagct gatttaacaa aaatttaacg cgaattttaa     5700
caaaatatta acgtttacaa ttttatggtg cactctcagt acaatctgct ctgatgccgc    5760
atagttaagc cagccccgac acccgccaac acccgctgac gcgccctgac gggcttgtct    5820
gctcccggca tccgcttaca gacaagctgt gaccgtctcc gggagctgca tgtgtcagag    5880
gttttcaccg tcatcaccga aacgcgcgag acgaaagggc ctcgtgatac gcctattttt    5940
ataggttaat gtcatgataa taatggtttc ttagacgtca ggtggcactt ttcggggaaa    6000
tgtgcgcgga acccctattt gtttattttt ctaaatacat tcaaatatgt atccgctcat    6060
gagacaataa ccctgataaa tgcttcaata atattgaaaa aggaagagta tgagtattca    6120
acatttccgt gtcgccctta ttccctttttt gcggcattt tgccttcctg tttttgctca    6180
cccagaaacg ctggtgaaag taaaagatgc tgaagatcag ttgggtgcac gagtgggtta    6240
catcgaactg gatctcaaca gcggtaagat ccttgagagt tttcgccccg aagaacgttt    6300
tccaatgatg agcactttta aagttctgct atgtggcgcg gtattatccc gtattgacgc    6360
cgggcaagag caactcggtc gccgcataca ctattctcag aatgacttgg ttgagtactc    6420
accagtcaca gaaaagcatc ttacggatgg catgacagta agagaattat gcagtgctgc    6480
cataaccatg agtgataaca ctgcggccaa cttacttctg acaacgatcg gaggaccgaa    6540
ggagctaacc gcttttttgc acaacatggg ggatcatgta actcgccttg atcgttggga    6600
accggagctg aatgaagcca taccaaacga cgagcgtgac accacgatgc ctgtagcaat    6660
ggcaacaacg ttgcgcaaac tattaactgg cgaactactt actctagctt cccggcaaca    6720
attaatagac tggatggagg cggataaagt tgcaggacca cttctgcgct cggcccttcc    6780
ggctggctgg tttattgctg ataaatctgg agccggtgag cgtgggtctc gcggtatcat    6840
tgcagcactg gggccagatg gtaagccctc ccgtatcgta gttatctaca cgacggggag    6900
tcaggcaact atggatgaac gaaatagaca gatcgctgag ataggtgcct cactgattaa    6960
gcattggtaa ctgtcagacc aagtttactc atatatactt tagattgatt taaaacttca    7020
tttttaattt aaaaggatct aggtgaagat cctttttgat aatctcatga ccaaaatccc    7080
ttaacgtgag ttttcgttcc actgagcgtc agacccgta gaaagatca aaggatcttc     7140 ttgagatcct ttttttctgc gcgtaatctg ctgcttgcaa acaaaaaaac caccgctacc    7200
agcggtggtt tgtttgccgg atcaagagct accaactctt ttccgaagg taactggctt     7260 cagcagagcg cagataccaa atactgttct tctagtgtag ccgtagttag gccaccactt    7320
caagaactct gtagcaccgc ctacatacct cgctctgcta atcctgttac cagtggctgc    7380
tgccagtggc gataagtcgt gtcttaccgg gttggactca agacgatagt taccggataa    7440
ggcgcagcgg tcgggctgaa cggggggttc gtgcacacag cccagcttgg agcgaacgac    7500
ctacaccgaa ctgagatacc tacagcgtga gctatgagaa agcgccacgc ttcccgaagg    7560
gagaaaggcg gacaggtatc cggtaagcgg cagggtcgga acaggagagc gcacgaggga    7620
gcttccaggg ggaaacgcct ggtatcttta tagtcctgtc gggtttcgcc acctctgact    7680
```

-continued

```
tgagcgtcga ttttgtgat gctcgtcagg ggggcggagc ctatggaaaa acgccagcaa    7740
cgcggccttt ttacggttcc tggccttttg ctggccttt gctcacatgt tctttcctgc    7800
gttatcccct gattctgtgg ataaccgtat taccgccttt gagtgagctg ataccgctcg    7860
ccgcagccga acgaccgagc gcagcgagtc agtgagcgag gaagcggaag              7910
```

<210> SEQ ID NO 18
<211> LENGTH: 735
<212> TYPE: PRT
<213> ORGANISM: adeno associated virus

<400> SEQUENCE: 18

```
Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro
            20                  25                  30

Lys Pro Ala Glu Arg His Lys Asp Asp Ser Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Glu Ala Asp Ala Ala Leu Glu His Asp Lys Ala Tyr Asp
65                  70                  75                  80

Arg Gln Leu Asp Ser Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Pro Val Lys Thr Ala Pro Gly Lys Lys Arg
    130                 135                 140

Pro Val Glu His Ser Pro Val Glu Pro Asp Ser Ser Ser Gly Thr Gly
145                 150                 155                 160

Lys Ala Gly Gln Gln Pro Ala Arg Lys Arg Leu Asn Phe Gly Gln Thr
                165                 170                 175

Gly Asp Ala Asp Ser Val Pro Asp Pro Gln Pro Leu Gly Gln Pro Pro
            180                 185                 190

Ala Ala Pro Ser Gly Leu Gly Thr Asn Thr Met Ala Thr Gly Ser Gly
        195                 200                 205

Ala Pro Met Ala Asp Asn Asn Glu Gly Ala Asp Gly Val Gly Asn Ser
    210                 215                 220

Ser Gly Asn Trp His Cys Asp Ser Thr Trp Met Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
            260                 265                 270

Phe Gly Tyr Ser Thr Pro Trp Gly Tyr Phe Asp Phe Asn Arg Phe His
        275                 280                 285

Cys His Phe Ser Pro Arg Asp Trp Gln Arg Leu Ile Asn Asn Asn Trp
    290                 295                 300

Gly Phe Arg Pro Lys Arg Leu Asn Phe Lys Leu Phe Asn Ile Gln Val
305                 310                 315                 320

Lys Glu Val Thr Gln Asn Asp Gly Thr Thr Thr Ile Ala Asn Asn Leu
                325                 330                 335
```

```
Thr Ser Thr Val Gln Val Phe Thr Asp Ser Glu Tyr Gln Leu Pro Tyr
            340                 345                 350

Val Leu Gly Ser Ala His Gln Gly Cys Leu Pro Phe Pro Ala Asp
            355                 360                 365

Val Phe Met Val Pro Gln Tyr Gly Tyr Leu Thr Leu Asn Asn Gly Ser
370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Thr Phe Ser Tyr Thr Phe Glu
            405                 410                 415

Asp Val Pro Phe His Ser Ser Tyr Ala His Ser Gln Ser Leu Asp Arg
            420                 425                 430

Leu Met Asn Pro Leu Ile Asp Gln Tyr Leu Tyr Tyr Leu Ser Arg Thr
            435                 440                 445

Asn Thr Pro Ser Gly Thr Thr Thr Gln Ser Arg Leu Gln Phe Ser Gln
450                 455                 460

Ala Gly Pro Ser Asn Met Arg Asp Gln Ser Arg Asn Trp Leu Pro Gly
465                 470                 475                 480

Pro Cys Tyr Arg Gln Gln Arg Val Ser Lys Thr Ser Ala Asp Asn Asn
            485                 490                 495

Asn Ser Glu Tyr Ser Trp Thr Gly Ala Thr Lys Tyr His Leu Asn Gly
            500                 505                 510

Arg Asp Ser Leu Val Asn Pro Gly Pro Ala Met Ala Ser His Lys Asp
            515                 520                 525

Asp Glu Glu Lys Phe Phe Pro Gln Ser Gly Val Leu Ile Phe Gly Lys
530                 535                 540

Gln Gly Ser Glu Lys Thr Asn Val Asp Ile Glu Lys Val Met Ile Thr
545                 550                 555                 560

Asp Glu Glu Glu Ile Arg Thr Thr Asn Pro Val Ala Thr Glu Gln Tyr
            565                 570                 575

Gly Ser Val Ser Thr Asn Leu Gln Arg Gly Asn Arg Gln Ala Ala Thr
            580                 585                 590

Ala Asp Val Asn Thr Gln Gly Val Leu Pro Gly Met Val Trp Gln Asp
            595                 600                 605

Arg Asp Val Tyr Leu Gln Gly Pro Ile Trp Ala Lys Ile Pro His Thr
            610                 615                 620

Asp Gly His Phe His Pro Ser Pro Leu Met Gly Gly Phe Gly Leu Lys
625                 630                 635                 640

His Pro Pro Pro Gln Ile Leu Ile Lys Asn Thr Pro Val Pro Ala Asn
            645                 650                 655

Pro Ser Thr Thr Phe Ser Ala Ala Lys Phe Ala Ser Phe Ile Thr Gln
            660                 665                 670

Tyr Ser Thr Gly Gln Val Ser Val Glu Ile Glu Trp Glu Leu Gln Lys
            675                 680                 685

Glu Asn Ser Lys Arg Trp Asn Pro Glu Ile Gln Tyr Thr Ser Asn Tyr
            690                 695                 700

Asn Lys Ser Val Asn Val Asp Phe Thr Val Asp Thr Asn Gly Val Tyr
705                 710                 715                 720

Ser Glu Pro Arg Pro Ile Gly Thr Arg Tyr Leu Thr Arg Asn Leu
            725                 730                 735

<210> SEQ ID NO 19
<211> LENGTH: 735
```

<212> TYPE: PRT
<213> ORGANISM: adeno associated virus

<400> SEQUENCE: 19

Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro Pro
            20                  25                  30

Lys Pro Ala Glu Arg His Lys Asp Asp Ser Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Glu Ala Asp Ala Ala Leu Glu His Asp Lys Ala Tyr Asp
65                  70                  75                  80

Arg Gln Leu Asp Ser Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Pro Val Lys Thr Ala Pro Gly Lys Lys Arg
    130                 135                 140

Pro Val Glu His Ser Pro Val Glu Pro Asp Ser Ser Ser Gly Thr Gly
145                 150                 155                 160

Lys Ala Gly Gln Gln Pro Ala Arg Lys Arg Leu Asn Phe Gly Gln Thr
                165                 170                 175

Gly Asp Ala Asp Ser Val Pro Asp Pro Gln Pro Leu Gly Gln Pro Pro
            180                 185                 190

Ala Ala Pro Ser Gly Leu Gly Thr Asn Thr Met Ala Thr Gly Ser Gly
        195                 200                 205

Ala Pro Met Ala Asp Asn Asn Glu Gly Ala Asp Gly Val Gly Asn Ser
    210                 215                 220

Ser Gly Asn Trp His Cys Asp Ser Thr Trp Met Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
            260                 265                 270

Phe Gly Tyr Ser Thr Pro Trp Gly Tyr Phe Asp Phe Asn Arg Phe His
        275                 280                 285

Cys His Phe Ser Pro Arg Asp Trp Gln Arg Leu Ile Asn Asn Asn Trp
    290                 295                 300

Gly Phe Arg Pro Lys Arg Leu Asn Phe Lys Leu Phe Asn Ile Gln Val
305                 310                 315                 320

Lys Glu Val Thr Gln Asn Asp Gly Thr Thr Thr Ile Ala Asn Asn Leu
                325                 330                 335

Thr Ser Thr Val Gln Val Phe Thr Asp Ser Glu Tyr Gln Leu Pro Tyr
            340                 345                 350

Val Leu Gly Ser Ala His Gln Gly Cys Leu Pro Pro Phe Pro Ala Asp
        355                 360                 365

Val Phe Met Val Pro Gln Tyr Gly Tyr Leu Thr Leu Asn Asn Gly Ser
    370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Phe Thr Phe Ser Tyr Thr Phe Glu
              405                 410                 415

Asp Val Pro Phe His Ser Ser Tyr Ala His Ser Gln Ser Leu Asp Arg
            420                 425                 430

Leu Met Asn Pro Leu Ile Asp Gln Tyr Leu Tyr Tyr Leu Ser Arg Thr
            435                 440                 445

Asn Thr Pro Ser Gly Thr Thr Thr Gln Ser Arg Leu Gln Phe Ser Gln
            450                 455                 460

Ala Gly Pro Ser Asn Met Ala Val Gln Ser Arg Asn Trp Leu Pro Gly
465                 470                 475                 480

Pro Cys Tyr Arg Gln Gln Arg Val Ser Lys Thr Ser Ala Asp Asn Asn
                485                 490                 495

Asn Ser Glu Tyr Ser Trp Thr Gly Ala Thr Lys Tyr His Leu Asn Gly
            500                 505                 510

Arg Asp Ser Leu Val Asn Pro Gly Pro Ala Met Ala Ser His Lys Asp
            515                 520                 525

Asp Glu Glu Lys Phe Phe Pro Gln Ser Gly Val Leu Ile Phe Gly Lys
530                 535                 540

Gln Gly Ser Glu Lys Thr Asn Val Asp Ile Glu Lys Val Met Ile Thr
545                 550                 555                 560

Asp Glu Glu Ile Arg Thr Thr Asn Pro Val Ala Thr Glu Gln Tyr
                565                 570                 575

Gly Ser Val Ser Thr Asn Leu Gln Arg Gly Asn Arg Gln Ala Ala Thr
            580                 585                 590

Ala Asp Val Asn Thr Gln Gly Val Leu Pro Gly Met Val Trp Gln Asp
            595                 600                 605

Arg Asp Val Tyr Leu Gln Gly Pro Ile Trp Ala Lys Ile Pro His Thr
            610                 615                 620

Asp Gly His Phe His Pro Ser Pro Leu Met Gly Gly Phe Gly Leu Lys
625                 630                 635                 640

His Pro Pro Pro Gln Ile Leu Ile Lys Asn Thr Pro Val Pro Ala Asn
                645                 650                 655

Pro Ser Thr Thr Phe Ser Ala Ala Lys Phe Ala Ser Phe Ile Thr Gln
            660                 665                 670

Tyr Ser Thr Gly Gln Val Ser Val Glu Ile Glu Trp Glu Leu Gln Lys
            675                 680                 685

Glu Asn Ser Lys Arg Trp Asn Pro Glu Ile Gln Tyr Thr Ser Asn Tyr
690                 695                 700

Asn Lys Ser Val Asn Val Asp Phe Thr Val Asp Thr Asn Gly Val Tyr
705                 710                 715                 720

Ser Glu Pro Arg Pro Ile Gly Thr Arg Tyr Leu Thr Arg Asn Leu
                725                 730                 735

<210> SEQ ID NO 20
<211> LENGTH: 736
<212> TYPE: PRT
<213> ORGANISM: adeno associated virus

<400> SEQUENCE: 20

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro

```
                35                  40                  45
Gly Tyr Lys Tyr Leu Gly Pro Gly Asn Gly Leu Asp Lys Gly Glu Pro
 50                  55                  60

Val Asn Ala Ala Asp Ala Ala Leu Glu His Asp Lys Ala Tyr Asp
 65                  70                  75                  80

Gln Gln Leu Lys Ala Gly Asp Asn Pro Tyr Leu Lys Tyr Asn His Ala
                 85                  90                  95

Asp Ala Glu Phe Gln Glu Arg Leu Lys Glu Asp Thr Ser Phe Gly Gly
                100                 105                 110

Asn Leu Gly Arg Ala Val Phe Gln Ala Lys Lys Arg Leu Leu Glu Pro
            115                 120                 125

Leu Gly Leu Val Glu Glu Ala Ala Lys Thr Ala Pro Gly Lys Lys Arg
        130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
        355                 360                 365

Ala Asp Val Phe Met Ile Pro Gln Tyr Gly Tyr Leu Thr Leu Asn Asp
    370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
        435                 440                 445

Lys Thr Ile Asn Gly Ser Gly Gln Asn Gln Gln Thr Leu Lys Phe Ser
    450                 455                 460
```

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
            485                 490                 495

Asn Asn Ser Glu Phe Ala Trp Ala Ala Ser Ser Trp Ala Leu Asn
        500                 505                 510

Gly Arg Asn Ser Leu Met Asn Pro Gly Pro Ala Met Ala Ser His Lys
            515                 520                 525

Glu Gly Glu Asp Arg Phe Phe Pro Leu Ser Gly Ser Leu Ile Phe Gly
530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
            565                 570                 575

Tyr Gly Gln Val Ala Thr Asn His Gln Ser Ala Gln Ala Gln Ala Gln
            580                 585                 590

Thr Gly Trp Val Gln Asn Gln Gly Ile Leu Pro Gly Met Val Trp Gln
            595                 600                 605

Asp Arg Asp Val Tyr Leu Gln Gly Pro Ile Trp Ala Lys Ile Pro His
610                 615                 620

Thr Asp Gly Asn Phe His Pro Ser Pro Leu Met Gly Gly Phe Gly Met
625                 630                 635                 640

Lys His Pro Pro Pro Gln Ile Leu Ile Lys Asn Thr Pro Val Pro Ala
            645                 650                 655

Asp Pro Pro Thr Ala Phe Asn Lys Asp Lys Leu Asn Ser Phe Ile Thr
            660                 665                 670

Gln Tyr Ser Thr Gly Gln Val Ser Val Glu Ile Glu Trp Glu Leu Gln
            675                 680                 685

Lys Glu Asn Ser Lys Arg Trp Asn Pro Glu Ile Gln Tyr Thr Ser Asn
690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
            725                 730                 735

<210> SEQ ID NO 21
<211> LENGTH: 736
<212> TYPE: PRT
<213> ORGANISM: adeno associated virus

<400> SEQUENCE: 21

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
            85                  90                  95

Asp Ala Glu Phe Gln Glu Arg Leu Lys Glu Asp Thr Ser Phe Gly Gly

-continued

```
            100                 105                 110
Asn Leu Gly Arg Ala Val Phe Gln Ala Lys Lys Arg Leu Leu Glu Pro
        115                 120                 125
Leu Gly Leu Val Glu Ala Ala Lys Thr Ala Pro Gly Lys Lys Arg
    130                 135                 140
Pro Val Glu Gln Ser Pro Gln Glu Pro Asp Ser Ser Ala Gly Ile Gly
145                 150                 155                 160
Lys Ser Gly Ala Gln Pro Ala Lys Lys Arg Leu Asn Phe Gly Gln Thr
            165                 170                 175
Gly Asp Thr Glu Ser Val Pro Asp Pro Gln Pro Ile Gly Glu Pro Pro
            180                 185                 190
Ala Ala Pro Ser Gly Val Gly Ser Leu Thr Met Ala Ser Gly Gly Gly
        195                 200                 205
Ala Pro Val Ala Asp Asn Asn Glu Gly Ala Asp Gly Val Gly Ser Ser
    210                 215                 220
Ser Gly Asn Trp His Cys Asp Ser Gln Trp Leu Gly Asp Arg Val Ile
225                 230                 235                 240
Thr Thr Ser Thr Arg Thr Trp Ala Leu Pro Thr Tyr Asn Asn His Leu
            245                 250                 255
Tyr Lys Gln Ile Ser Asn Ser Thr Ser Gly Gly Ser Ser Asn Asp Asn
            260                 265                 270
Ala Tyr Phe Gly Tyr Ser Thr Pro Trp Gly Tyr Phe Asp Phe Asn Arg
        275                 280                 285
Phe His Cys His Phe Ser Pro Arg Asp Trp Gln Arg Leu Ile Asn Asn
    290                 295                 300
Asn Trp Gly Phe Arg Pro Lys Arg Leu Asn Phe Lys Leu Phe Asn Ile
305                 310                 315                 320
Gln Val Lys Glu Val Thr Asp Asn Asn Gly Val Lys Thr Ile Ala Asn
            325                 330                 335
Asn Leu Thr Ser Thr Val Gln Val Phe Thr Asp Ser Asp Tyr Gln Leu
            340                 345                 350
Pro Tyr Val Leu Gly Ser Ala His Glu Gly Cys Leu Pro Pro Phe Pro
        355                 360                 365
Ala Asp Val Phe Met Ile Pro Gln Tyr Gly Tyr Leu Thr Leu Asn Asp
    370                 375                 380
Gly Ser Gln Ala Val Gly Arg Ser Ser Phe Tyr Cys Leu Glu Tyr Phe
385                 390                 395                 400
Pro Ser Gln Met Leu Arg Thr Gly Asn Asn Phe Gln Phe Ser Tyr Glu
            405                 410                 415
Phe Glu Asn Val Pro Phe His Ser Ser Tyr Ala His Ser Gln Ser Leu
            420                 425                 430
Asp Arg Leu Met Asn Pro Leu Ile Asp Gln Tyr Leu Tyr Tyr Leu Ser
        435                 440                 445
Lys Thr Ile Asn Gly Ser Gly Gln Asn Gln Gln Thr Leu Lys Phe Ser
    450                 455                 460
Val Ala Gly Pro Ser Asn Met Ala Val Gln Gly Arg Asn Tyr Ile Pro
465                 470                 475                 480
Gly Pro Ser Tyr Arg Gln Gln Arg Val Ser Thr Thr Val Thr Gln Asn
            485                 490                 495
Asn Asn Ser Glu Phe Ala Trp Pro Gly Ala Ser Ser Trp Ala Leu Asn
            500                 505                 510
Gly Arg Asn Ser Leu Met Asn Pro Gly Pro Ala Met Ala Ser His Lys
        515                 520                 525
```

Glu Gly Glu Asp Arg Phe Phe Pro Leu Ser Gly Ser Leu Ile Phe Gly
    530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
            565                 570                 575

Tyr Gly Gln Val Ala Thr Asn His Gln Ser Ala Gln Ala Ala Ala Gln
            580                 585                 590

Thr Gly Trp Val Gln Asn Gln Gly Ile Leu Pro Gly Met Val Trp Gln
        595                 600                 605

Asp Arg Asp Val Tyr Leu Gln Gly Pro Ile Trp Ala Lys Ile Pro His
    610                 615                 620

Thr Asp Gly Asn Phe His Pro Ser Pro Leu Met Gly Gly Phe Gly Met
625                 630                 635                 640

Lys His Pro Pro Pro Gln Ile Leu Ile Lys Asn Thr Pro Val Pro Ala
            645                 650                 655

Asp Pro Pro Thr Ala Phe Asn Lys Asp Lys Leu Asn Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
    690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
            725                 730                 735

<210> SEQ ID NO 22
<211> LENGTH: 7327
<212> TYPE: DNA
<213> ORGANISM: Artificial Sequence
<220> FEATURE:
<223> OTHER INFORMATION: Plasmid

<400> SEQUENCE: 22
gcgcgccgat atcgttaacg ccccgcgccg ccgctctaga aactagtgga tccccggaa      60 gatcagaagt tcctattccg aagttcctat tctctagaaa gtataggaac ttctgatctg    120
cgcagccgcc atgccggggt tttacgagat tgtgattaag gtccccagcg accttgacga    180
gcatctgccc ggcatttctg acagctttgt gaactgggtg gccgagaagg aatgggagtt    240
gccgccagat tctgacatgg atctgaatct gattgagcag gcacccctga ccgtggccga    300
gaagctgcag cgcgactttc tgacggaatg gcgccgtgtg agtaaggccc ggaggcccct    360
tttctttgtg caatttgaga agggagagag ctacttccac atgcacgtgc tcgtggaaac    420
caccggggtg aaatccatgg tttttgggacg tttcctgagt cagattcgcg aaaaactgat    480
tcagagaatt taccgcggga tcgagccgac tttgccaaac tggttcgcgg tcacaaagac    540
cagaaatggc gccggaggcg ggaacaaggt ggtggatgag tgctacatcc ccaattactt    600
gctccccaaa acccagcctg agctccagtg ggcgtggact aatatggaac agtatttaag    660
cgcctgtttg aatctcacgg agcgtaaacg gttggtggcg cagcatctga cgcacgtgtc    720
gcagacgcag gagcagaaca aagagaatca gaatcccaat tctgatgcgc cggtgatcag    780
atcaaaaact tcagccaggt acatggagct ggtcgggtgg ctcgtggaca gggggattac    840
ctcggagaag cagtggatcc aggaggacca ggcctcatac atctccttca tgcggcctc    900

```
caactcgcgg tcccaaatca aggctgcctt ggacaatgcg ggaaagatta tgagcctgac    960
taaaaccgcc cccgactacc tggtgggcca gcagcccgtg gaggacattt ccagcaatcg   1020
gatttataaa attttggaac taaacgggta cgatccccaa tatgcggctt ccgtctttct   1080
gggatgggcc acgaaaaagt tcggcaagag gaacaccatc tggctgtttg ggcctgcaac   1140
taccgggaag accaacatcg cggaggccat agcccacact gtgcccttct acgggtgcgt   1200
aaactggacc aatgagaact ttcccttcaa cgactgtgtc gacaagatgg tgatctggtg   1260
ggaggagggg aagatgaccg ccaaggtcgt ggagtcggcc aaagccattc tcggaggaag   1320
caaggtgcgc gtggaccaga aatgcaagtc ctcggcccag atagacccga ctcccgtgat   1380
cgtcacctcc aacaccaaca tgtgcgccgt gattgacggg aactcaacga ccttcgaaca   1440
ccagcagccg ttgcaagacc ggatgttcaa atttgaactc acccgccgtc tggatcatga   1500
ctttgggaag gtcaccaagc aggaagtcaa agacttttc cggtgggcaa aggatcacgt   1560
ggttgaggtg gagcatgaat tctacgtcaa aaagggtgga gccaagaaaa gacccgcccc   1620
cagtgacgca gatataagtg agcccaaacg ggtgcgcgag tcagttgcgc agccatcgac   1680
gtcagacgcg gaagcttcga tcaactacgc agacaggtac caaaacaaat gttctcgtca   1740
cgtgggcatg aatctgatgc tgtttccctg cagacaatgc gagagaatga atcagaattc   1800
aaatatctgc ttcactcacg gacagaaaga ctgtttagag tgctttcccg tgtcagaatc   1860
tcaacccgtt tctgtcgtca aaaaggcgta tcagaaactg tgctacattc atcatatcat   1920
gggaaaggtg ccagacgctt gcactgcatg cgatctggtc aatgtggatt tggatgactg   1980
catctttgaa caataaatga tttaaatcag gtatggctgc cgatggttat cttccagatt   2040
ggctcgagga cactctctct gaaggaataa gacagtggtg gaagctcaaa cctggcccac   2100
caccaccaaa gcccgcagag cggcataagg acgacagcag gggtcttgtg cttcctgggt   2160
acaagtacct cggacccttc aacggactcg acaagggaga gccggtcaac gaggcagacg   2220
ccgcggccct cgagcacgac aaagcctacg accggcagct cgacagcgga gacaacccgt   2280
acctcaagta caaccacgcc gacgcggagt tcaggagcg cctcaaagaa gatacgtctt   2340
ttgggggcaa cctcggacga gcagtcttcc aggcgaaaaa gagggttctt gaacctctgg   2400
gcctggttga ggaacctgtt aagacggctc cgggaaaaaa gaggccggta gagcactctc   2460
ctgtggagcc agactcctcc tccggaaccg gaaaggcggg ccagcagcct gcaagaaaaa   2520
gattgaattt tggtcagact ggagacgcag actcagtacc tgaccccag cctctcggac   2580
agccaccagc agcccctct ggtctgggaa ctaatacgat ggctacaggc agtggcgcac   2640
caatggcaga caataacgag ggcgccgacg gagtgggtaa ttcctcggga aattggcatt   2700
gcgattccac atggatgggc gacagagtca tcaccaccag cacccgaacc tgggccctgc   2760
ccacctacaa caaccacctc tacaaacaaa tttccagcca atcaggagcc tcgaacgaca   2820
atcactactt tggctacagc accccttggg ggtattttga cttcaacaga ttccactgcc   2880
acttttcacc acgtgactgg caaagactca tcaacaacaa ctgggggattc gacccaaga   2940
gactcaactt caagctcttt aacattcaag tcaaagaggt cacgcagaat gacggtacga   3000
cgacgattgc caataacctt accagcacgg ttcaggtgtt tactgactcg gagtaccagc   3060
tcccgtacgt cctcggctcg gcgcatcaag gatgcctccc gccgttccca gcagacgtct   3120
tcatggtgcc acagtatgga tacctcaccc tgaacaacgg gagtcaggca gtaggacgat   3180
cttcatttta ctgcctggag tactttcctt ctcagatgct gcgtaccgga aacaactta   3240
```

```
ccttcagcta cacttttgag gacgttcctt tccacagcag ctacgctcac agccagagtc    3300
tggaccgtct catgaatcct ctcatcgacc agtacctgta ttacttgagc agaacaaaca    3360
ctccaagtgg aaccaccacg cagtcaaggc ttcagttttc tgtggccgga cccagtaaca    3420
tggctgtcca gggaagaaac tggcttcctg gaccctgtta ccgccagcag cgagtatcaa    3480
agacatctgc ggataacaac aacagtgaat ttgcttggac tggagctacc aagtaccacc    3540
tcaatggcag aaattctctg gtgaatccgg gcccggccat ggcaagccac aaggacgatg    3600
aagaaaagtt ttttcctcag agcggggttc tcatctttgg gaagcaagga tcagagaaaa    3660
caaatgtgga cattgaaaag gtcatgatta cagacgaaga ggaaatcagg acaaccaatc    3720
ccgtggctac ggagcagtat ggttctgtat ctaccaacct ccaggaaggc aacagacaag    3780
cagctacggc cgatgtcaac acacaaggcg ttcttccagg catggtctgg caggacagag    3840
atgtgtacct tcaggggccc atctgggcaa agattccaca cacggacgga cattttcacc    3900
cctctcccct catgggtgga ttcggactta acaccctcc tccacagatt ctcatcaaga    3960
acaccccggt acctgcgaat ccttcgacca ccttcagtgc ggcaaagttt gcttccttca    4020
tcacacagta ctccacggga caggtcagcg tggagatcga gtgggagctg cagaaggaaa    4080
acagcaaacg ctggaatccc gaaattcagt acacttccaa ctacaacaag tctgttaatg    4140
tggactttac tgtggacact aatggcgtgt attcagagcc tcgccccatt ggcaccagat    4200
acctgactcg taatctgtaa ttgcttgtta atcaataaac cgtttaattc gtttcagttg    4260
aactttggtc tctgcgtatt tctttcttat ctagtttcca tggctacgta gataagtagc    4320
atggcgggtt aatcattaac tacagcccgg gcgtttaaac agcgggcgga ggggtggagt    4380
cgtgacgtga attacgtcat agggttaggg aggtcctgta ttagaggtca cgtgagtgtt    4440
ttgcgacatt ttgcgacacc atgtggtctc gctggggggg ggggcccgag tgagcacgca    4500
gggtctccat tttgaagcgg gaggtttgaa cgagcgctgg cgcgctcact ggccgtcgtt    4560
ttacaacgtc gtgactggga aaaccctggc gttacccaac ttaatcgcct tgcagcacat    4620
ccccctttcg ccagctggcg taatagcgaa gaggcccgca ccgatcgccc ttcccaacag    4680
ttgcgcagcc tgaatggcga atggaaattg taagcgttaa tattttgtta aaattcgcgt    4740 taaattttg ttaaatcagc tcattttttt aaccaatagg ccgaaatcgg caaaatccct    4800
tataaatcaa agaatagac cgagatagg ttgagtgttg ttccagtttg gaacaagagt    4860
ccactattaa gaacgtggac tccaacgtca aagggcgaaa aaccgtctat cagggcgatg    4920
gcccactacg tgaaccatca ccctaatcaa gttttttggg gtcgaggtgc cgtaaagcac    4980
taaatcggaa ccctaaaggg agcccccgat ttagagcttg acggggaaag ccggcgaacg    5040
tggcgagaaa ggaagggaag aaagcgaaag gagcgggcgc tagggcgctg gcaagtgtag    5100
cggtcacgct gcgcgtaacc accacacccg ccgcgcttaa tgcgccgcta cagggcgcgt    5160
caggtggcac ttttcgggga atgtgcgcg gaacccctat ttgtttattt ttctaaatac    5220
attcaaatat gtatccgctc atgagacaat aaccctgata aatgcttcaa taatattgaa    5280
aaaggaagag tatgagtatt caacatttcc gtgtcgccct tattcccttt tttgcggcat    5340
tttgccttcc tgttttgct cacccagaaa cgctggtgaa agtaaaagat gctgaagatc    5400
agttgggtgc acgagtgggt tacatcgaac tggatctcaa cagcggtaag atccttgaga    5460
gttttcgccc cgaagaacgt tttccaatga tgagcacttt taaagttctg ctatgtggcg    5520
cggtattatc ccgtattgac gccgggcaag agcaactcgg tcgccgcata cactattctc    5580
agaatgactt ggttgagtac tcaccagtca cagaaaagca tcttacggat ggcatgacag    5640
```

-continued

```
taagagaatt atgcagtgct gccataacca tgagtgataa cactgcggcc aacttacttc   5700
tgacaacgat cggaggaccg aaggagctaa ccgcttttt gcacaacatg ggggatcatg   5760
taactcgcct tgatcgttgg aaccggagc tgaatgaagc cataccaaac gacgagcgtg   5820
acaccacgat gcctgtagca atggcaacaa cgttgcgcaa actattaact ggcgaactac   5880
ttactctagc ttcccggcaa caattaatag actggatgga ggcggataaa gttgcaggac   5940
cacttctgcg ctcggccctt ccggctggct ggttattgc tgataaatct ggagccggtg   6000
agcgtgggtc tcgcggtatc attgcagcac tggggccaga tggtaagccc tcccgtatcg   6060
tagttatcta cacgacgggg agtcaggcaa ctatggatga acgaaataga cagatcgctg   6120
agataggtgc ctcactgatt aagcattggt aactgtcaga ccaagtttac tcatatatac   6180
tttagattga tttaaaactt cattttaat ttaaaaggat ctaggtgaag atccttttg   6240
ataatctcat gaccaaaatc ccttaacgtg agttttcgtt ccactgagcg tcagaccccg   6300
tagaaaagat caaggatct tcttgagatc cttttttct gcgcgtaatc tgctgcttgc   6360
aaacaaaaaa accaccgcta ccagcggtgg tttgtttgcc ggatcaagag ctaccaactc   6420
ttttccgaa ggtaactggc ttcagcagag cgcagatacc aaatactgtt cttctagtgt   6480
agccgtagtt aggccaccac ttcaagaact ctgtagcacc gcctacatac ctcgctctgc   6540
taatcctgtt accagtggct gctgccagtg gcgataagtc gtgtcttacc gggttggact   6600
caagacgata gttaccggat aaggcgcagc ggtcgggctg aacggggggt tcgtgcacac   6660
agcccagctt ggagcgaacg acctacaccg aactgagata cctacagcgt gagctatgag   6720
aaagcgccac gcttcccgaa gggagaaagg cggacaggta tccggtaagc ggcagggtcg   6780
gaacaggaga gcgcacgagg gagcttccag ggggaaacgc ctggtatctt tatagtcctg   6840
tcgggtttcg ccacctctga cttgagcgtc gattttgtg atgctcgtca gggggcgga   6900
gcctatggaa aaacgccagc aacgcggcct ttttacggtt cctggccttt tgctggcctt   6960
ttgctcacat gttctttcct gcgttatccc ctgattctgt ggataaccgt attaccgcct   7020
ttgagtgagc tgataccgct cgccgcagcc gaacgaccga gcgcagcgag tcagtgagcg   7080
aggaagcgga agagcgccca atacgcaaac cgcctctccc cgcgcgttgg ccgattcatt   7140
aatgcagctg gcacgacagg tttcccgact ggaaagcggg cagtgagcgc aacgcaatta   7200
atgtgagtta gctcactcat taggcacccc aggctttaca ctttatgctt ccggctcgta   7260
tgttgtgtgg aattgtgagc ggataacaat ttcacacagg aaacagctat gaccatgatt   7320
acgccaa                                                             7327
```

<210> SEQ ID NO 23
<211> LENGTH: 735
<212> TYPE: PRT
<213> ORGANISM: adeno associated virus

<400> SEQUENCE: 23

```
Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro
            20                  25                  30

Lys Pro Ala Glu Arg His Lys Asp Asp Ser Arg Gly Leu Val Leu Pro
        35                  40                  45

Gly Tyr Lys Tyr Leu Gly Pro Phe Asn Gly Leu Asp Lys Gly Glu Pro
    50                  55                  60
```

-continued

Val Asn Glu Ala Asp Ala Ala Leu Glu His Asp Lys Ala Tyr Asp
65                  70                  75                  80

Arg Gln Leu Asp Ser Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Pro Val Lys Thr Ala Pro Gly Lys Lys Arg
    130                 135                 140

Pro Val Glu His Ser Pro Val Glu Pro Asp Ser Ser Gly Thr Gly
145                 150                 155                 160

Lys Ala Gly Gln Gln Pro Ala Arg Lys Arg Leu Asn Phe Gly Gln Thr
                165                 170                 175

Gly Asp Ala Asp Ser Val Pro Asp Pro Gln Pro Leu Gly Gln Pro Pro
            180                 185                 190

Ala Ala Pro Ser Gly Leu Gly Thr Asn Thr Met Ala Thr Gly Ser Gly
        195                 200                 205

Ala Pro Met Ala Asp Asn Asn Glu Gly Ala Asp Gly Val Gly Asn Ser
    210                 215                 220

Ser Gly Asn Trp His Cys Asp Ser Thr Trp Met Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
            260                 265                 270

Phe Gly Tyr Ser Thr Pro Trp Gly Tyr Phe Asp Phe Asn Arg Phe His
        275                 280                 285

Cys His Phe Ser Pro Arg Asp Trp Gln Arg Leu Ile Asn Asn Asn Trp
    290                 295                 300

Gly Phe Arg Pro Lys Arg Leu Asn Phe Lys Leu Phe Asn Ile Gln Val
305                 310                 315                 320

Lys Glu Val Thr Gln Asn Asp Gly Thr Thr Thr Ile Ala Asn Asn Leu
                325                 330                 335

Thr Ser Thr Val Gln Val Phe Thr Asp Ser Glu Tyr Gln Leu Pro Tyr
            340                 345                 350

Val Leu Gly Ser Ala His Gln Gly Cys Leu Pro Pro Phe Pro Ala Asp
        355                 360                 365

Val Phe Met Val Pro Gln Tyr Gly Tyr Leu Thr Leu Asn Asn Gly Ser
    370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Thr Phe Ser Tyr Thr Phe Glu
                405                 410                 415

Asp Val Pro Phe His Ser Ser Tyr Ala His Ser Gln Ser Leu Asp Arg
            420                 425                 430

Leu Met Asn Pro Leu Ile Asp Gln Tyr Leu Tyr Tyr Leu Ser Arg Thr
        435                 440                 445

Asn Thr Pro Ser Gly Thr Thr Thr Gln Ser Arg Leu Gln Phe Ser Val
    450                 455                 460

Ala Gly Pro Ser Asn Met Ala Val Gln Gly Arg Asn Trp Leu Pro Gly
465                 470                 475                 480

-continued

```
Pro Cys Tyr Arg Gln Gln Arg Val Ser Lys Thr Ser Ala Asp Asn Asn
                485                 490                 495

Asn Ser Glu Phe Ala Trp Ala Ala Thr Lys Tyr His Leu Asn Gly
        500                 505                 510

Arg Asn Ser Leu Val Asn Pro Gly Pro Ala Met Ala Ser His Lys Asp
            515                 520                 525

Asp Glu Glu Lys Phe Phe Pro Gln Ser Gly Val Leu Ile Phe Gly Lys
530                 535                 540

Gln Gly Ser Glu Lys Thr Asn Val Asp Ile Glu Lys Val Met Ile Thr
545                 550                 555                 560

Asp Glu Glu Glu Ile Arg Thr Thr Asn Pro Val Ala Thr Glu Gln Tyr
                565                 570                 575

Gly Ser Val Ser Thr Asn Leu Gln Arg Gly Asn Arg Gln Ala Ala Thr
            580                 585                 590

Ala Asp Val Asn Thr Gln Gly Val Leu Pro Gly Met Val Trp Gln Asp
        595                 600                 605

Arg Asp Val Tyr Leu Gln Gly Pro Ile Trp Ala Lys Ile Pro His Thr
610                 615                 620

Asp Gly His Phe His Pro Ser Pro Leu Met Gly Gly Phe Gly Leu Lys
625                 630                 635                 640

His Pro Pro Pro Gln Ile Leu Ile Lys Asn Thr Pro Val Pro Ala Asn
                645                 650                 655

Pro Ser Thr Thr Phe Ser Ala Ala Lys Phe Ala Ser Phe Ile Thr Gln
            660                 665                 670

Tyr Ser Thr Gly Gln Val Ser Val Glu Ile Glu Trp Glu Leu Gln Lys
        675                 680                 685

Glu Asn Ser Lys Arg Trp Asn Pro Glu Ile Gln Tyr Thr Ser Asn Tyr
690                 695                 700

Asn Lys Ser Val Asn Val Asp Phe Thr Val Asp Thr Asn Gly Val Tyr
705                 710                 715                 720

Ser Glu Pro Arg Pro Ile Gly Thr Arg Tyr Leu Thr Arg Asn Leu
                725                 730                 735

<210> SEQ ID NO 24
<211> LENGTH: 735
<212> TYPE: PRT
<213> ORGANISM: adeno associated virus

<400> SEQUENCE: 24

Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro
            20                  25                  30

Lys Pro Ala Glu Arg His Lys Asp Asp Ser Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Glu Ala Asp Ala Ala Leu Glu His Asp Lys Ala Tyr Asp
65                  70                  75                  80

Arg Gln Leu Asp Ser Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Val Leu Glu Pro
        115                 120                 125
```

-continued

```
Leu Gly Leu Val Glu Glu Pro Val Lys Thr Ala Pro Gly Lys Lys Arg
        130                 135                 140

Pro Val Glu His Ser Pro Val Glu Pro Asp Ser Ser Gly Thr Gly
145                 150                 155                 160

Lys Ala Gly Gln Gln Pro Ala Arg Lys Arg Leu Asn Phe Gly Gln Thr
                165                 170                 175

Gly Asp Ala Asp Ser Val Pro Asp Pro Gln Pro Leu Gly Gln Pro Pro
            180                 185                 190

Ala Ala Pro Ser Gly Leu Gly Thr Asn Thr Met Ala Thr Gly Ser Gly
            195                 200                 205

Ala Pro Met Ala Asp Asn Asn Glu Gly Ala Asp Gly Val Gly Asn Ser
210                 215                 220

Ser Gly Asn Trp His Cys Asp Ser Thr Trp Met Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
                260                 265                 270

Phe Gly Tyr Ser Thr Pro Trp Gly Tyr Phe Asp Phe Asn Arg Phe His
            275                 280                 285

Cys His Phe Ser Pro Arg Asp Trp Gln Arg Leu Ile Asn Asn Asn Trp
290                 295                 300

Gly Phe Arg Pro Lys Arg Leu Asn Phe Lys Leu Phe Asn Ile Gln Val
305                 310                 315                 320

Lys Glu Val Thr Gln Asn Asp Gly Thr Thr Thr Ile Ala Asn Asn Leu
                325                 330                 335

Thr Ser Thr Val Gln Val Phe Thr Asp Ser Glu Tyr Gln Leu Pro Tyr
            340                 345                 350

Val Leu Gly Ser Ala His Gln Gly Cys Leu Pro Pro Phe Pro Ala Asp
            355                 360                 365

Val Phe Met Val Pro Gln Tyr Gly Tyr Leu Thr Leu Asn Asn Gly Ser
370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Thr Phe Ser Tyr Thr Phe Glu
                405                 410                 415

Asp Val Pro Phe His Ser Ser Tyr Ala His Ser Gln Ser Leu Asp Arg
            420                 425                 430

Leu Met Asn Pro Leu Ile Asp Gln Tyr Leu Tyr Tyr Leu Ser Arg Thr
            435                 440                 445

Asn Thr Pro Ser Gly Thr Thr Thr Gln Ser Arg Leu Gln Phe Ser Val
            450                 455                 460

Ala Gly Pro Ser Asn Met Ala Val Gln Gly Arg Asn Trp Leu Pro Gly
465                 470                 475                 480

Pro Cys Tyr Arg Gln Gln Arg Val Ser Lys Thr Ser Ala Asp Asn Asn
                485                 490                 495

Asn Ser Glu Phe Ala Trp Thr Gly Ala Thr Lys Tyr His Leu Asn Gly
            500                 505                 510

Arg Asn Ser Leu Val Asn Pro Gly Pro Ala Met Ala Ser His Lys Asp
            515                 520                 525

Asp Glu Glu Lys Phe Phe Pro Gln Ser Gly Val Leu Ile Phe Gly Lys
530                 535                 540
```

-continued

```
Gln Gly Ser Glu Lys Thr Asn Val Asp Ile Glu Lys Val Met Ile Thr
545                 550                 555                 560

Asp Glu Glu Glu Ile Arg Thr Thr Asn Pro Val Ala Thr Glu Gln Tyr
            565                 570                 575

Gly Ser Val Ser Thr Asn Leu Gln Arg Gly Asn Arg Ala Ala Ala Thr
        580                 585                 590

Ala Asp Val Asn Thr Gln Gly Val Leu Pro Gly Met Val Trp Gln Asp
595                 600                 605

Arg Asp Val Tyr Leu Gln Gly Pro Ile Trp Ala Lys Ile Pro His Thr
    610                 615                 620

Asp Gly His Phe His Pro Ser Pro Leu Met Gly Gly Phe Gly Leu Lys
625                 630                 635                 640

His Pro Pro Pro Gln Ile Leu Ile Lys Asn Thr Pro Val Pro Ala Asn
            645                 650                 655

Pro Ser Thr Thr Phe Ser Ala Ala Lys Phe Ala Ser Phe Ile Thr Gln
        660                 665                 670

Tyr Ser Thr Gly Gln Val Ser Val Glu Ile Glu Trp Glu Leu Gln Lys
    675                 680                 685

Glu Asn Ser Lys Arg Trp Asn Pro Glu Ile Gln Tyr Thr Ser Asn Tyr
690                 695                 700

Asn Lys Ser Val Asn Val Asp Phe Thr Val Asp Thr Asn Gly Val Tyr
705                 710                 715                 720

Ser Glu Pro Arg Pro Ile Gly Thr Arg Tyr Leu Thr Arg Asn Leu
            725                 730                 735

<210> SEQ ID NO 25
<211> LENGTH: 735
<212> TYPE: PRT
<213> ORGANISM: adeno associated virus

<400> SEQUENCE: 25

Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro Pro
            20                  25                  30

Lys Pro Ala Glu Arg His Lys Asp Asp Ser Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Glu Ala Asp Ala Ala Ala Leu Glu His Asp Lys Ala Tyr Asp
65                  70                  75                  80

Arg Gln Leu Asp Ser Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Pro Val Lys Thr Ala Pro Gly Lys Lys Arg
    130                 135                 140

Pro Val Glu His Ser Pro Val Glu Pro Asp Ser Ser Ser Gly Thr Gly
145                 150                 155                 160

Lys Ala Gly Gln Gln Pro Ala Arg Lys Arg Leu Asn Phe Gly Gln Thr
                165                 170                 175

Gly Asp Ala Asp Ser Val Pro Asp Pro Gln Pro Leu Gly Gln Pro Pro
            180                 185                 190
```

```
Ala Ala Pro Ser Gly Leu Gly Thr Asn Thr Met Ala Thr Gly Ser Gly
            195                 200                 205

Ala Pro Met Ala Asp Asn Asn Glu Gly Ala Asp Gly Val Gly Asn Ser
210                 215                 220

Ser Gly Asn Trp His Cys Asp Ser Thr Trp Met Gly Asp Arg Val Ile
225                 230                 235                 240

Thr Thr Ser Thr Arg Thr Trp Ala Leu Pro Thr Tyr Asn Asn His Leu
            245                 250                 255

Tyr Lys Gln Ile Ser Ser Gln Ser Gly Ala Ser Asn Asp Asn His Tyr
            260                 265                 270

Phe Gly Tyr Ser Thr Pro Trp Gly Tyr Phe Asp Phe Asn Arg Phe His
            275                 280                 285

Cys His Phe Ser Pro Arg Asp Trp Gln Arg Leu Ile Asn Asn Asn Trp
            290                 295                 300

Gly Phe Arg Pro Lys Arg Leu Asn Phe Lys Leu Phe Asn Ile Gln Val
305                 310                 315                 320

Lys Glu Val Thr Gln Asn Asp Gly Thr Thr Thr Ile Ala Asn Asn Leu
            325                 330                 335

Thr Ser Thr Val Gln Val Phe Thr Asp Ser Glu Tyr Gln Leu Pro Tyr
            340                 345                 350

Val Leu Gly Ser Ala His Gln Gly Cys Leu Pro Pro Phe Pro Ala Asp
            355                 360                 365

Val Phe Met Val Pro Gln Tyr Gly Tyr Leu Thr Leu Asn Asn Gly Ser
            370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Thr Phe Ser Tyr Thr Phe Glu
            405                 410                 415

Asp Val Pro Phe His Ser Ser Tyr Ala His Ser Gln Ser Leu Asp Arg
            420                 425                 430

Leu Met Asn Pro Leu Ile Asp Gln Tyr Leu Tyr Tyr Leu Ser Arg Thr
            435                 440                 445

Asn Thr Pro Ser Gly Thr Thr Thr Gln Ser Arg Leu Gln Phe Ser Val
            450                 455                 460

Ala Gly Pro Ser Asn Met Ala Val Gln Gly Arg Asn Trp Leu Pro Gly
465                 470                 475                 480

Pro Cys Tyr Arg Gln Gln Arg Val Ser Lys Thr Ser Ala Asp Asn Asn
            485                 490                 495

Asn Ser Glu Phe Ala Trp Ala Ala Thr Lys Tyr His Leu Asn Gly
            500                 505                 510

Arg Asn Ser Leu Val Asn Pro Gly Pro Ala Met Ala Ser His Lys Asp
            515                 520                 525

Asp Glu Glu Lys Phe Phe Pro Gln Ser Gly Val Leu Ile Phe Gly Lys
            530                 535                 540

Gln Gly Ser Glu Lys Thr Asn Val Asp Ile Glu Lys Val Met Ile Thr
545                 550                 555                 560

Asp Glu Glu Glu Ile Arg Thr Thr Asn Pro Val Ala Thr Glu Gln Tyr
            565                 570                 575

Gly Ser Val Ser Thr Asn Leu Gln Arg Gly Asn Arg Ala Ala Ala Thr
            580                 585                 590

Ala Asp Val Asn Thr Gln Gly Val Leu Pro Gly Met Val Trp Gln Asp
            595                 600                 605
```

-continued

```
Arg Asp Val Tyr Leu Gln Gly Pro Ile Trp Ala Lys Ile Pro His Thr
    610                 615                 620
Asp Gly His Phe His Pro Ser Pro Leu Met Gly Gly Phe Gly Leu Lys
625                 630                 635                 640
His Pro Pro Pro Gln Ile Leu Ile Lys Asn Thr Pro Val Pro Ala Asn
                645                 650                 655
Pro Ser Thr Thr Phe Ser Ala Ala Lys Phe Ala Ser Phe Ile Thr Gln
                660                 665                 670
Tyr Ser Thr Gly Gln Val Ser Val Glu Ile Glu Trp Glu Leu Gln Lys
        675                 680                 685
Glu Asn Ser Lys Arg Trp Asn Pro Glu Ile Gln Tyr Thr Ser Asn Tyr
    690                 695                 700
Asn Lys Ser Val Asn Val Asp Phe Thr Val Asp Thr Asn Gly Val Tyr
705                 710                 715                 720
Ser Glu Pro Arg Pro Ile Gly Thr Arg Tyr Leu Thr Arg Asn Leu
                725                 730                 735
```